(12) United States Patent
Davaadorj et al.

(10) Patent No.: US 10,356,743 B2
(45) Date of Patent: Jul. 16, 2019

(54) SYSTEM AND METHOD FOR WIRELESS LOCATION

(71) Applicant: Neonic Corporation, Parker, CO (US)

(72) Inventors: Mishig Davaadorj, Ulaanbaatar (MN); Samuel H. Miller, Parker, CO (US); Cormac S. Siegfried, Sausalito, CA (US); Malcolm Gabbard, Walla Walla, WA (US)

( * ) Notice: Subject to any disclaimer, the term of this patent is extended or adjusted under 35 U.S.C. 154(b) by 0 days.

(21) Appl. No.: 15/671,088

(22) Filed: Aug. 7, 2017

(65) Prior Publication Data

US 2018/0041985 A1 Feb. 8, 2018

Related U.S. Application Data

(60) Provisional application No. 62/371,472, filed on Aug. 5, 2016.

(51) Int. Cl.
*H04W 24/00* (2009.01)
*G09B 3/00* (2006.01)
(Continued)

(52) U.S. Cl.
CPC ........... *H04W 64/003* (2013.01); *H04W 4/80* (2018.02); *H04W 84/18* (2013.01);
(Continued)

(58) Field of Classification Search
CPC ..... H04W 4/008; H04W 4/023; H04W 48/20; H04W 64/003; H04W 88/085
(Continued)

(56) References Cited

U.S. PATENT DOCUMENTS

| 5,835,849 A | 11/1998 | Duque-anton et al. |
| 6,195,399 B1 | 2/2001 | Dent et al. |
| (Continued) | | |

FOREIGN PATENT DOCUMENTS

| WO | WO 2014/096861 | 6/2014 |
| WO | WO 2017/077405 | 5/2017 |
| WO | WO 2018/027239 | 2/2018 |

OTHER PUBLICATIONS

Notification of Transmittal of the International Search Report and the Written Opinion of the International Searching Authority for International (PCT) Application No. PCT/US17/45805, dated Oct. 25, 2017, 12 pages.
(Continued)

*Primary Examiner* — Rafael Pérez-Gutiérrez
*Assistant Examiner* — Mark G. Pannell
(74) *Attorney, Agent, or Firm* — Aspire IP, LLC; Yiu F. Au; Scott J. Hawranek

(57) ABSTRACT

Systems and methods for wireless location are disclosed. In one aspect, a method for wireless location includes collecting signal strength values from one or more nodes (e.g., mobile devices) in an area over a time interval. The nodes receive wireless signals from one or more other transmitting nodes, where the signal strength values are representative of the signal strengths of the wireless signals. The method further includes normalizing the collected signal strength values and evaluating respective locations within the area of the nodes based on the normalized signal strength values. In a further aspect, the evaluated locations of the nodes may be used to execute an automated light show over the area, by instructing the nodes to display certain color or pattern at their locations in the area.

20 Claims, 47 Drawing Sheets
(8 of 47 Drawing Sheet(s) Filed in Color)

(51) Int. Cl.
*G06K 9/00* (2006.01)
*G01S 3/02* (2006.01)
*H04W 64/00* (2009.01)
*H04W 4/80* (2018.01)
*H04W 88/08* (2009.01)
*H04W 84/18* (2009.01)
*H04W 4/02* (2018.01)
*H04W 48/20* (2009.01)

(52) U.S. Cl.
CPC ......... *H04W 88/085* (2013.01); *H04W 4/023* (2013.01); *H04W 48/20* (2013.01)

(58) Field of Classification Search
USPC ..................................................... 455/456.1
See application file for complete search history.

(56) References Cited

U.S. PATENT DOCUMENTS

| | | | |
|---|---|---|---|
| 7,312,752 B2 | 12/2007 | Smith et al. | |
| 7,502,619 B1* | 3/2009 | Katz | G01S 5/02 455/456.5 |
| 8,077,090 B1* | 12/2011 | Chintalapudi | G01S 11/06 342/450 |
| 2001/0022558 A1* | 9/2001 | Karr, Jr. | G01S 1/026 342/450 |
| 2002/0013818 A1* | 1/2002 | Yamaga | G06Q 30/06 709/206 |
| 2002/0042834 A1 | 4/2002 | Kremens et al. | |
| 2002/0065467 A1* | 5/2002 | Schutt | A61B 5/055 600/454 |
| 2003/0146871 A1* | 8/2003 | Karr | G01S 1/026 342/457 |
| 2003/0222819 A1* | 12/2003 | Karr | G01C 21/206 342/457 |
| 2004/0146103 A1 | 7/2004 | Chang et al. | |
| 2005/0243936 A1* | 11/2005 | Agrawala | H04W 64/00 375/259 |
| 2007/0060098 A1* | 3/2007 | McCoy | G01S 5/0289 455/404.2 |
| 2007/0280006 A1 | 12/2007 | Aoyama et al. | |
| 2008/0188242 A1* | 8/2008 | Carlson | G01S 5/021 455/456.5 |
| 2009/0102642 A1* | 4/2009 | Huseth | G01S 5/14 340/539.13 |
| 2010/0073235 A1* | 3/2010 | Smith | G01S 5/021 342/451 |
| 2011/0098001 A1* | 4/2011 | Elsom-cook | G01S 3/20 455/41.2 |
| 2011/0269479 A1* | 11/2011 | Ledlie | G01S 5/0252 455/456.1 |
| 2012/0077513 A1* | 3/2012 | Rizzello | G01S 5/14 455/456.1 |
| 2013/0203036 A1* | 8/2013 | Jabara | H04W 4/80 434/350 |
| 2013/0260757 A1 | 10/2013 | Deivasigamani et al. | |
| 2014/0030982 A1 | 1/2014 | Cardona | |
| 2014/0185464 A1 | 7/2014 | Yang et al. | |
| 2014/0247280 A1* | 9/2014 | Nicholas | G06F 3/011 345/633 |
| 2014/0309836 A1* | 10/2014 | Ollis | G08G 1/22 701/25 |
| 2014/0315569 A1* | 10/2014 | Feigenblat | G01S 11/06 455/456.1 |
| 2015/0081071 A1 | 3/2015 | Lea et al. | |
| 2015/0102914 A1 | 4/2015 | Park | |
| 2015/0199699 A1* | 7/2015 | Milton | G06Q 30/02 705/7.34 |
| 2015/0200449 A1 | 7/2015 | Sleight et al. | |
| 2015/0276953 A1 | 10/2015 | Espana Palomares | |
| 2015/0347628 A1 | 12/2015 | Krajec et al. | |
| 2016/0078288 A1* | 3/2016 | Takatani | G06T 7/73 382/103 |
| 2016/0142266 A1 | 5/2016 | Carroll et al. | |
| 2016/0165690 A1 | 6/2016 | Benattar | |
| 2016/0202342 A1* | 7/2016 | Collins | G01S 5/0252 455/456.2 |
| 2017/0134902 A1* | 5/2017 | Bottazzi | H04W 4/023 |

OTHER PUBLICATIONS

Yang, et al., "Beyond Trilateration: ON the Localizability of Wireless Ad-hoc Networks", IEEE/ACME Transactions on Networking, vol. 18, No. 6 Dec. 2010.

PixMob, "PixMob—LED wristbands for enhanced crowd experiences", Retrieved from URL https://pixmob.com/en/ on Mar. 27, 2018, 3 pages.

MedTechGroup, "LED Products", Retrieved from URL http://www.medtechgroup.com/led-products on Mar. 27, 2018, 4 pages.

\* cited by examiner

|     | 31 (0,98) | 33 (12,98) | 27 (24,98) | 25 (36,98) | 23 (48,98) |
.5 meters

|     | 18 (0,79) | 20 (12,79) | 21 (24,79) | 22 (36,79) | 29 (48,79) |
.5 meters

|     | 17 (0,59) | 15 (12,59) | 14 (24,59) | 13 (36,59) | 12 (48,59) |
.5 meters

|     | 8 (0,39) | 9 (12,39) | 28 (24,39) | 10 (36,39) | 11 (48,39) |
.5 meters

|     | 7 (0,20) | 24 (12,20) | 6 (24,20) | 30 (36,20) | 5 (48,20) |
.5 meters

|     | 4 (0,0) | 32 (12,0) | 2 (24,0) | 26 (36,0) | 1 (48,0) |

12 inches  12 inches  12 inches  12 inches

*FIG. 14A*

SYSTEM AND METHOD FOR WIRELESS LOCATION

CROSS REFERENCE TO RELATED APPLICATION

This application claims the benefit of U.S. Provisional Application No. 62/371,472, filed Aug. 5, 2016, the content of which is fully incorporated by reference herein.

BACKGROUND OF THE INVENTION

Field of the Invention

The present invention generally relates to system and method for locating people or objects, and in particular, to a system and method for locating a wireless mobile station.

DISCUSSION OF THE BACKGROUND

There are deficiencies in systems and methods for wireless location in the related art. For example, wireless location systems in the related art typically cannot provide a relative position within sub-meter accuracy, without independent or specialized hardware. Also, it is difficult for even certain equipments that include specialized wireless location systems (e.g., Global Positioning System (GPS)) to achieve sub-meter accuracy. Therefore, it is difficult for wireless location systems to determine the relative positions of wireless devices in a relatively small and crowded area (e.g., in an area where devices are sub-meter spaced apart).

SUMMARY OF THE INVENTION

Accordingly, the invention is directed to a system and method for wireless location that substantially obviates one or more of the problems due to limitations and disadvantages of the related art.

An advantage of the invention is to provide relative position within sub-meter of accuracy independent of hardware other than wireless mobile station.

Another advantage of the invention is the ability to order the sequence of devices as they appear near a targeted device e.g. the ability to know what person is first in a line, know with certainty who is directly adjacent to a selected device, deliver goods or services directly to the correct device, discern targeted devices in a crowd, etc.

Yet another advantage of the invention is to provide a dynamically sequenced grid of wireless mobile stations at any location, independent of a network, to be used for any function in which location may be necessary but impossible using other methods, e.g., Global Positioning System (GPS), magnetic tracking, AP trilateration, etc.

Other systems in the related art pertaining to localization independent of GPS using received signal strength fail to provide a usable approximation of location. Even after employing access points, known RFID measurements, and advanced trilateration algorithms, no system has been successfully deployed to localize a plurality of devices in real world scenarios. Furthermore, the methods for testing the accuracy of the techniques of localization in the related art are derived from the methods used to measure the accuracy of GPS, e.g., accuracy of distance approximation between two devices and correlation with a reference frame, such as the GPS coordinate plane (maintained by the International Celestial Reference Frame). This mode of understanding accuracy is insufficient and outdated when the use case of a crowd of devices is not best served by a knowledge of the distance between two devices, but more preferably by the order in which these devices appear relative to each other.

Embodiments of the present invention achieve sub-meter radial accuracy, as understood by relative distance, relative position to other devices, and if available, a localized reference frame.

The present disclosure can provide a number of advantages depending on the particular aspect, embodiment, and/or configuration. These and other advantages will be apparent from the disclosure.

According to an embodiment, a method for wireless location comprises collecting a plurality of signal strength values from a plurality of nodes over a time interval, wherein the signal strength values are representative of signal strengths of respective plurality of wireless signals transmitted by at least one of the nodes to at least one other of the nodes, and wherein the nodes are located in an area; normalizing the collected signal strength values; and evaluating respective locations within the area of the nodes based on the normalized signal strength values. The method further comprises orienting the location coordinates to an orientation representative of an orientation of the nodes. The area includes an indoor facility. The area is less than 40 m by 40 m. A distance between at least two of nodes is less than an accuracy of Global Positioning System (GPS). The nodes comprise mobile devices. At least one of the nodes include a different equipment for transmitting or receiving the wireless signal than at least one other of the nodes. The signal strength values comprise received signal strength indicator (RSSI) values. The wireless signals comprise WI-FI signals. The wireless signals comprise BLUETOOTH signals. The wireless signals comprise wireless signals of communication in a mesh network, and wherein at least two of the nodes are part of the mesh network. The normalizing comprises normalizing the signal strength values with a normalization function, wherein the normalization function is based on a fit of previously collected signal strength values to a pre-determined normalization range. The previously collected signal strength values are collected from nodes with similar groups of wireless equipments as the nodes for transmitting or receiving the wireless signals. The fit comprises an exponential fit. The normalization function is based on a fit of averages of the previously collected signal strength values of nodes at a substantially same distance. The normalization function is based on a fit of averages of the previously collected signal strength values of nodes at a substantially same distance. The evaluating comprises evaluating using machine learning technique on the normalized signal strength values. The machine learning technique comprises a self-organizing map (SOM). Parameters for the SOM comprise a learning rate between 300 to 1000. Parameters for the SOM comprise a sigma rate between 1.0 to 20.0. The machine learning technique is trained to minimize an error to the locations. The locations comprise distances between the nodes. The locations comprise directions between a nodes. The evaluating comprises evaluating using a force directed graph. The orienting comprises evaluating the orientation using singular value decomposition. The method further comprises transmitting respective data to at least one of the nodes for controlling respective displays of the nodes based on the data. The transmitting is synchronized with music playing in the area in substantially real-time. The evaluating is performed by a server. The evaluating is performed by the mesh network.

In another embodiment, a wireless location system, comprises a plurality of wireless nodes positioned in an area, wherein at least one of the nodes is transmitting one or more wireless signals in the area, wherein the wireless signals are received by at least one of the other nodes, wherein signal strengths of the respective wireless signals are detected by the at least one other nodes as respective signal strength values; and one of more computational equipments configured for normalizing the collected signal strength values and evaluating respective locations within the area of the nodes based on the normalized signal strength values. The computational equipments are further configured for orienting the location coordinates to an orientation representative of an orientation of the nodes. The area includes an indoor facility. The area is less than 40 m by 40 m. A distance between at least two of the nodes is less than an accuracy of Global Positioning System (GPS). A distance between at least two of the nodes is less than 5 m. The nodes comprise mobile devices. At least one of the nodes include a different equipment for transmitting or receiving the wireless signal than at least one other of the nodes. The signal strength values comprise received signal strength indicator (RSSI) values. The wireless signals comprise WI-FI signals. The wireless signals comprise BLUETOOTH signals. The wireless signals comprise wireless signals of communication in a mesh network, and wherein at least two of the nodes are part of the mesh network. The normalizing comprises normalizing the signal strength values with a normalization function, wherein the normalization function is based on a fit of previously collected signal strength values to a pre-determined normalization range. The previously collected signal strength values are collected from nodes with similar groups of wireless equipments as the nodes for transmitting or receiving the wireless signals. The fit comprises an exponential fit. The normalization function is based on a fit of averages of the previously collected signal strength values of nodes at a substantially same distance. The normalization function is based on a fit of averages of the previously collected signal strength values of nodes at a substantially same distance. The evaluating comprises evaluating using machine learning technique on the normalized signal strength values. The machine learning technique comprises a self-organizing map (SOM). Parameters for the SOM comprise a learning rate between 300 to 1000. Parameters for the SOM comprise a sigma rate between 1.0 to 20.0. The machine learning technique is trained to minimize an error to the locations. The locations comprise distances between the nodes. The locations comprise directions between the nodes. The evaluating comprises evaluating using a force directed graph. The orienting comprises evaluating the orientation using singular value decomposition. The computational equipment are further configured for transmitting respective data to at least one of the nodes for controlling respective displays of the nodes based on the data. The transmitting is synchronized with music playing in the area in substantially real-time. The computational equipments comprise a server. The computational equipments comprise the nodes that are part of the mesh network.

In a further embodiment, a method for wireless location, comprises collecting a plurality of signal strength values from a plurality of nodes over a time interval, wherein the signal strength values are representative of signal strengths of respective plurality of wireless signals transmitted by at least one of the nodes to at least one other of the nodes, and wherein the nodes are located in an area; normalizing the collected signal strength values, wherein the normalizing comprises normalizing the signal strength values with normalization function, wherein the normalization function is based on a fit of previously collected signal strength values to a pre-determined normalization range; evaluating respective locations within the area of the nodes based on the normalized strength values, wherein the evaluating comprises evaluating using machine learning technique on the normalized signal strength values, and wherein the machine learning technique comprises a self-organizing map (SOM); and orienting the location coordinates to an orientation representative of an orientation of the nodes, wherein the area includes an indoor facility less than 40 m by 40 m, wherein a distance between at least two of the nodes is less than 5 m, wherein the nodes comprise mobile devices. At least one of the nodes include a different equipment for transmitting or receiving the wireless signal than at least one other of the nodes. The signal strength values comprise received signal strength indicator (RSSI) values. The wireless signals comprise WI-FI signals. The wireless signals comprise BLUETOOTH signals. The wireless signals comprise wireless signals of communication in a mesh network, and wherein at least two of the nodes are part of the mesh network. The previously collected signal strength values are collected from nodes with similar groups of wireless equipments as the nodes for transmitting or receiving the wireless signals. The fit comprises an exponential fit. The normalization function is based on a fit of averages of the previously collected signal strength values of nodes at a substantially same distance. The normalization function is based on a fit of averages of the previously collected signal strength values of nodes at a substantially same distance. Parameters for the SOM comprise learning rate between 300 to 1000. Parameters for the SOM comprise a sigma rate between 1.0 to 20.0. The machine learning technique is trained to minimize an error to the locations. The locations comprise distances between the nodes. The locations comprise directions between the nodes. The evaluating comprises evaluating using a force directed graph. The orienting comprises evaluating the orientation using singular value decomposition. The method further comprises transmitting respective data to at least one of the nodes for controlling respective displays of the nodes based on the data. The transmitting is synchronized with music playing in the area in substantially real-time. The evaluating is performed by a server. The evaluating is performed by the mesh network.

The terms described below are provided for convenience in understanding at least one embodiment of the present disclosure. Thus, the term descriptions following do not serve to necessarily define or limit the scope of these terms in all embodiments disclosed herein. In general, the term descriptions immediately below are also referenced in various portions of this disclosure of which such portions may expand upon these terms.

As used herein, the term crowd may, inter alia, refer to a plurality of devices in a locality. It is understood that an attempt to localize devices independent of GPS may require a plurality of devices and that a scenario in which such localization is desired may have a plurality of such devices available (e.g., in households, buildings, malls, airports, urban streets, etc.). Accordingly, embodiments of the present invention include novel methods for understanding accuracy of device-to-device localization, which may comprise one or more of:

a. ability to find another device in the crowd with an acceptable percentage of success;

b. the ability to determine the sequence, or order, of devices within the crowd with an acceptable percentage of success; and c. an ability to locate a device within a crowd to an acceptable degree of accuracy with relativity to the other devices.

As used herein, wireless mobile station or mobile device may refer to a wireless device that is at least a transmitting device, and in most cases is also a wireless receiving device, such as a portable radio telephony handset, BLUETOOTH beacon, mobile device, tablet, personal computer, automated teller, commercial register, etc.

The phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising," "including," "having" can be used interchangeably.

The term "automatic" and variation thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The term "module," as used herein, refers to any known or later developed hardware, software, firmware, artificial intelligence, fuzzy logic, or combination of hardware and software that is capable of performing the functionality associated with that element.

The terms "determine," "calculate," and "compute," and variations thereof, as used herein, are used interchangeably and include any type of methodology, process, mathematical operation or technique.

It shall be understood that the terms "means," as used herein, shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The preceding is a simplified summary of the disclosure to provide an understanding of some aspects of the disclosure. This summary is neither an extensive nor exhaustive overview of the disclosure and its various aspects, embodiments, and/or configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and/or configurations of the disclosure are possible, utilizing, alone or in combination, one or more of the features set forth above or described in detail below.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

This summary section is neither intended to be, nor should be, construed as being representative of the full extent and scope of the present disclosure. Additional benefits, features and embodiments of the present disclosure are set forth in the attached figures and in the description herein below, and as described by the claims. Accordingly, it should be understood that this Summary section may not contain all of the aspects and embodiments claimed herein.

Additionally, the disclosure herein is not meant to be limiting or restrictive in any manner. Moreover, the present disclosure is intended to provide an understanding to those of ordinary skill in the art of one or more representative embodiments supporting the claims. Thus, it is important that the claims be regarded as having a scope including constructions of various features of the present disclosure insofar as they do not depart from the scope of the methods apparatuses consistent with the present disclosure (including the originally filed claims). Moreover, the present disclosure is intended to encompass and include obvious improvements and modifications of the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6 is referenced for test layout nodes;

FIG. 14A illustrates an arrangement of nodes for Test A according to an embodiment;

Figure 1:
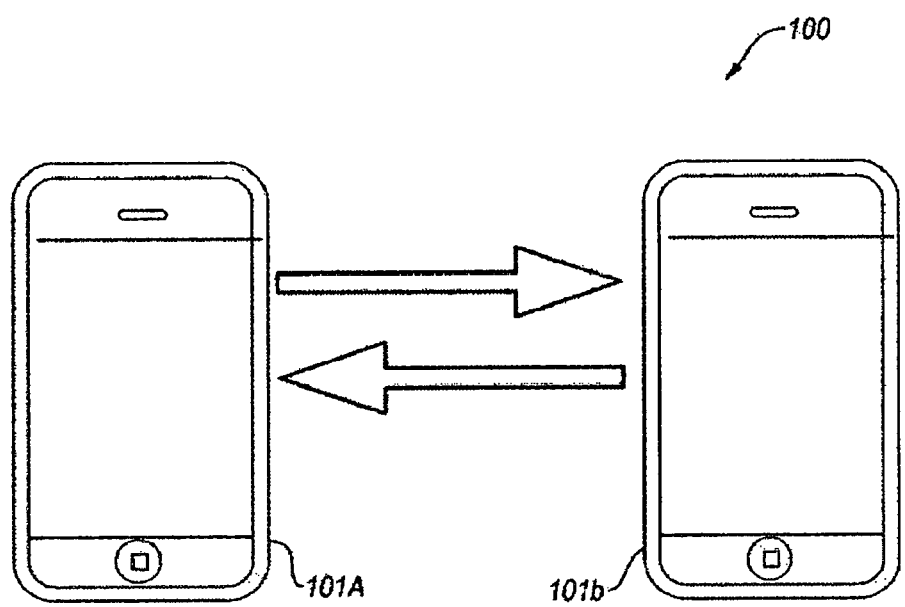
FIG. 1 illustrates a diagram of an exemplary communication system between two mobile stations.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

DETAILED DESCRIPTION OF THE ILLUSTRATED EMBODIMENTS

In order to more fully appreciate the present disclosure and to provide additional related features, the following references are incorporated herein by reference in their entirety:

(1) U.S. Pat. No. 7,312,752 by Smith, et al., which discloses techniques for accurate position location and tracking suitable for a wide range of facilities in variable environments are disclosed. In one aspect, a system for position location comprises a plurality of sensors (e.g. a network monitor, an environment sensor) for generating measurements of a plurality of sources, a plurality of objects or tags, each object generating measurements of the plurality of sources, and a processor for receiving the measurements and generating a position location for one or more objects in accordance with the received measurements. In another aspect, a position engine comprises a mapped space of a physical environment, and a processor for updating the mapped space in response to received measurements. The position engine may receive second measurements from an object within the physical environment, and generate a position location estimate for the object from the received second measurements and the mapped space. Various other aspects are also presented;

(2) U.S. Pat. No. 8,077,090 by Chintalapudi, et al., which discloses simultaneous localization and RF modeling technique that pertains to a method of providing simultaneous localization and radio frequency (RF) modeling. In one embodiment, the technique operates in a space with wireless local area network coverage (or other RF transmitters). Users carrying WI-FI-enabled devices traverse this space while the mobile devices record the Received Signal Strength (RSS) measurements corresponding to access points (APs) in view at various unknown locations and report these RSS measurements, as well as any other available location fix to a localization server. A RF modeling algorithm runs on the server and is used to estimate the location of the APs using the recorded RSSI measurements and any other available location information. All of the observations are constrained by the physics of wireless propagation. The technique models these constraints and uses a genetic algorithm to solve them, thereby providing an absolute location of the mobile device;

(3) U.S. Patent Application Publication No. 2008/0188242, by Carlson, et al., which discloses the location of a wireless mobile device may be estimated using, at least in part, one or more pre-existing Network Measurement Reports ("NMRs") which include calibration data for a number of locations within a geographic region. The calibration data for these locations is gathered and analyzed so that particular grid points within the geographic region can be determined and associated with a particular set or sets of calibration data from, for example, one or more NMRs. Embodiments of the present subject matter also provide a method of improving a location estimate of a mobile device. Received signal level measurements reported by a mobile device for which a location estimate is to be determined may be evaluated and/or compared with the characteristics associated with the various grid points to estimate the location of the mobile device;

(4) U.S. Patent Application Publication No. 2010/0073235 by Smith, et al., which discloses techniques for accurate position location and tracking suitable for a wide range of facilities in variable environments are disclosed. In one aspect, a system for position location comprises a plurality of sensors (e.g. a network monitor, an environment sensor) for generating measurements of a plurality of sources, a plurality of objects or tags, each object generating measurements of the plurality of sources, and a processor for receiving the measurements and generating a position location for one or more objects in accordance with the received measurements. In another aspect, a position engine comprises a mapped space of a physical environment, and a processor for updating the mapped space in response to received measurements. The position engine may receive second measurements from an object within the physical environment, and generate a position location estimate for the object from the received second measurements and the mapped space; and (5) Yang, et al, "Beyond Trilateration: On the Localizability of Wireless Ad-hoc Networks", IEEE/ACME Transactions on Networking, Vol. 18, No. 6 December 2010, which discloses localization being an essential service for many wireless sensor network applications. While several localization schemes rely on anchor nodes and range measurements to achieve fine-grained positioning, it proposed a range-free, anchor-free solution that works using connectivity information only. The approach, suitable for deployments with strict cost constraints, is based on the neural network paradigm of Self-Organizing Maps (SOM). A lightweight SOM-based algorithm to compute virtual coordinates that are effective for location-aided routing was presented. This algorithm can also exploit the location information, if available, of few anchor nodes to compute absolute positions. Results of extensive simulations show improvements over the popular Multi-Dimensional Scaling (MDS) scheme, especially for networks with low connectivity, which are intrinsically harder to localize, and in presence of irregular radio pattern or anisotropic deployment. It was analytically demonstrated that the proposed scheme has low computation and communication overheads; hence, making it suitable for resource-constrained networks.

Embodiments herein presented are not exhaustive, and further embodiments may be now known or later derived by one skilled in the art.

Functional units described in this specification and figures may be label as modules, or outputs in order to more particularly emphasize their structural features. A module and/or output may be implemented as hardware, e.g., comprising circuits, gate arrays, off-the-shelf semiconductors such as logic chips, transistors, or other discrete components. They may be fabricated with Very-large-scale integration (VLSI) techniques. A module and/or output may also be implemented in programmable hardware such as field programmable gate arrays, programmable array logic, programmable logic devices or the like. Modules may also be implemented in software for execution by various types of processors. In addition, the modules may be implemented as a combination of hardware and software in one embodiment.

An identified module of programmable or executable code may, for instance, include one or more physical or logical blocks of computer instructions that may, for instance, be organized as an object, procedure, or function. Components of a module need not necessarily be physically located together but may include disparate instructions stored in different locations which, when joined logically together, include the module and achieve the stated function for the module. The different locations may be performed on a network, device, server, and combinations of one or more of the same. A module and/or a program of executable code may be a single instruction, or many instructions, and may even be distributed over several different code segments, among different programs, and across several memory devices. Similarly, data or input for the execution of such modules may be identified and illustrated herein as being an encoding of the modules, or being within modules, and may be embodied in any suitable form and organized within any suitable type of data structure.

In one embodiment, the system, components and/or modules discussed herein may include one or more of the following: a server or other computing system including a processor for processing digital data, memory coupled to the processor for storing digital data, an input digitizer coupled to the processor for inputting digital data, an application program stored in one or more machine data memories and accessible by the processor is directing processing of digital data by the processor, a display device coupled to the processor and memory for displaying information derived from digital data processed by the processor, and a plurality of databases or data management systems.

In one embodiment, functional block components, screen shots, user interaction descriptions, optional selections, various processing steps, and the like are implemented with the system. It should be appreciated that such descriptions may be realized by any number of hardware and/or software components configured to perform the functions described. Accordingly, to implement such descriptions, various integrated circuit components, e.g., memory elements, processing elements, logic elements, look-up tables, input-output devices, displays and the like may be used, which may carry out a variety of functions under the control of one or more microprocessors or other control devices.

In one embodiment, software elements may be implemented with any programming, scripting language, and/or software development environment, e.g., Fortran, C. C++, C#, COBOL, Apache Tomcat, Spring Roo, Web Logic, Web Sphere, assembler, PERL, Visual Basic, SQL, SQL Stored Procedures, AJAX, extensible markup language (XML), Arduino, Flex, Flash, Java, .Net and the like. Moreover, the various functionalities in the embodiments may be implemented with any combination of data structures, objects, processes, routines or other programming elements.

In one embodiment, any number of conventional techniques for data transmission, signaling, data processing, network control, and the like as one skilled in the art will understand may be used. Further, detection or prevention of security issues using various techniques known in the art, e.g., encryption, may be also be used in embodiments of the invention. Additionally, many functional units and/or modules, e.g., shown in the figures, may be described as being "in communication" with other functional units and/or modules. Being "in communication" refers to any manner and/or way in which functional units and/or modules, such as, but not limited to, input/output devices, computers, laptop computers, PDAs, mobile devices, smart phones, modules, and types of hardware and/or software may be in communication with each other. Some non-limiting examples include communicating, sending and/or receiving data via a network, a wireless network, software, instructions, circuitry, phone lines, Internet lines, fiber optic lines, satellite signals, electrical signals, electrical and magnetic fields and/or pulses, and/or the like and combinations of the same.

By way of example, communication among the users, subscribers and/or server in accordance with embodiments of the invention may be accomplished through any suitable communication channels, such as, for example, a telephone network, an extranet, an intranet, the Internet, cloud based communication, point of interaction devices (point of sale device, personal digital assistant, cellular phone, kiosk, and the like), online communications, off-line communications, wireless communications, RF communications, cellular communications, WI-FI communications, transponder communications, local area network (LAN) communications, wide area network (WAN) communications, networked or linked devices and/or the like. Moreover, although embodiments of the invention may be implemented with TCP/IP communications protocols, other techniques of communication may also be implemented using IEEE protocols, IPX, Appletalk, IP-6, NetBIOS, OSI or any number of existing or future protocols. Specific information related to the protocols, standards, and application software utilized in connection with the Internet is generally known to those skilled in the art and, as such, need not be detailed herein.

In embodiments of the invention, the system provides and/or receives a communication or notification via the communication system to or from an end user. The communication is typically sent over a network, e.g., a communication network. The network may utilize one or more of a plurality of wireless communication standards, protocols or wireless interfaces (including LTE, CDMA, WCDMA, TDMA, UMTS, GSM, GPRS, OFDMA, WiMAX, FLO TV, Mobile DTV, WLAN, and BLUETOOTH technologies), and may be provided across multiple wireless network service providers. The system may be used with any mobile communication device service (e.g., texting, voice calls, games, videos, Internet access, online books, etc.), SMS, MMS, email, mobile, land phone, tablet, smartphone, television, vibrotactile glove, voice carry over, video phone, pager, relay service, teletypewriter, and/or GPS and combination of the same.

Reference will now be made in detail to embodiments of the present invention, an example of which is illustrated in the accompanying drawings.

FIG. 1 illustrates a diagram of an exemplary communication system between two mobile stations.

In communication system 100, mobile stations 101A and 101B each includes a transceiver for transmitting and receiving wireless signals in one or more wireless distribution methods (e.g., BLUETOOTH, WI-FI, etc.). Therefore, when mobile stations 101A and 101B are each capable of receiving wireless signals from the other mobile station when in range and using the same wireless distribution method. The received wireless signals have received signal strength indicators (RSSI) as measurements of the signal strength or power of the received wireless signals. The RSSI depends on the wireless channel and/or environment, and is generally a function of the distance between mobile stations 101A and 101B (e.g., the RSSI tends to decrease as the mobile station 101A and 101B are farther apart).

In one embodiment, received signal strength, e.g., RSSI from BLUETOOTH signal can be used to obtain or estimate location. For example, location of one or more mobile devices may be obtained or estimated by triangulation and/or trilateration. In another embodiment, the received signal strength may be utilize to obtain location and/or increase the certainty of location of the mobile device, e.g., a received BLUETOOTH RSSI may be a solution as there are multitudes of applications beyond our chosen lightshow/event management use case.

It is recognized that there exist some technical issues including poor location accuracy when using RSSI. However, the issues may be overcome by a deployment of multiple mobile devices according to an embodiment. For example, BLUETOOTH networks used in rooms of crowds of people (e.g., multiple mobile devices), as opposed to isolated rooms, can lead to greater amounts of data, thereby resulting in greater accuracy. In one example test herein below, twenty-one mobile devices, e.g., Motorola Moto E smart phones, were used to show increased accuracy.

In an embodiment, the relative positions (e.g., a position that relates to the order, or the sequence of one or more devices from any reference point, providing a reasonable approximation of the direction of devices relative to one or more of other devices), and not merely the actual position (e.g., a position (which may be estimated) that may be representative of the real location of the device in relation to the Earth, the surrounding environment and/or a reference location), of the mobile devices may be obtained or estimated. In one embodiment, the relative position can be used to estimate or predict an order in which the mobile devices are organized relative to each other. In one embodiment, the relative position can be used to estimate or predict the absolute position (e.g., a position known or estimated by a distance and a direction of each device relative to one or more of another, without necessarily having the knowledge of an orientation to the surrounding environment), which can then be oriented to predict or estimate an actual position.

One embodiment directed towards a coordinated lightshow using mobile devices as pixels in a crowd-sized screen may be accomplished. For example, once one or more of the actual position, the relative position, and/or the absolute position of at least a portion of the mobile devices can be determined or estimated in a crowd, the system may control such mobile devices to display a portion of a larger display (e.g., based on the position of the respective mobile devices). Therefore, the combination of the displays of the mobile devices at their respective positions may at least appear to make up the larger display when the crowd is viewed. In an embodiment, the displays may be controlled rhythmically (e.g., following the beat of music). In an embodiment, the displays may be automatically controlled through a program (e.g., programmed to display through a disc jockey (DJ) console through a Musical instrument Digital Interface (MIDI)).

In an embodiment, no additional hardware (besides the mobile devices) may be needed (e g., the mobile devices may be controlled through an app on the mobile devices and uses RSSI of the various received wireless signals supported by the mobile devices). This is advantageous for a number of reasons including decreasing costs, decreasing complexities, and allowing for ease of implementation, e.g., remote implementation. One of skill in the art could add and/or use additional hardware as now known or may be later derived. Optionally and/or alternatively, data streaming is not used to obtain location of the mobile devices. In another embodiment, the received signal strength may be utilized to obtain location and/or increase the certainty of location of the mobile device, e.g., a received BLUETOOTH RSSI may be a solution as there are multitudes of applications beyond a chosen light/display show and/or event management use case as previously discussed.

In one embodiment, embodiments of the sequencing and localization discussed in this disclosure may also be used to direct, coordinate, and aid emergency personnel responding to injury, overdose, theft, security threat, or any other concern to the public safety. In one example, embodiments can be used to alert authorities the location and type of emergency. In one example, the invention can be used to direct emergency responders to the locale of the emergency using phone screen cues, audio commands, and other direction techniques as now known or may be later derived. In one embodiment, embodiments can be used to direct civilians away from emergencies or toward safe areas. Embodiments are advantageous for emergency routing because they have the capacity to be independent of both a data network and energy grid as well as not significantly affected by environment.

In one embodiment, instead of attempting to perfect RSSI distance regressions, as is the method of GPS and related art, a device-to-device actual positioning can be used with relative position understood as an order of appearance, or sequence to determine location of the mobile device in a crowd of devices. Understanding that applications where localization is desirable but GPS is inadequate are naturally use cases involving a crowd, or a plurality of devices in proximity, such as in households, offices, airports, festivals, etc. In such use cases, precise location may be necessary to a tolerance yet achieved by GPS or BLE trilateration. In such use cases, distance between nodes is not as relevant as the relative direction between nodes or the relative sequence of nodes. Relative positioning is a much more approachable problem to solve. It can be used to achieve an awareness of the approximate location of devices allowing for the deployment of most wanted localization functions, e.g., finding a device, delivering to a device, collecting movement data, counting number of devices in an area, communicating with select localized groups, etc. In one embodiment, the relative positioning of the mobile devices can be used to determine absolution location at sub-meter resolution.

Figure 2:
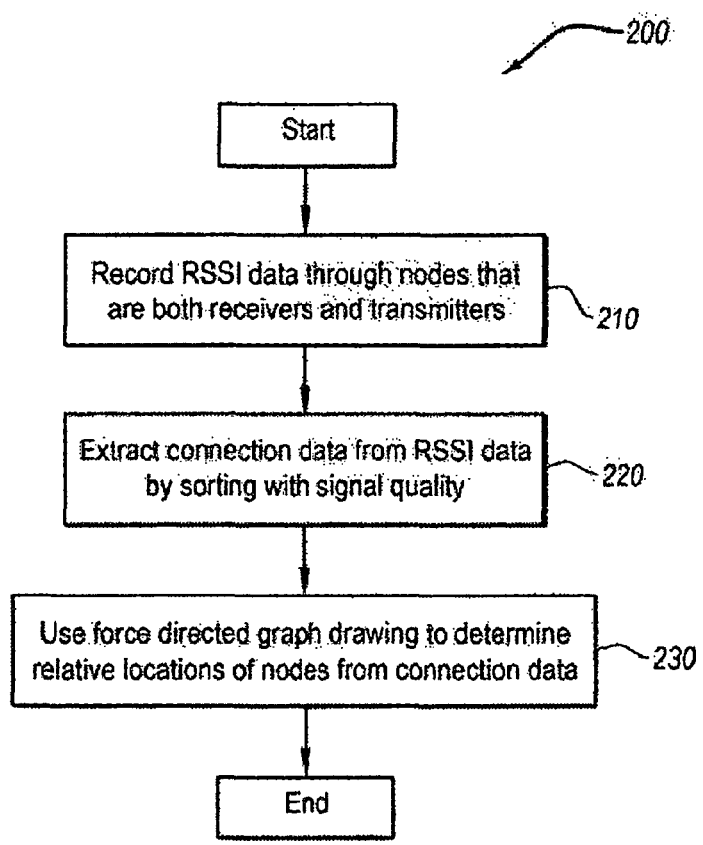
FIG. 2 illustrates flow diagram of an exemplary method of wireless location according to an embodiment.

FIG. 2 illustrates a flow diagram of an exemplary method of wireless location according to an embodiment.

Wireless location method 200 performs data collection, sorting, and using a force directed graph to determine relative location of nodes (e.g., mobile devices). The method 200 starts with recording RSSI data through nodes 210. In an embodiment, each node may include transmitters and receivers (e.g., mobile devices capable of both transmitting and receiving wireless signals from other mobile devices). Therefore, each node may receive and gather connection data (including RSSI data) with other nodes. In another embodiment, not all nodes may both transmit or receive data (some may perform only one transmitting or receiving). Therefore, the nodes may include incomplete connection and RSSI data. The incomplete data may be estimated, predicted, and/or extrapolated using techniques as known now or may be later derived.

The connection data received (including RSSI data) may be extracted and sorted 220. In an embodiment, the RSSI data may be extracted and/or sorted at each node or may be sorted at one or more centralized location (e.g., a centralize server or distributed servers). The extraction and sorting may include additional pre-processing such as normalization of the data based on the wireless or channel environment, equipment type (of the mobile devices), wireless signal power level (e.g., transmission power of individual mobile devices, which may be affected by battery power levels) and/or other parameters. In an embodiment, the data (e.g., RSSI data) may be represented by a matrix or other data representation to represent data for wireless signals transmitted and received by each pair (or some subset of the pairs in total) of nodes.

The locations of the nodes are determined from the connection data 230. In an embodiment, the relative locations of the nodes may be determined using a force directed graph drawing based on the correction data (e.g., RSSI data) in the matrix or other data representation. In another embodiment, the relative locations may be estimated by minimizing the error based on the connection data (e.g., through data analysis, using artificial intelligence, or by other methods).

Figure 3:
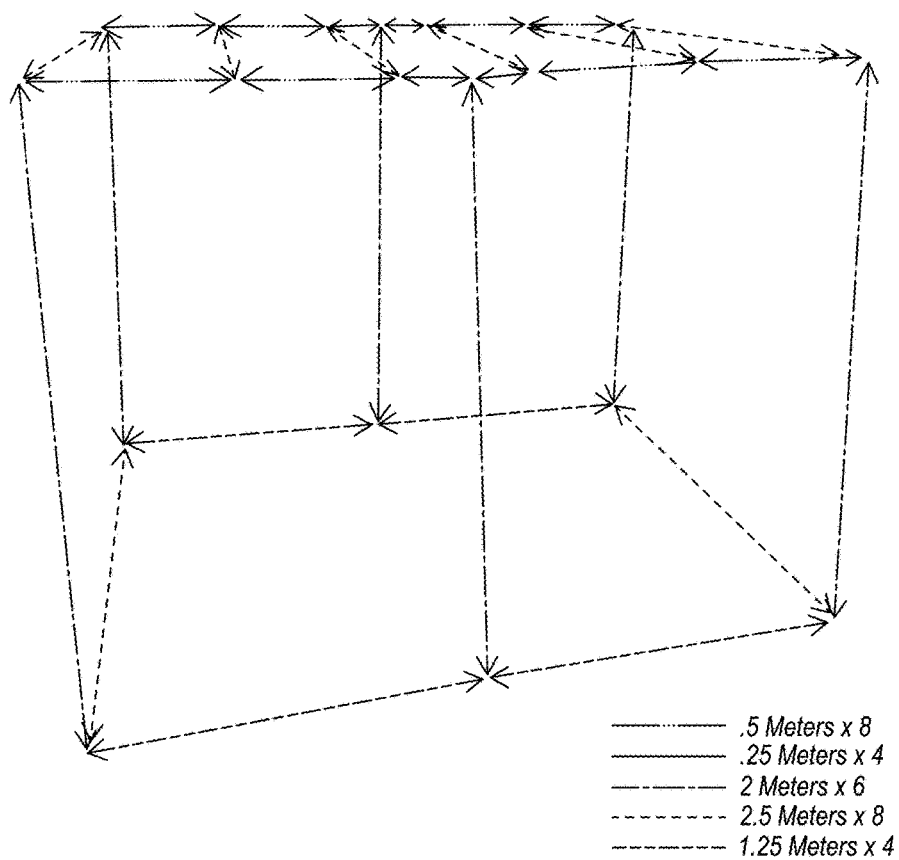
FIG. 3 shows a photograph of an exemplary experimental environment setup for a crowd of mobile devices in sub-meter spacing according to the embodiment.

FIG. 3 shows a photograph of an exemplary experimental environment setup for a crowd of mobile devices in sub-meter spacing according to an embodiment.

Referring to FIG. 3, the conduit structure in the setup is capable of hanging the 22 phones 5 feet off of the ground. This conduit structure used strings attached to paperclips to hang these mobile devices (e.g., phones). This setup was used for Test 5, 6-20 as will be described below.

In one experimental example as discussed herein, it can be shown RSSI was a relatively weak or poor indicator of distance (e.g., the location utilizing RSSI could not normally achieve sub-meter resolution, for example, trilateration). In this example, mobile devices were position by laying these devices with phones screen up in a 36 point half meter grid on the ground. The mobile devices were placed about 0.5 meters apart in a square of about 2.5 meters in side length. In order to better determine whether density of devices could improve accuracy a PVC structure that mimics our original 36 point half-meter grid but instead of the phones laying face up on the ground the phones can be suspended in the air with string and paper clips. We used this apparatus for all tests excepting the first 14.

Some precursor to experiments were conducted with wireless mobile stations, e.g., twenty-two (22) Moto-E 2nd gen Smart Phones where used in the precursor experiments.

Procedure:
1. Install an app on every wireless mobile station that allows the phone to act as both a beacon and receiver for RSSI, making sure the app logs the RSSI every time the receiver is pinged by a beacon.
2. Create a structure capable of hanging the 22 phones 5 feet off of the ground. We used a conduit structure which we tied strings to and attached the strings to the phone. FIG. 3 illustrates the structure used in the experiments.

Figure 4:
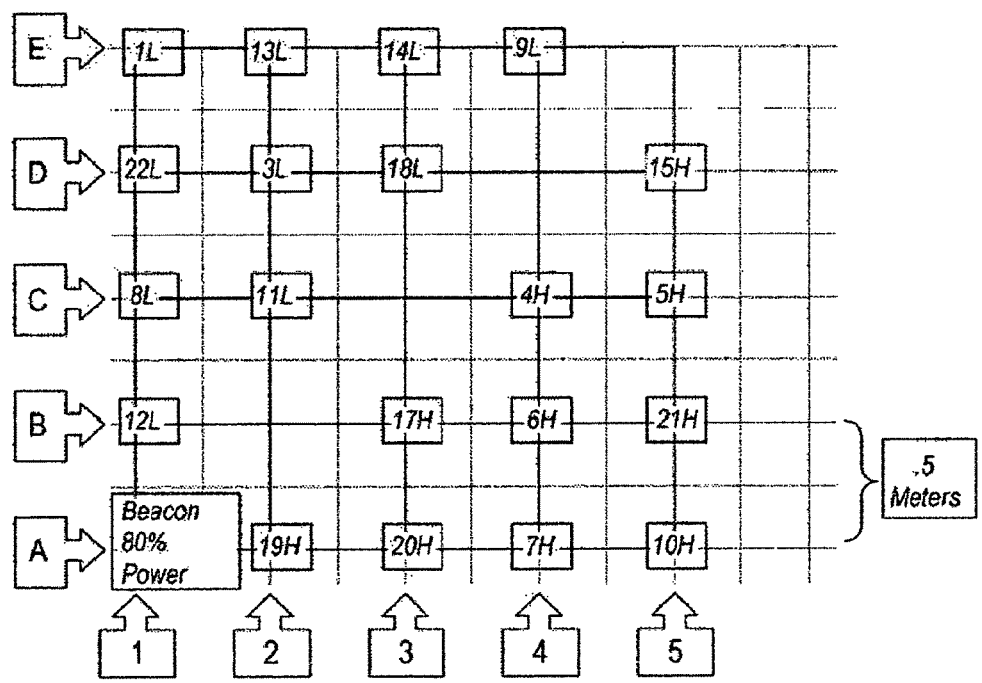
FIG. 4 illustrates an exemplary layout diagram for the phone layout of experimental test 1.

FIG. 4 illustrates an exemplary layout diagram for the phone layout of experimental test 1.

EXAMPLE 1

Test 1: High Versus Low Battery

Overview:

Phones were placed 0.5 meters apart on a grid on the floor of a garage like room. Phones were placed face up. There were no lights on, notable noises, people, BLUETOOTH, WI-FI, etc. in the room. The test ran for 5 minutes. This test measured the RSSI of phones with high battery compared to phones with low battery. This measurement was done by logging the RSSI for 5 minutes. No phones were placed along the diagonal except the beacon placed on A1 as shown in FIG. 4. One side of the diagonal consisted solely of phones with battery greater than 75% with the other side consisted only of phones with battery lower than 30% as shown in FIG. 4.

Procedure:
1: Remove all BLUETOOTH, WI-FI, and radio devices from the room.
2: Arrange phones in the pattern demonstrated in FIG. 4 such that phones marked with L are low battery phones (<30%) and phones marked with H are high battery phones (>75%). Additionally, note that in FIG. 4, the lighter grid lines indicate 0.25 meter intervals while the thicker grid lines are 0.5 meters.
3: Turn the beacon on.
4: Turn every receiver on and start collecting RSSI pings on each phone.
5: Exit the room.
6: Return after 5 minutes.
7: Turn the beacon and receivers off if they are still on.
8: Log all of the RSSI data.

Conclusion:

Upon comparing the average RSSI of phones with high-battery to the average RSSI of phones equally far away from the beacon with low battery we conclude that the effects of battery on average RSSI is negligible due to the fact that of the 10 pairs of phones at equal distance 6 of the low powered phones had higher RSSI values while 4 of the high powered phones did.

Figure 5:
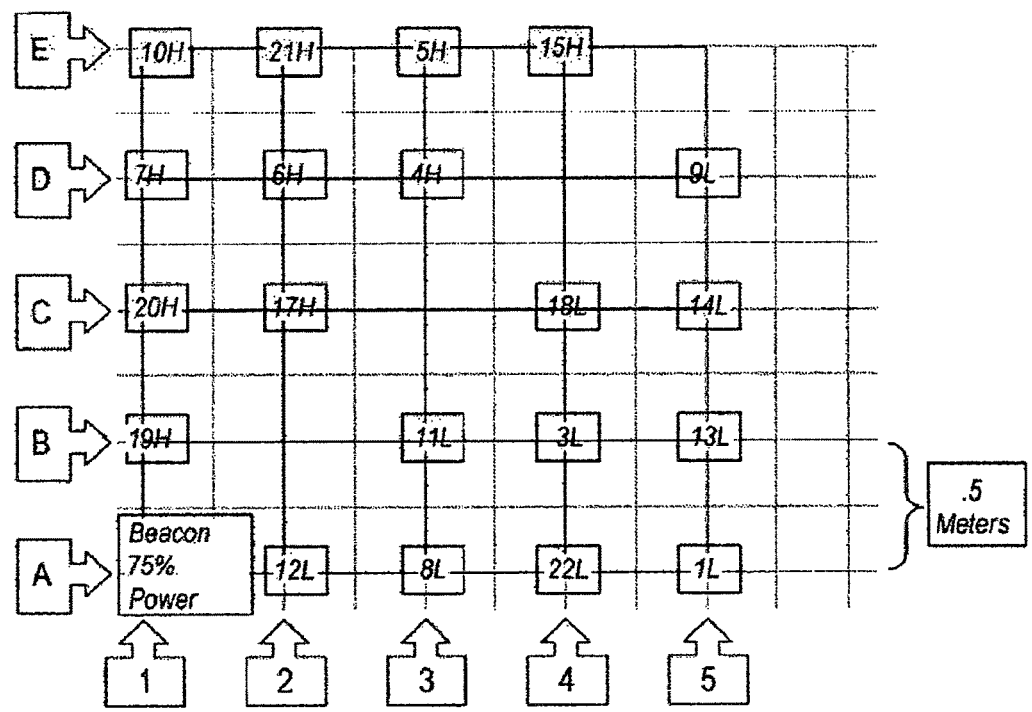
FIG. 5 illustrates an exemplary layout diagram layout for the phone layout of experimental test 2.

FIG. 5 illustrates an exemplary layout diagram for the phone layout of experimental test 2.

EXAMPLE 2

Test 2: Low Versus High Battery

Overview:

This test is identical to test 1 however the location of the phones is mirrored along the diagonal.

Procedure:
1: Remove all BLUETOOTH, WI-FI, and radio devices from the room.
2. Arrange phones in the pattern demonstrated in FIG. 5 such that phones marked with L are low battery phones (<30%) and phones marked with H are high battery phones (>75%). Additionally, note that in FIG. 5, the lighter grid lines indicate 0.25 meter intervals while the thicker grid lines are 0.5 meters.
3: Turn the beacon on.
4: Turn every receiver on and start collecting RSSI pings on each phone.
5: Exit the room.
6. Return after 5 minutes.
7: Turn the beacon and receivers off if they are still on.
8: Log all of the RSSI data.

Conclusion:

This test provided further validation of Test 2's findings that RSSI values recorded by receivers do not vary greatly when the receivers have different battery levels. This conclusion was reached do to the fact that, similar to test 1, of the 10 pairs of high battery and low battery phones 6 of the high powered phones had higher RSSI values and 4 of the low powered phone had higher RSSI values.

Figure 6:
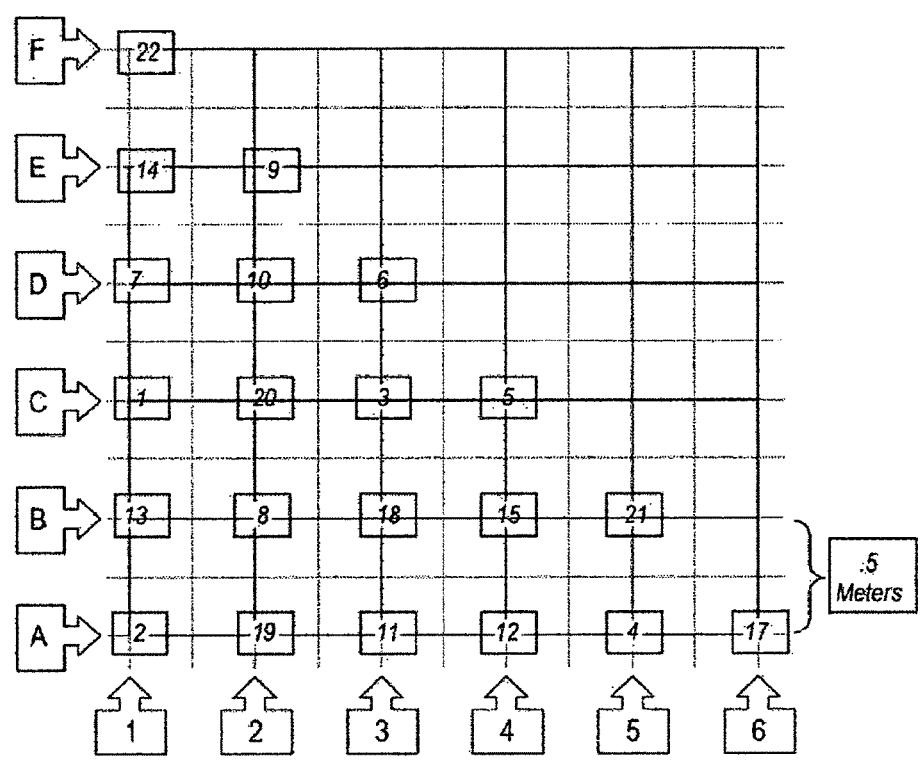
FIG. 6 illustrates an exemplary layout diagram for the phone layout of experimental tests 3-5 and tests 6-20.

FIG. 6 illustrates a exemplary layout diagram for the phone layout of experimental tests 3-5 and tests 6-20;

EXAMPLE 3

Test 3: Grounded Basis

Overview:

Phones were placed 0.5 meters apart on a grid on the floor of a garage like room. Phones were placed face up. There were no lights on, notable noises, people, BLUETOOTH, WI-FI, etc. in the room. The test ran for 5 minutes.

Procedure:
1: Remove all BLUETOOTH, WI-FI and radio devices from the room.
2: Arrange phones in the pattern demonstrated FIG. 6. Additionally, note that in FIG. 6, the lighter grid lines indicate 0.25 meter intervals while the thicker grid lines are 0.5 meters. Phone 2 is the beacon. All other phones are receivers.
3: Turn the beacon on and start collecting RSSI pings on each phone.
4: Turn every receiver on and start collecting RSSI pings on each phone.
5: Exit the room.
6: Return after 5 minutes.
7: Turn the beacon and receivers off if they are still on.
8: Log all of the RSSI data.

Conclusion:

Linear regressions of RSSI as a function of distance using the data from this test have an R-Squared value of 0.07 (7%) suggesting that increasing the distance between a receiver and a beacon has a causal, linear effect on RSSI. Additionally, when eliminating only one outlier (phone 17) the R-Squared value jumps to 0.17 which suggests that once mechanisms for identifying outliers are implemented accuracy will continue to grow at increasing rates.

EXAMPLE 4:

Test 4: Basis with Tarp

Overview:

This test is the same as test 3 however a thin tarp was placed over the phones.

Procedure:
1: Remove all BLUETOOTH, WI-FI, and radio devices from the room.
2: Arrange phones in the pattern demonstrated in FIG. 6. Additionally, note that in FIG. 6, the lighter grid lines indicate 0.25 meter intervals while the thicker grid lines are 0.5 meters. Phone 2 is the beacon. All other phones are receivers.
3: Turn the beacon on.
4: Turn every receiver on and start collecting RSSI pings on each phone.

5: Place a thin tarp over all of the phones including the beacon.
6: Exit the room.
7: Return after 5 minutes.
8: Turn the beacon and receivers off if they are still on.
9: Log all of the data.
Conclusion:
When comparing the best-fit lines between test 3 and test 4 the slope changes by only 0.0082 from 1.4727 to 1.4809 while the y intercept changes by 0.169 from 76.655 to 76.824. These changes are statistically insignificant allowing us to conclude that RSSI is not significantly impacted by thin covers on beacons or receivers.

EXAMPLE 5

Test 5: Hanger Basis

Overview:
Phones were placed 0.5 meters apart on a grid on the floor of an airplane hanger containing a cabin, fridge, TV etc. Phones were placed face up. There were no lights on, notable noises, people, BLUETOOTH, WI-FI, etc. in the room. The test ran for 5 minutes. The phones were placed in the South-East corner of the grid.
Procedure:
1: Remove all BLUETOOTH, WI-FI, and radio devices from the room.
2: Arrange phones in the pattern demonstrated in FIG. 6. Additionally, note that in FIG. 6, the lighter grid lines indicate 0.25 meter intervals while the thicker grid lines are 0.5 meters. Have the beacon in the south-eastern most corner of the grid. Phone 2 is the beacon. All other phones are receivers.
3: Turn the beacon on.
4: Turn every receiver on and start collecting RSSI pings on each phone.
5: Exit the room.
6: Return after 5 minutes.
7: Turn the beacon and receivers off if they are still on.
8: Log all of the data.
Conclusion:
In the new location the slope of the best-fit line increases from 1.4727 to 2.8708, a statistically insignificant change. However, the intercept increases from 76.655 to 81.716. This change in intercept indicates that while distance has similar effects on the BLUETOOTH signal regardless of locations, the actual values may vary. Graphically this takes the form of the best-fit lines being parallel but not identical.
Table 1 lists the average RSSI values for tests 1-5.

TABLE 1

| Phone ID | Distance From Beacon | Test 1 | Test 2 | Test 3 | Test 4 | Test 5 |
| --- | --- | --- | --- | --- | --- | --- |
| 1 | 1 | 77.42 | 78.49 | 80.45 | 75.74 | 80.81 |
| 3 | 1.414213562 | 79.98 | 77.12 | 77.16 | 77.49 | |
| 4 | 2 | 82.78 | 78.41 | 76.23 | 76.44 | 85.95 |
| 5 | 1.802775638 | 87.03 | 79.55 | 82.32 | 82.86 | 89.57 |
| 6 | 1.802775638 | 81.21 | 75.93 | 80.63 | 78.25 | 86.26 |
| 7 | 1.5 | 81.53 | 79.53 | 83 | 80.55 | 90.12 |
| 8 | 0.707106781 | 80.65 | 77.34 | 74.18 | 76.53 | |
| 9 | 2.061552813 | 81.89 | 83.97 | 84.47 | 87.79 | |
| 10 | 1.58113883 | 80.34 | 78.86 | 79.16 | 80.53 | 88.21 |
| 11 | 1 | | 82.35 | 77.73 | 75.52 | 89.99 |
| 12 | 1.5 | 70.2 | 75.01 | 80.4 | 82.35 | 89.01 |
| 13 | 0.5 | 79.2 | 84.87 | | 84.5 | 72.44 |
| 14 | 2 | 77.9 | 80.59 | 79.83 | 78.98 | 86 |
| 15 | 1.58113883 | 85.47 | 80.89 | 74.48 | 75.04 | 88.15 |
| 17 | 2.5 | 87.13 | 79.53 | 80.52 | 80.78 | 88.28 |
| 18 | 1.118033989 | 80.43 | 78.42 | 76.4 | | |

TABLE 1-continued

| Phone ID | Distance From Beacon | Test 1 | Test 2 | Test 3 | Test 4 | Test 5 |
| --- | --- | --- | --- | --- | --- | --- |
| 19 | 0.5 | 76.42 | 68.62 | 75.66 | 71.22 | 89.6 |
| 20 | 1.118033989 | 82.25 | 76.18 | 82.88 | 82.81 | 82.36 |
| 21 | 2.061552813 | 83.4 | 82.46 | 78.89 | 79.13 | 85.51 |
| 22 | 2.5 | 77.7 | 76.27 | 75.86 | 76.29 | 86.82 |

EXAMPLE 6

Test 6: Beacon in SW Corner

Overview:
Test 5 however the beacon was in the SW corner of the grid.
Procedure:
1: Remove all BLUETOOTH, WI-FI, and radio devices from the room.
2: Arrange phones in the pattern demonstrated in FIG. 6. Additionally, note that in FIG. 6, the lighter grid lines indicate 0.25 meter intervals while the thicker grid lines are 0.5 meters. Have the beacon in the south-western most corner of the grid. Phone 2 is the beacon. All other phones are receivers.
3: Turn the beacon on.
4: Turn every receiver on and start collecting RSSI pings on each phone.
5: Exit the room.
6: Return after 5 minutes.
7: Turn the beacon and receivers off if they are still on.
8: Log all of the data.
Conclusion:
With a 7.921 increase in the y-intercept of the best-fit line from test 5 to test 6 there appears to be a significant change between tests however, after eliminating phone 19, an obvious outlier, the difference between intercepts decreases to 4.8, a negligible difference, allowing us to infer that orientation within a setting doesn't affect RSSI.

EXAMPLE 7

Test 7: Beacon in NW Corner

Overview:
Test 5 however the beacon was in the NW corner of the grid.
Procedure
1: Remove all BLUETOOTH, WI-FI and radio devices from the room.
2: Arrange phones in the pattern demonstrated in FIG. 6. Additionally, note that in FIG. 6, the lighter grid lines indicate 0.25 meter intervals while the thicker grid lines are 0.5 meters. Have the beacon in the north-western most corner of the grid. Phone 2 is the beacon. All other phones are receivers.
3: Turn the beacon on.
4: Turn every receiver on and start collecting RSSI pings on each phone.
5: Exit the room.
6. Return after 5 minutes.
7: Turn the beacon and receivers off if they are still on.
8: Log all of the data.
Conclusion:
With a 3.92 increase in the y-intercept of the best-fit line from test 6 to test 7 we extend our inference from example 7 continuing to infer that orientation within a setting doesn't effect RSSI.

EXAMPLE 8

Test 8: Beacon in NE Corner

Overview:
Test 5 however the beacon was in the NE corner of the grid.

Procedure:
1: Remove all BLUETOOTH, WI-FI, and radio devices from the room.
2: Arrange phones in the pattern demonstrated in FIG. 6. Additionally, note that in FIG. 6, the lighter grid lines indicate 0.25 meter intervals while the thicker grid lines are 0.5 meters. Have the beacon in the north-eastern most corner of the grid. Phone 2 is the beacon. All other phones are receivers.
3: Turn the beacon on.
4: Turn every receiver on and start collecting RSSI pings on each phone.
5: Exit the room.
6: Return after 5 minutes.
7: Turn the beacon and receivers off if they are still on.
8: Log all of the data.

With a 1.28 decrease in the y-intercept of the best-fit line from test 7 to test 8 we further extend our inference from example 7 concluding that orientation within a setting doesn't affect RSSI.

EXAMPLE 9

Test 9: Outdoors

Overview:
Test 5 however the phones were on a tarp on asphalt outside.

Procedure:
1: Arrange phones in the pattern demonstrated in FIG. 6 outside on top of a tarp placed on top of asphalt. Additionally, note that in FIG. 6, the lighter grid lines indicate 0.25 meter intervals while the thicker grid lines are 0.5 meters. Have the beacon in the south-eastern most corner of the grid. Phone 2 is the beacon. All other phones are receivers.
2: Turn the beacon on.
3: Turn every receiver on and start collecting RSSI pings on each phone.
4: Move to where neither beacon nor the receivers are visible.
5: Return after 5 minutes.
6: Turn the beacon and receivers off if they are still on.
7: Log all of the data.

Conclusion:
With a 6.42 increase in the y-intercept from test 5 to test 9 it is evident that RSSI values are different inside versus outside which is consistent with the conclusion of test 5. Also similar to the conclusion of test 5 RSSI as a function of distance appears to remain linear with a similar slope.

EXAMPLE 10

Test 10: On Floor with Lights On, Loud Music and People

Overview:
Test 5 however lights were on, loud music was playing and three people were circling the grid making noise.

Procedure:
1: Turn on loud music.
2: Arrange phones in the pattern demonstrated in FIG. 6. Additionally, note that in FIG. 6, the lighter grid lines indicate 0.25 meter intervals while the thicker grid lines are 0.5 meters. Have the beacon in the south-eastern most corner of the grid. Phone 2 is the beacon. All other phones are receivers.
3: Turn the beacon on.
4: Turn every receiver on and start collecting RSSI pings on each phone.
5: Move around the grid on skateboards, scooters or some other loud wheeled vehicle.
6: Turn the beacon and receivers off if they are still on.
7: Log all of the data.

Conclusion:
Because the slope increases by only 0.82 and the y-intercept decreases by only 0.99 when compared to test 5 we conclude that noises, lights, and people in the room does not affect RSSI.

EXAMPLE 11

Test 11: Hanging Basis

Overview:
Test 5 however instead of on the ground the phones were hung from a PVC apparatus attached via binder clips. The phones were in the same position relative to other objects in the hangar, simply elevated approximately 5.5-6 feet.

Procedure
1: Remove all BLUETOOTH, WI-FI and radio devices from the room.
2: Elevate phones 5 feet off the ground using the hanging structure described in Precursor to Experiments Procedure step 2 in the pattern demonstrated in FIG. 6. Additionally, note that in FIG. 6, the lighter grid lines indicate 0.25 meter intervals while the thicker grid lines are 0.5 meters. Orient the grid so the beacon is in the South-East most corner of it. Phone 2 is the beacon. All other phones are receivers.
3: Turn the beacon on.
4: Turn every receiver on and start collecting RSSI pings on each phone.
5: Exit the room.
6: Return after 5 minutes.
7: Turn the beacon and receivers off if they are still on.
8: Log all of the data.

Conclusion:
In the air there remains a strong linear correlation between RSSI and distance. However, the y-intercept decreases by approximately 38 when compared to test 5. The slopes of the linear regressions for RSSI as a function of distance in the air vs on the ground remain similar with a difference of only 7.2.

Table 2 lists the average RSSI values for tests 6-11.

TABLE 2

| Phone ID | Distance From Beacon | Test 6 | Test 7 | Test 8 | Test 9 | Test 10 | Test 11 |
| --- | --- | --- | --- | --- | --- | --- | --- |
| 1 | 1 | | 76.49 | 80.34 | 79.18 | 82.94 | 80.22 | 55.36 |
| 3 | 1.414213562 | | | | | | |
| 4 | 2 | | | | | | |
| 5 | 1.802775638 | 88.36 | 96.23 | 91.51 | 99.5 | 90.64 | 62.97 |
| 6 | 1.802775638 | 85.79 | 88.15 | 91.09 | 94.85 | 89.08 | 59.12 |
| 7 | 1.5 | 83.32 | 86.54 | 82.86 | 90.15 | 88.02 | 55.11 |
| 8 | 0.707106781 | 85.61 | 87.32 | 83.42 | 91.18 | 85.87 | 48.36 |
| 9 | 2.061552813 | 87.91 | 86.92 | 94.9 | 97.61 | 88.3 | |
| 10 | 1.58113883 | 84.36 | 84.66 | 82.06 | 92.43 | 89.46 | 62.72 |
| 11 | 1 | 82.48 | 86.82 | 85.33 | 95.07 | 88.44 | 55.09 |
| 12 | 1.5 | | | | | | |

TABLE 2-continued

| Phone ID | Distance From Beacon | Test 6 | Test 7 | Test 8 | Test 9 | Test 10 | Test 11 |
|---|---|---|---|---|---|---|---|
| 13 | 0.5 | 69.25 | 71.56 | 72.03 | 73.24 | 73.51 | 42.79 |
| 14 | 2 | 90.34 | 89.67 | 90.31 | 93.03 | 84.89 | 64.84 |
| 15 | 1.58113883 | | | | | | |
| 17 | 2.5 | 90.02 | 92.22 | 88.43 | 101 | 90.52 | 67.6 |
| 18 | 1.118033989 | 81.27 | 89.16 | 90.08 | 91.25 | 87.12 | 50.88 |
| 19 | 0.5 | 79.11 | 80.95 | 82.21 | 86.6 | 86.09 | 47.88 |
| 20 | 1.118033989 | 82.72 | 84.16 | 83.88 | 85.38 | 83.12 | 52.63 |
| 21 | 2.061552813 | 90.8 | 95.19 | 89.08 | 102.03 | 88.22 | 67.21 |
| 22 | 2.5 | 87.41 | 87.97 | 91.78 | 96.25 | 85.96 | 69.71 |

EXAMPLE 12

Test 12: Hanging with Music

Overview:
Test 11 with loud music playing.
Procedure:
1: Remove all BLUETOOTH, WI-FI and radio devices from the room.
2: Elevate phones 5 feet off the ground using the hanging structure described in Precursor to Experiments Procedure step 2 in the pattern demonstrated in FIG. 6. Additionally, note that in FIG. 6, the lighter grid lines indicate 0.25 meter intervals while the thicker grid lines are 0.5 meters. Orient the grid so the beacon is in the South-East most corner of it. Phone 2 is the beacon. All other phones are receivers.
3: Turn on loud music adjacent to the beacon.
4: Turn the beacon on.
5: Turn every receiver on and start collecting RSSI pings on each phone.
6: Exit the room.
7: Return after 5 minutes.
8: Turn the beacon and receivers off if they are still on.
9: Log all of the data.

Conclusion:
Because the Y intercept decreases by only 1.39 when compared to test 5 and the slope changes by only 0.87 when compared to test 11 we conclude that the effects of music/noise on RSSI is negligible.

EXAMPLE 13

Test 13: Hanging with a Person Walking Around

Overview:
Test 11 with a person walking in circles around the grid.
Procedure:
1: Remove all BLUETOOTH, WI-FI and radio devices from the room.
2: Elevate phones 5 feet off the ground using the hanging structure described in Precursor to Experiments Procedure step 2 in the pattern demonstrated in FIG. 6. Additionally, note lines are 0.5 meters. Orient the grid so the beacon is in the South-East most corner of it. Phone 2 is the beacon. All other phones are receivers.
3: Turn the beacon on.
4: Turn every receiver on and start collecting RSSI pings on each phone.
5: Walk in circles around the grid at a medium pace.
6: Turn the beacon and receivers off if they are still on after 5 minutes.
7. Log all of the data.

Conclusion:
Because the y intercept decreased by 2.5 and the slope increased by only 1.2 for the best fit lines compared to test 11 we conclude that people near the phones has no effect on RSSI.

EXAMPLE 14

Test 14: Hanging with a Person in the Grid

Overview:
Test 11 with a person standing on the grid on the point C3.
Procedure:
1: Remove all BLUETOOTH, WI-FI and radio devices from the room.
2: Elevate phones 5 feet off the ground using the hanging structure described in Precursor to Experiments Procedure step 2 in the pattern demonstrated in FIG. 6. Additionally, note that in FIG. 6, the lighter grid lines indicate 0.25 meter intervals while the thicker grid lines are 0.5 meters. Orient the grid so the beacon is in the South-East most corner of it. Phone 2 is the beacon. All other phones are receivers.
3: Turn the beacon on.
4: Turn every receiver on and start collecting RSSI pings on each phone.,
5: Stand on the grid on the point C3 (depicted in FIG. 6)
6: Turn the beacon and receivers off if they are still on after 5 minutes
7: Log all of the data.

Conclusion:
Because the y intercept decreased by only 3.9 while the slope increased by only 1.2 when compared to the best fit line of test 11 we conclude that having human obstruction of the BLUETOOTH has negligible effects.

EXAMPLE 15

Test 15: Hanging with Texting

Overview:
Test 11 with a person standing directly behind the beacon texting on a separate phone.
Procedure:
1: Remove all BLUETOOTH, WI-FI and radio devices from the room with the exception of your phone.
2: Elevate phones 5 feet off the ground using the hanging structure described in Precursor to Experiments Procedure step 2 in the pattern demonstrated in FIG. 6. Additionally, note that in FIG. 6, the lighter grid lines indicate 0.25 meter intervals while the thicker grid lines are 0.5 meters. Orient the grid so the beacon is in the South-East most corner of it. Phone 2 is the beacon. All other phones are receivers.
3: Turn the beacon on.
4: Turn every receiver on and start collecting RSSI pings on each phone.
5: Stand directly behind the beacon.
6: Text and call people on your phone consistently for 5 minutes.
7: Turn the beacon and receivers off if they are still on.
8: Log all of the data.

Conclusion:
Because the y intercept decreased by only 4.2 while the slope increased by only 2.2 when compared to the best fit line of test 11 we conclude that having human stand behind the beacon and cell phone signals do not affect the RSSI values.

EXAMPLE 16

Test 16: Hanging: Beacon in SW Corner

Overview:
Test 11 with the beacon in the South West corner of the grid.
Procedure:
1: Remove all BLUETOOTH, WI-FI and radio devices from the room.
2: Elevate phones 5 feet off the ground using the hanging structure described in Precursor to Experiments Procedure step 2 in the pattern demonstrated in FIG. 6. Additionally, note that in FIG. 6, the lighter grid lines indicate 0.25 meter intervals while the thicker grid lines are 0.5 meters. Orient the grid so the beacon is in the South-West most corner of it. Phone 2 is the beacon. All other phones are receivers.
3: Turn the beacon on.
4: Turn every receiver on and start collecting RSSI pings on each phone.
5: Exit the room.
6: Return after 5 minutes.
7: Turn the beacon and receivers off if they are still on.
8: Log all of the data.
Conclusion:
While the slope decreased by 4.9 and the y intercept increased by 10.3 when compared to test 11 these changes are insignificant compared to the large average RSSI values of the two graphs ranging from 45-70.

EXAMPLE 17

Test 17: Hanging: Beacon in NW Corner

Overview:
Test 11 with the beacon in the North-West corner of the grid.
Procedure:
1: Remove all BLUETOOTH, WI-FI and radio devices from the room.
2: Elevate phones 5 feet off the ground using the hanging structure described in Precursor to Experiments Procedure step 2 in the pattern demonstrated in FIG. 6. Additionally, note that in FIG. 6, the lighter grid lines indicate 0.25 meter intervals while the thicker grid lines are 0.5 meters. Orient the grid so the beacon is in the North-West most corner of it. Phone 2 is the beacon. All other phones are receivers.
3: Turn the beacon on.
4: Turn every receiver on and start collecting RSSI pings on each phone.
5: Exit the room.
6: Return after 5 minutes.
7: Turn the beacon and receivers off if they are still on.
8: Log all of the data.
Conclusion:
While the slope decreased by 1.7 and the y intercept increased by 3.5 when compared to test 11 these changes are insignificant compared to the large average RSSI values of the two graphs ranging from 45-70.

EXAMPLE 18

Test 18: Hanging: Beacon in NE Corner

Overview:
Test 11 with the beacon in the North-East corner of the grid.
Procedure:
1: Remove a BLUETOOTH, WI-FI and radio devices from the room.
2: Elevate phones 5 feet off the ground using the hanging structure described in Precursor to Experiments Procedure step 2 in the pattern demonstrated in FIG. 6. Additionally, note that in FIG. 6, the lighter grid lines indicate 0.25 meter intervals while the thicker grid lines are 0.5 meters. Orient the grid so the beacon is the North-East most corner of it. Phone 2 is the beacon. All other phones are receivers.
3: Turn the beacon on.
4: Turn every receiver on and start collecting RSSI pings on each phone.
5: Exit the room.
6: Return after 5 minutes.
7: Turn the beacon and receivers off if they are still on.
8. Log all of the data.
Conclusion:
While the slope decreased by 3.1 and the y intercept increased by 6.2 when compared to test 11 these changes are insignificant compared to the large average RSSI values of the two graphs ranging from 45-70.

Table 3 lists the Max RSSI value record on each phone for experimental tests 11-18.

TABLE 3

| Phone ID | Distance From Beacon | Test 11 | Test 12 | Test 13 | Test 14 | Test 15 | Test 16 | Test 17 | Test 18 |
|---|---|---|---|---|---|---|---|---|---|
| 13 | 0.5 | 40 | 41 | 40 | 43 | 41 | 56 | 45 | 42 |
| 19 | 0.5 | 44 | 45 | 44 | 47 | 46 | 47 | 47 | 48 |
| 8 | 0.70710678 | 46 | 50 | 49 | 50 | 51 | 51 | 50 | 75 |
| 11 | 1 | 50 | 51 | 51 | 52 | 52 | 57 | 56 | 49 |
| 1 | 1 | 51 | 52 | 53 | 52 | 50 | 52 | 53 | 50 |
| 18 | 1.11803399 | 48 | 48 | 46 | 48 | 47 | 51 | 46 | 49 |
| 20 | 1.11803399 | 50 | 49 | 54 | 54 | 56 | 52 | 48 | 49 |
| 7 | 1.5 | 52 | 52 | 55 | 54 | 55 | 54 | 55 | 53 |
| 10 | 1.58113883 | 60 | 59 | 58 | 54 | 57 | 57 | 54 | 55 |
| 5 | 1.80277564 | 57 | 58 | 60 | 63 | 59 | 62 | 64 | 58 |
| 6 | 1.80277564 | 54 | 54 | 56 | 57 | 58 | 62 | 59 | 58 |
| 21 | 2.06155281 | 63 | 57 | 55 | 55 | 56 | 59 | 61 | 64 |
| 14 | 2 | 59 | 61 | 56 | 57 | 54 | 65 | 58 | 58 |
| 17 | 2.5 | 63 | 62 | 60 | 61 | 61 | 61 | 62 | 63 |
| 22 | 2.5 | 66 | 65 | 63 | 63 | 66 | 61 | 59 | 60 |

Table 4 lists the minimum RSSI value recorded on each phone for tests 11-18.

TABLE 4

| Phone ID | Distance From Beacon | Test 11 | Test 12 | Test 13 | Test 14 | Test 15 | Test 16 | Test 17 | Test 18 |
|---|---|---|---|---|---|---|---|---|---|
| 13 | 0.5 | 40 | 41 | 40 | 43 | 41 | 56 | 45 | 42 |
| 19 | 0.5 | 44 | 45 | 44 | 47 | 46 | 47 | 47 | 48 |
| 8 | 0.70710678 | 46 | 50 | 49 | 50 | 51 | 51 | 50 | 75 |
| 11 | 1 | 50 | 51 | 51 | 52 | 52 | 57 | 56 | 49 |
| 1 | 1 | 51 | 52 | 53 | 52 | 50 | 52 | 53 | 50 |
| 18 | 1.11803399 | 48 | 48 | 46 | 48 | 47 | 51 | 46 | 49 |
| 20 | 1.11803399 | 50 | 49 | 54 | 54 | 56 | 52 | 48 | 49 |
| 7 | 1.5 | 52 | 52 | 55 | 54 | 55 | 54 | 55 | 53 |
| 10 | 1.58113883 | 60 | 59 | 58 | 54 | 57 | 57 | 54 | 55 |
| 5 | 1.80277564 | 57 | 58 | 60 | 63 | 59 | 62 | 64 | 58 |
| 6 | 1.80277564 | 54 | 54 | 56 | 57 | 58 | 62 | 59 | 58 |
| 21 | 2.06155281 | 63 | 57 | 55 | 55 | 56 | 59 | 61 | 64 |
| 14 | 2 | 59 | 61 | 56 | 57 | 54 | 65 | 58 | 58 |
| 17 | 2.5 | 63 | 62 | 60 | 61 | 61 | 61 | 62 | 63 |
| 22 | 2.5 | 66 | 65 | 63 | 63 | 66 | 61 | 59 | 60 |

Table 5 lists the range between the minimum and maximum values of RSSI in tests 11-18.

TABLE 5

| Phone ID | Distance From Beacon | Test 11 | Test 12 | Test 13 | Test 14 | Test 15 | Test 16 | Test 17 | Test 18 |
|---|---|---|---|---|---|---|---|---|---|
| 13 | 0.5 | 6 | 5 | 6 | 4 | 5 | 11 | 4 | 4 |
| 19 | 0.5 | 6 | 5 | 6 | 4 | 6 | 9 | 7 | 6 |
| 8 | 0.70710678 | 6 | 4 | 3 | 5 | 6 | 6 | 6 | 13 |
| 1 | 1 | 9 | 7 | 10 | 9 | 10 | 8 | 7 | 6 |
| 11 | 1 | 11 | 12 | 12 | 16 | 13 | 4 | 35 | 32 |
| 18 | 1.11803399 | 6 | 6 | 9 | 9 | 8 | 7 | 8 | 7 |
| 20 | 1.11803399 | 4 | 8 | 8 | 18 | 11 | 6 | 7 | 6 |
| 7 | 1.5 | 7 | 10 | 12 | 10 | 10 | 16 | 8 | 10 |
| 10 | 1.58113883 | 10 | 12 | 8 | 13 | 7 | 13 | 12 | 12 |
| 5 | 1.80277564 | 18 | 25 | 28 | 30 | 25 | 13 | 9 | 16 |
| 6 | 1.80277564 | 19 | 12 | 20 | 13 | 13 | 7 | 20 | 17 |
| 21 | 2.06155281 | 13 | 10 | 15 | 13 | 12 | 8 | 13 | 12 |
| 14 | 2 | 14 | 17 | 14 | 27 | 7 | 21 | 13 | 6 |
| 17 | 2.5 | 21 | 10 | 14 | 34 | 15 | 19 | 18 | 17 |
| 22 | 2.5 | 14 | 33 | 21 | 17 | 17 | 11 | 10 | 11 |

Table 6 lists the average RSSI values for tests 11-18.

TABLE 6

| Phone ID | Distance From Beacon | Test 12 | Test 13 | Test 14 | Test 15 | Test 16 | Test 17 | Test 18 |
|---|---|---|---|---|---|---|---|---|
| 1 | 1 | 55.56 | 56.71 | 57.54 | 56.27 | 55.43 | 55.57 | 53.29 |
| 3 | 1.414213562 | | | | | | | |
| 4 | 2 | | | | | | | |
| 5 | 1.802775638 | 65.98 | 68.86 | 70.54 | 67.41 | 67.51 | 68.02 | 65.41 |
| 6 | 1.802775638 | 58.57 | 62.91 | 62.1 | 62.55 | 66.08 | 67.39 | 65.61 |
| 7 | 1.5 | 55.77 | 59.57 | 59.51 | 60.06 | 62.08 | 58.74 | 56.58 |
| 8 | 0.707106781 | 51.83 | 50.75 | 52.07 | 52.65 | 53.74 | 53.7 | 53.55 |
| 9 | 2.061552813 | | | | | | | |
| 10 | 1.58113883 | 62.16 | 61.94 | 62.08 | 60.24 | 63.37 | 58.06 | 59.04 |
| 11 | 1 | 55.05 | 55.48 | 58.03 | 57.08 | 58.87 | 66.81 | 60.35 |
| 12 | 1.5 | | | | | | | |
| 13 | 0.5 | 43.26 | 42.81 | 44.82 | 42.99 | 60.81 | 47.07 | 44.18 |
| 14 | 2 | 65.47 | 62.29 | 65.68 | 57.99 | 70.64 | 62.61 | 61.1 |
| 15 | 1.58113883 | | | | | | | |
| 17 | 2.5 | 66.65 | 66.04 | 70.41 | 67.89 | 65.88 | 68.79 | 70.81 |
| 18 | 1.118033989 | 50.74 | 50.89 | 51.51 | 51.51 | 53.69 | 49.77 | 52.08 |
| 19 | 0.5 | 47.39 | 47.37 | 49.04 | 49.11 | 52.46 | 51.12 | 50.99 |
| 20 | 1.118033989 | 53.87 | 57.84 | 59.69 | 61.81 | 54.52 | 50.76 | 51.69 |
| 21 | 2.061552813 | 60.99 | 60.8 | 60.81 | 60.58 | 62.53 | 65.22 | 68.66 |
| 22 | 2.5 | 70.9 | 69.42 | 69.25 | 70.16 | 64.79 | 63.09 | 64.14 |

EXAMPLE 19

Test 19: Hanging Outside With Beacon in NE Corner

Overview:

Test 11 located outside with WI-FI and BLUETOOTH devices running but at a large distance from devices (20 yards).

Procedure:
1: Elevate phones 5.5 feet off the ground using the hanging structure described in Precursor to Experiments Procedure step 2 in the pattern demonstrated in FIG. 6. Place the hanging apparatus outside. Additionally, note that in FIG. 6, the lighter grid lines indicate 0.25 meter intervals while the thicker grid lines are 0.5 meters. Orient the grid so the beacon is in the North-East most corner of it. All phones are beacons and receivers.
2: Turn on phones and start collecting RSSI pings on each phone.
3: Move to 20 yards from beacons and receivers.
4: Return after 5 minutes.
5: Turn the beacon and receivers off if they are still on.
6: Log all of the data.
7: Send raw data (Table 7) through max filtered algorithm as shown below in max filtered pseudocode to output edges (Table 12).
8: Input edges into D3.js force directed algorithm and collect phone (X,Y) output as shown in Table 13.
9: Input (X,Y) values into a scaling algorithm as shown in Max Filter Pseudocode part IV
10: Compare accuracy between test layout and scaled output of force directed drawings as shown in Table 18.

Conclusion:

Based upon Table 18, the force directed scaled output has a 100% sub meter accuracy as well as nearly perfect sequencing accuracy.

Table 7 lists an example Test 19 RSSI Values Hash for signals from Phone 11 (ex. First Pairing Phone 10 receiving RSSI from Phone 11, etc.).

TABLE 7

'10': [−58, −58, −76, −63, −58, −63, −64, −58, −59, −70, −65, −61, −60, −66, −62, −75, −62, −67, −58, −64, −64, −65, −60, −63, −60, −61, −60, −59, −57, −59, −63, −72, −70, −62, −62, −62, −58, −66, −64, −63, −56, −62, −68, −63, −65, −59, −60, −66, −64, −57,

'13': [−50, −68, −54, −52, −60, −52, −57, −52, −52, −53, −58, −49, −55, −57, −50, −51, −65, −52, −54, −62, −55, −50, −52, −66, −53, −60, −59, −62, −57, −59, −55, −59, −58, −55, −56, −51, −61, −54, −60, −58, −55, −50, −54, −59, −51, −55, −54, −52, −53, −51],

'12': [−51, −50, −49, −55, −52, −54, −57, −49, −49, −43, −46, −50, −47, −50, −59, −57, −49, −50, −61, −50, −52, −60, −56, −57, −47, −54, −63, −46, −51, −50, −45, −49, −60, −51, −53, −52, −49, −50, −43, −44, −47, −56, −55, −52, −50, −52, −52, −61, −50, −52, −49, −59, −59, −53, −46, −45, −50, −50],

'15': [−62, −59, −67, −56, −56, −52, −53, −51, −58, −59, −58, −52, −54, −51, −55, −56, −53, −54, −51, −57, −51, −55, −52, −52, −52, −55, −53, −51, −53, −68, −50, −54, −55, −54, −57, −51, −51, −50, −52, −50, −50, −53, −57, −55, −60, −48, −55, −55, −54, −57, −56, −58, −52, −68, −54, −54, −60],

'21': [−62, −55, −56, −52, −53, −54, −70, −55, −54, −50, −56, −55, −54, −52, −52, −54, −58, −54, −64, −53, −55, −58, −55, −55, −54, −55, −50, −57, −56, −57, −54, −53, −56, −55, −54, −53, −55, −62, −58, −50, −54, −50, −71, −58, −53, −53],

'17': [−61, −59, −60, −60, −66, −56, −59, −55, −55, −59, −62, −61, −61, −63, −62, −65, −58, −66, −63, −59, −63, −64, −58, −67, −56, −61, −64, −58, −64, −63, −62, −64, −65, −66, −72, −59, −64, −58, −58, −60, −57, −60, −63, −59, −65, −60, −60, −66, −64, −56, −62, −60, −67, −59, −59, −63, −66],

'19': [−52, −50, −51, −65, −46, −46, −48, −50, −51, −52, −50, −48, −54, −48, −52, −68, −45, −58, −52, −44, −44, −51, −49, −62, −45, −48, −54, −47, −50, −55, −57, −54, −50, −52, −58, −55, −48, −49, −52, −47, −47, −44, −49, −52, −51, −50, −57, −44, −52, −53, −50],

'18': [−52, −53, −46, −48, −48, −51, −49, −51, −47, −49, −48, −50, −48, −48, −49, −45, −50, −52, −46, −57, −47, −52, −45, −48, −50, −46, −50, −45, −44, −50, −49, −54, −48, −46, −49, −48, −44, −65, −49, −50, −54, −50, −46, −49, −46, −49, −51, −47, −46, −44, −51, −65, −52, −46],

'22': [−83, −64, −68, −62, −60, −63, −60, −59, −67, −58, −63, −59, −60, −60, −63, −64, −60, −66, −62, −58, −74, −60, −65, −64, −59, −55, −68, −58, −68, −68, −59, −65, −60, −66, −62, −62, −58, −60, −60, −61, −60, −63, −69, −60, −60, −57, −65, −62, −56, −61, −66, −64, −60, −60, −60, −58, −64],

'1': [−58, −52, −54, −66, −54, −62, −56, −55, −63, −54, −57, −54, −56, −54, −56, −59, −63, −52, −58, −50, −52, −63, −70, −54, −55, −54, −62, −57, −56, −55, −51, −65, −64, −57, −59, −59, −60, −51, −64, −54, −52, −57, −58, −55, −59, −52, −60, −54, −63, −55, −64],

'3': [−57, −59, −55, −54, −56, −66, −66, −56, −63, −63, −68, −61, −56, −64, −65, −62, −61, −77, −60, −65, −62, −57, −59, −59, −52, −62, −56, −64, −62, −58, −60, −63, −56, −59, −57, −53, −55, −58, −54, −63, −58, −61, −62, −60, −62, −63, −60],

'2': [−52, −56, −54, −54, −59, −60, −59, −52, −60, −56, −68, −68, −64, −52, −59, −58, −64, −58, −64, −63, −64, −57, −59, −60, −59, −51, −54, −52, −52, −56, −60, −58, −60, −59, −58, −58, −60, −54, −58, −53, −54, −59, −66, −66, −64, −54, −66, −53, −57],

'5': [−56, −63, −58, −62, −64, −55, −56, −60, −53, −54, −65, −62, −60, −60, −55, −55, −63, −53, −55, −53, −58, −56, −58, −55, −53, −55, −53, −55, −58, −74, −53, −58, −60, −55, −59, −56, −63, −52, −54, −56, −55, −58, −53, −50, −54, −57, −60, −58, −55, −50],

'4': [−60, −55, −55, −57, −53, −54, −61, −57, −53, −56, −53, −60, −56, −58, −58, −60, −59, −61, −57, −61, −54, −52, −58, −59, −59, −58, −55, −62, −66, −56, −59, −56, −58, −58, −61, −50, −52, −62, −50, −53, −58, −61, −59, −56, −58, −59, −61, −54, −60, −53, −60, −53, −55, −56, −58],

'7': [−61, −72, −69, −68, −72, −62, −60, −57, −61, −64, −62, −65, −58, −79, −62, −66, −62, −72, −70, −58, −61, −66, −58, −66, −70, −64, −72, −59, −62, −59, −66, −66, −70, −58, −57, −67, −68, −62, −66, −61, −62, −73, −61, −65, −58, −60, −71, −61, −70, −79, −83, −73, −57],

'6': [−58, −70, −58, −66, −68, −58, −60, −54, −66, −56, −64, −60, −60, −76, −62, −59, −58, −64, −58, −60, −58, −57, −60, −57, −61, −57, −57, −56, −70, −57, −57, −54, −61, −56, −67, −56, −57, −55, −55, −58, −60, −60, −54, −58, −64],

'9': [−65, −80, −65, −62, −61, −65, −60, −73, −75, −63, −65, −62, −76, −72, −69, −73, −74, −70, −74, −70, −64, −63, −62, −67, −68, −66, −60, −63, −66, −62, −74, −58, −68, −65, −70, −77, −71, −92, −70, −65, −64, −63, −63, −62, −59, −66, −60, −59, −68, −68, −67, −63, −82],

'20': [−48, −53, −54, −50, −58, −54, −52, −73, −52, −67, −60, −47, −62, −52, −56, −57, −59, −49, −51, −50, −62, −52, −52, −61, −58, −53, −56, −61, −60, −55, −55, −50, −52, −48, −55, −54, −58, −51, −53, −61, −48, −54, −61, −56, −64, −62, −50],

TABLE 7-continued

'8': [−55, −50, −49, −55, −51, −50, −49, −52, −57, −55, −52, −50, −56, −57, −50, −50, −52, −51, −54, −57, −52, −50, −50, −52, −50, −51, −46, −58, −53, −54, −55, −52, −56, −52, −49, −51, −57, −48, −49, −59, −57, −59, −51, −57, −52, −53, −50],
'14': [−64, −70, −62, −56, −61, −56, −58, −69, −69, −68, −69, −60, −56, −67, −62, −63, −56, −57, −57, −56, −54, −60, −61, −58, −55, −66, −57, −59, −63, −55, −57, −62, −56, −55, −53, −54, −57, −54, −64, −82, −71, −57]
}, . . .

Figure 7:
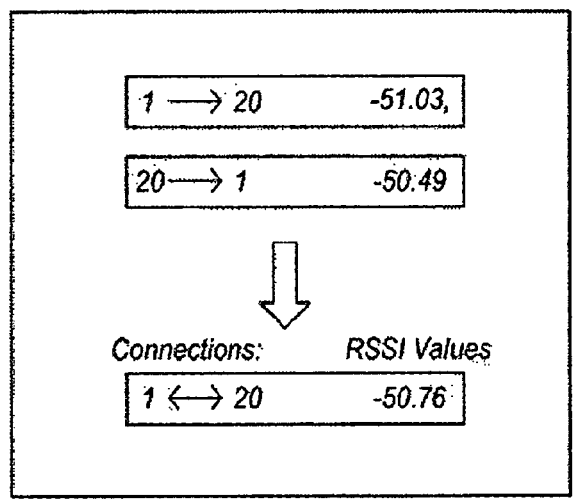
FIG. 7 illustrates an exemplary diagram for Determining Phone to Phone RSSI Connection Strength with Kalman Filter in Test 19 according to an embodiment.

FIG. 7 illustrates an exemplary diagram for Determining Phone to Phone RSSI Connection Strength with Kalman Filter in Test 19 according to an embodiment.

Referring to FIG. 7, the RSSI value for the connection between node 1 to node 20 may be −51.03, and the RSSI value for the connection between node 20 to node 1 may be −50.76. Here, the RSSI value may be normalized to be −50.76 for a determination for both connections (the RSSI value (and distance) between nodes 1 and 20 may be considered the same).

Table 8 lists the Kalman Filtered RSSI Value (One Direction, Other Direction, Average of Both Directions) for Test 19.

TABLE 8

{('1', '20'): [−51.031945442416912, −50.492785341942813, −50.762365392179859], ('15', '14'):
[−61.041343047472253, −62.431630996425206, −61.736487021948733], ('3', '15'):
[−55.141864758743552, −55.318173656446987, −55.230019207595269], ('22', '6'):
[−57.970342741009731, −56.424317043870936, −57.197329892440337], ('13', '21'):
[−65.165977861845377, −66.206290836147474, −65.686134348996433], ('18', '22'):
[−59.867056363370949, −60.393840621710012, −60.130448492540481], ('22', '21'):
[−61.539477020660698, −63.400721008912086, −62.470099014786392], ('11', '10'):
[−61.896593541363465, −61.472617420318137, −61.684605480840801], ('4', '5'):
[−57.310183361538726, −58.717868956115325, −58.014026158827022], ('11', '9'):
[−66.180667897587071, −65.60271584490512, −65.891691871246096], ('7', '1'):
[−53.990237319372895, −55.00672416695555, −54.498480743164222], ('21', '17'):
[−53.393698291954387, −53.540904337241919, −53.467301314598153], ('10', '19'):
[−58.312460541111193, −59.405345352520605, −58.858902946815903], ('6', '15'):
[−54.828833894933275, −53.70385625622351, −54.266345075578393], ('6', '5'):
[−54.576175417763146, −55.03014094404179, −54.803158180902471], ('20', '13'):
[−54.939117020728538, −51.788870514032965, −53.363993767380748], ('14', '18'):
[−60.686613608097275, −62.307281708622277, −61.496947658359773], ('1', '14'):
[−55.277174327419246, −56.885427349849991, −56.081300838634618], ('22', '19'):
[−64.318976599506513, −66.228332219914094, −65.273654409710304], ('2', '1'):
[−57.073510106217789, −59.195726302430728, −58.134618204324255], ('19', '15'):
[−53.992898167055387, −52.868018486141324, −53.430458326598355], ('9', '22'):
[−53.834939935637024, −54.760464709266294, −54.297702322451656], ('14', '2'):
[−60.942491018364713, −59.882963487933623, −60.412727253149171], ('4', '1'):
[−62.972105938748555, −62.369150192300786, −62.670628065524667], ('5', '14'):
[−63.974830226297861, −61.165603423638309, −62.570216824968085], ('21', '19'):
[−64.137258801545102, −63.401912019206868, −63.769585410375981], ('7', '5'):
[−65.059965496011856, −64.588571276055774, −64.824268386033822], ('2', '3'):
[−57.397857362781885, −56.776468144532494, −57.087162753657189], ('20', '18'):
[−53.183948574552154, −54.06019719800539, −53.622072886278772], ('3', '8'):
[−52.054629848100532, −53.774216182494726, −52.914423015297629], ('17', '10'):
[−61.944903980018658, −63.613747899124789, −62.77932593957172], ('22', '12'):
[−66.2979913392778, −64.863755358278851, −65.580873348778326], ('10', '21'):
[−61.2617531261821, −60.86213507967846, −61.061944102930283], ('7', '4'):
[−68.086156924374166, −66.200089638886894, −67.143123281630523], ('17', '20'):
[−59.50677524273717, −60.948898410594232, −60.227836826665701], ('14', '20'):
[−54.635277363359599, −55.667351482292815, −55.151314422826204], ('3', '7'):
[−56.880504444564394, −55.441652648073074, −56.161078546318734], ('6', '1'):
[−56.693435202722164, −56.794851372753556, −56.744143287737856], ('2', '15'):
[−61.473864674510658, −61.129672526515471, −61.301768600513064], ('7', '17'):
[−68.446484821514389, −66.826336618463372, −67.636410719988874], ('9', '7'):
[−59.00549451763159, −57.576717046207882, −58.29110578191974], ('2', '5'):
[−63.919251216783678, −65.056460059101795, −64.487855637942744], ('4', '10'):
[−59.369514462129651, −60.675010151703084, −60.022262306916367], ('8', '17'):
[−60.390485930310554, −58.203760202129317, −59.297123066219939], ('22', '8'):
[−59.740081276318328, −59.019688185258993, −59.37988473078866], ('1', '18'):
[−57.181619154750038, −56.903099178906153, −57.042359166828092], ('3', '22'):
[−61.187767430256862, −60.789270677950377, −60.98851905410362], ('21', '4'):
[−49.617283833160315, −48.767755145744914, −49.192519489452614], ('2', '7'):
[−61.457819270457613, −62.151987651328788, −61.8049034608932], ('8', '4'):
[−63.126119400236156, −62.492825001181849, −62.809472200709003], ('3', '4'):
[−58.860138629775875, −58.507929582669064, −58.68403410622247], ('10', '8'):
[−56.179505355281066, −56.860441057973837, −56.519973206627455], ('6', '18'):
[−57.530888678221778, −57.754056385250195, −57.64247253173599], ('21', '5'):
[−53.17030515080544, −53.464301899317263, −53.317303525061348], ('1', '22'):
[−58.963259700841952, −58.910911513935176, −58.937085607388568], ('21', '15'):
[−48.901671601957943, −50.438444067535642, −49.670057834746792], ('3', '13'):
[−55.719270839378005, −53.844567462890879, −54.781919151134446], ('2', '9'):
[−63.527136425877799, −64.21963076630071, −63.873383596089255], ('1', '11'):

TABLE 8-continued

[−56.754321865715433, −56.201962251841259, −56.478142058778346], ('17', '6'):
[−63.926855905974307, −64.431523995072197, −64.179189950523252], ('13', '9'):
[−61.50033432514882, −62.070973640855371, −61.785653983002092], ('11', '12'):
[−50.836213852380872, −50.830029815757278, −50.833121834069075], ('6', '21'):
[−56.406590862321991, −56.501457643973168, −56.45402425314758], ('13', '18'):
[−56.620042920793864, −57.008847226562843, −56.814445073678357], ('17', '5'):
[−59.833090828230908, −59.400169953571663, −59.616630390901285], ('13', '8'):
[−51.365168987758871, −51.589401283762811, −51.477285135760837], ('4', '9'):
[−67.354293999098857, −68.814218640763826, −68.084256319931342], ('19', '8'):
[−50.974562369390547, −50.254231198747895, −50.614396784069221], ('11', '5'):
[−57.25709438807182, −58.049064276481772, −57.653079332276796], ('9', '19'):
[−68.286387172021747, −67.654670145340319, −67.970528658681033], ('12', '18'):
[−52.156080539377896, −52.931857338004249, −52.543968938691073], ('14', '12'):
[−65.094436902448379, −63.638950029635808, −64.366693466042094], ('20', '22'):
[−60.658463642434555, −62.528960635457466, −61.59371213894601], ('21', '1'):
[−62.841896551226405, −63.194316198626531, −63.018106374926468], ('13', '6'):
[−55.409396522552584, −55.079922457151589, −55.244659489852083], ('13', '11'):
[−53.693749514900972, −54.793219871412781, −54.243484693156873], ('19', '17'):
[−66.568355050383587, −65.364464244293316, −65.966409647338452], ('2', '10'):
[−60.686688767023817, −61.088316219477363, −60.887502493250594], ('4', '6'):
[−63.11700468316473, −62.486984780026916, −62.801994731595826], ('4', '17'):
[−53.225500538505642, −54.002674122326091, −53.61408733041587], ('8', '12'):
[−54.385513354459306, −54.381778915451733, −54.383646134955519], ('6', '2'):
[−63.245787673615986, −64.274495435618093, −63.760141554617036], ('22', '10'):
[−55.424153164184403, −55.63465054408627, −55.5294018541335337], ('19', '5'):
[−57.165632370796573, −56.100636490084497, −56.633134430440535], ('22', '7'):
[−56.068292978429078, −56.267160690788018, −56.167726834608544], ('2', '17'):
[−67.655322199399151, −65.338094287797617, −66.496708243598391], ('7', '15'):
[−63.723967007298654, −64.397100813778351, −64.06053391053851], ('9', '18'):
[−62.325559914883925, −62.577612042151813, −62.451585978517869], ('8', '15'):
[−54.162237912835081, −55.67383317946377, −54.918035546149426], ('9', '1'):
[−57.901710715383594, −58.64117090704471, −58.271440811214148], ('14', '19'):
[−63.717415266670024, −64.410504027626402, −64.063959647148209], ('3', '18'):
[−51.298991304336717, −50.659373423347652, −50.979182363842185], ('11', '20'):
[−54.00651324234547, −52.871883785456866, −53.439198513901168], ('18', '2'):
[−56.309749629273725, −53.948736111712464, −55.129242870493094], ('4', '2'):
[−59.710241021801487, −62.231964996744559, −60.971103009273023], ('13', '1'):
[−50.246684386920066, −51.716888939689824, −50.981786663304945], ('10', '9'):
[−52.408701677151491, −53.635596980492792, −53.022149328822138], ('13', '22'):
[−62.52149984526153, −62.86886584857448, −62.695182846918001], ('3', '20'):
[−49.650757585552704, −48.953373735850477, −49.302065660701587], ('22', '4'):
[−71.03242192632672, −68.84728240261316, −69.93985216446994], ('11', '2'):
[−56.929624519263847, −55.701890066615221, −56.315757292939537], ('4', '19'):
[−59.362794535021628, −62.704779671923561, −61.033787104472591], ('21', '8'):
[−57.9008267083722, −57.247825696473491, −57.574326202422846], ('15', '10'):
[−55.42230130389261, −54.243148078024014, −54.832724690958315], ('3', '11'):
[−59.154888267653497, −59.176829619796585, −59.165858943725041], ('12', '13'):
[−62.497997217332191, −63.238848352502181, −62.868422784917186], ('8', '2'):
[−53.264524562065041, −53.195940126996327, −53.230232344530684], ('3', '9'):
[−57.435118769921232, −57.879635031171567, −57.657376900546396], ('6', '7'):
[−59.229849565444553, −58.700057622260204, −58.964953593852378], ('21', '9'):
[−63.56983671192063, −63.062001269727617, −63.315918990824123], ('11', '14'):
[−60.299656937924702, −58.511450955495256, −59.405553946709979], ('18', '11'):
[−49.172171879689017, −48.57257576590213, −48.872373822795574], ('6', '11'):
[−61.472555365020661, −60.198984417530589, −60.835769891275625], ('7', '19'):
[−62.589681640485828, −63.796115598989573, −63.192898619737704], ('17', '3'):
[−62.93865788530443, −63.237204283838942, −63.087931084571686], ('19', '2'):
[−51.757944277538058, −50.919148396309545, −51.338546336923798], ('17', '13'):
[−65.104720118176317, −66.542654690417621, −65.823687404296976], ('14', '10'):
[−55.110042908845948, −54.422527373866025, −54.766285141355986], ('12', '21'):
[−51.632327826550721, −50.705317107784538, −51.168822467167629], ('3', '6'):
[−53.164225714977526, −51.120000045115646, −52.142112880046582], ('7', '21'):
[−61.586027875081777, −60.742942081277583, −61.164484978547677], ('10', '3'):
[−53.20917970969009, −54.667210212403404, −53.938194961046747], ('2', '12'):
[−59.447064747650316, −60.235662387283753, −59.841363567467035], ('3', '5'):
[−52.379651118374213, −51.962037973125632, −52.170844545749922], ('7', '12'):
[−64.145308560123624, −64.06169691735559, −64.1035027183430607], ('5', '10'):
[−54.725091886530407, −54.853956054569736, −54.789523970550071], ('9', '15'):
[−65.146793867868169, −66.293249255421131, −65.720021561644643], ('4', '15'):
[−52.322381851949423, −54.956856136321427, −53.639618994135425], ('17', '14'):
[−68.530946239143006, −67.947643783511083, −68.239295011327044], ('10', '1'):
[−55.033185479575273, −53.391675051680593, −54.21243026562793], ('11', '8'):
[−51.697474826546269, −51.256203031211186, −51.476838928878728], ('21', '2'):
[−63.419130411843128, −63.494952173531715, −63.457041292687421], ('20', '4'):
[−61.084348277222411, −61.11532631098202, −61.099837294102215], ('15', '5'):
[−50.425724011824087, −49.583866343640096, −50.004795177732092], ('11', '22'):
[−62.783819587859512, −63.242589811539823, −63.013204699699671], ('20', '9'):
[−57.353065202281726, −57.916626686322488, −57.634845944302107], ('21', '20'):
[−60.200238123685352, −60.244668385509591, −60.222453254597468], ('19', '13'):
[−53.768595311807395, −53.071320185504959, −53.419957748656174], ('6', '14'):

TABLE 8-continued

[−54.736052442187862, −53.425764503989107, −54.080908473088485], ('14', '3'):
[−56.024696858182892, −55.902490460928568, −55.963593659555727], ('14', '8'):
[−62.680536791838982, −62.631010226969146, −62.655773509404064], ('15', '12'):
[−50.543325442339217, −48.960436017965293, −49.751880730152251], ('1', '5'):
[−60.888103207956391, −60.367814874139285, −60.627959041047838], ('20', '10'):
[−49.515305940208691, −49.387993539753687, −49.451649739981193], ('11', '7'):
[−63.684398200617352, −64.559447906773926, −64.121923053695639], ('17', '18'):
[−57.447302216305864, −58.016960035214211, −57.732131125760034], ('1', '15'):
[−61.05516744753016, −62.705684597191407, −61.88042602236078], ('13', '14'):
[−59.031056533248098, −56.901675994094305, −57.966366263671205], ('21', '14'):
[−64.739971105047573, −65.419869282260265, −65.079920193653919], ('10', '13'):
[−54.299539949659355, −54.712643649689198, −54.50609179967428], ('19', '12'):
[−57.548207758835666, −56.546636838667972, −57.047422298751819], ('20', '2'):
[−55.282066013764002, −55.786319691160308, −55.534192852462155], ('9', '6'):
[−56.655356976250872, −56.257071095255334, −56.456214035753106], ('21', '18'):
[−56.181684623712258, −57.4383844873642 74, −56.810034555538266], ('20', '15'):
[−52.849621783177355, −53.256765105934058, −53.053193444555703], ('20', '19'):
[−57.371523896643914, −58.378318109282191, −57.874921002963049], ('17', '11'):
[−58.454033286557845, −60.113852539978993, −59.283942913268419], ('17', '9'):
[−68.847052818123871, −67.203561172149932, −68.025306995136901], ('22', '5'):
[−64.379478227396547, −62.863783354057006, −63.621630790726776], ('7', '10'):
[−53.851084481947112, −53.411908057343219, −53.631496269645169], ('5', '12'):
[−57.542709218769865, −56.853554760885018, −57.198131989827445], ('4', '13'):
[−63.299048936269138, −64.100520712989166, −63.699784824629148], ('22', '14'):
[−47.554548223762573, −48.309118251320974, −47.931833237541774], ('1', '19'):
[−57.277680070166113, −57.7148519609147, −57.496266015540407], ('20', '8'):
[−48.722132559390602, −49.015827780322503, −48.868980169856556], ('11', '4'):
[−56.351036996599625, −55.067104402699655, −55.709070699649644], ('15', '17'):
[−55.634691195816622, −55.592641933418669, −55.613666564617645], ('3', '1'):
[−60.062313923835589, −60.869353673266694, −60.465833798551145], ('12', '10'):
[−62.310567201353614, −61.485174733992899, −61.897870967673256], ('12', '1'):
[−63.654529649957873, −66.352133835888637, −65.003331742923251], ('18', '7'):
[−59.314775576111707, −60.159895056910734, −59.737335316511221], ('8', '6'):
[−54.983775084118669, −53.552982025070115, −54.268378554594392], ('5', '9'):
[−61.494902731528285, −61.427918990616824, −61.461410861072551], ('12', '3'):
[−56.486416612709107, −55.882361407998317, −56.184389010353712], ('12', '17'):
[−56.877149545187336, −55.490933862310136, −56.184041703748733], ('17', '1'):
[−66.232563690830247, −67.684560051159991, −66.958561870995112], ('18', '5'):
[−54.549524164347488, −53.513712676837969, −54.031618420592729], ('12', '4'):
[−49.73611764007979, −48.467493914726987, −49.101805777403385], ('18', '15'):
[−48.07782417457296, −49.252433716205552, −48.665128945389256], ('9', '8'):
[−60.76261053384912, −60.568963783575661, −60.665787158712391], ('12', '6'):
[−60.256544124783254, −60.663231220460425, −60.459887672621839], ('1', '8'):
[−58.039370519221258, −56.233708833261865, −57.136539676241561], ('10', '18'):
[−53.063040833127559, −53.245295456043621, −53.15416814458559], ('13', '7'):
[−59.31995203795455, −58.623026130010082, −58.97148908398232], ('3', '19'):
[−56.660687173859799, −55.999350700637422, −56.33001893724861], ('12', '9'):
[−63.806748249427216, −63.359872650552823, −63.583310449990023], ('20', '12'):
[−53.079696346792439, −53.478528110530014, −53.279112228661226], ('2', '22'):
[−63.853127348147346, −66.916565592881255, −65.384846470514304], ('6', '19'):
[−61.324571683531957, −63.537851581509557, −62.431211632520757], ('13', '5'):
[−60.860758625988794, −62.253566470492174, −61.557162548240484], ('4', '18'):
[−51.808137140363961, −53.517578467779551, −52.662857804071756], ('15', '11'):
[−55.277427226536481, −54.986030537995624, −55.131728882266053], ('20', '7'):
[−53.914222834397137, −53.892091603510266, −53.903157218953702], ('6', '20'):
[−52.850453466323017, −51.669107969392591, −52.259780717857808], ('5', '8'):
[−54.063321594225776, −54.242292296518023, −54.1528069453719], ('19', '11'):
[−52.754167792531064, −50.479509992078768, −51.616838892304912], ('6', '10'):
[−49.457358698275669, −49.684828325281835, −49.571093511778756], ('20', '5'):
[−60.281354901692644, −59.60179643010121, −59.941575665896927], ('13', '2'):
[−48.353721437657477, −48.403099173558168, −48.378410305607822], ('21', '11'):
[−54.269993215895724, −54.874774659120028, −54.57238393750788], ('14', '4'):
[−63.736211165860453, −63.944364997790636, −63.840288081825548], ('22', '17'):
[−72.061576013981721, −69.156652375935025, −70.609911419495838], ('7', '14'):
[−50.433444369883752, −50.580072080591911, −50.506758225237832], ('14', '9'):
[−50.489537114457647, −49.803861575733485, −50.146699345059571], ('15', '22'):
[−63.969829934096843, −66.16105430340906, −65.065442118752955], ('3', '21'):
[−55.35950791884553, −56.294182190641429, −55.82684504474348], ('8', '7'):
[−58.171730502492018, −56.279187820566463, −57.225459161529244], ('15', '13'):
[−58.966269899599325, −57.94659373287913, −58.456431816239231], ('18', '8'):
[−48.112918785645675, −47.083772570878097, −47.598345678261886], ('18', '19'):
[−55.609213503122611, −54.109479912772464, −54.859346707947537]}

Table 9 lists the Kalman Filtered Test 19 Output Edges (Connections) to be inserted into force directed graph theory inputs.

TABLE 9

Edges = [['1', '20'], ['1', '13'], ['1', '10'], ['1', '7'], ['2', '13'], ['2', '19'], ['2', '8'], ['2', '18'], ['3', '20'], ['3', '18'], ['3', '6'], ['3', '5'], ['3', '8'], ['4', '12'], ['4', '21'], ['4', '18'], ['4', '17'], ['5', '15'], ['5', '3'], ['5', '21'], ['5', '18'], ['5', '8'], ['6', '10'], ['6', '3'], ['6', '20'], ['6', '14'], ['6', '15'], ['7', '14'], ['7', '10'], ['7', '20'], ['7', '1'], ['7', '3'], ['8', '18'], ['8', '20'], ['8', '19'], ['8', '11'], ['8', '13'], ['9', '14'], ['9', '10'], ['9', '22'], ['9', '6'], ['10', '20'], ['10', '6'], ['10', '9'], ['10', '18'], ['10', '7'], ['11', '18'], ['11', '12'], ['11', '8'], ['11', '19'], ['11', '20'], ['12', '4'], ['12', '15'], ['12', '11'], ['12', '21'], ['12', '18'], ['13', '2'], ['13', '1'], ['13', '8'], ['13', '20'], ['13', '19'], ['14', '22'], ['14', '9'], ['14', '7'], ['14', '6'], ['15', '18'], ['15', '21'], ['15', '12'], ['15', '5'], ['15', '20'], ['17', '21'], ['17', '4'], ['17', '15'], ['17', '12'], ['18', '8'], ['18', '15'], ['18', '11'], ['18', '3'], ['18', '12'], ['19', '8'], ['19', '2'], ['19', '11'], ['19', '13'], ['19', '15'], ['20', '8'], ['20', '3'], ['20', '10'], ['20', '1'], ['20', '6'], ['21', '4'], ['21', '15'], ['21', '12'], ['21', '5'], ['22', '14'], ['22', '9']]

Figure 8:
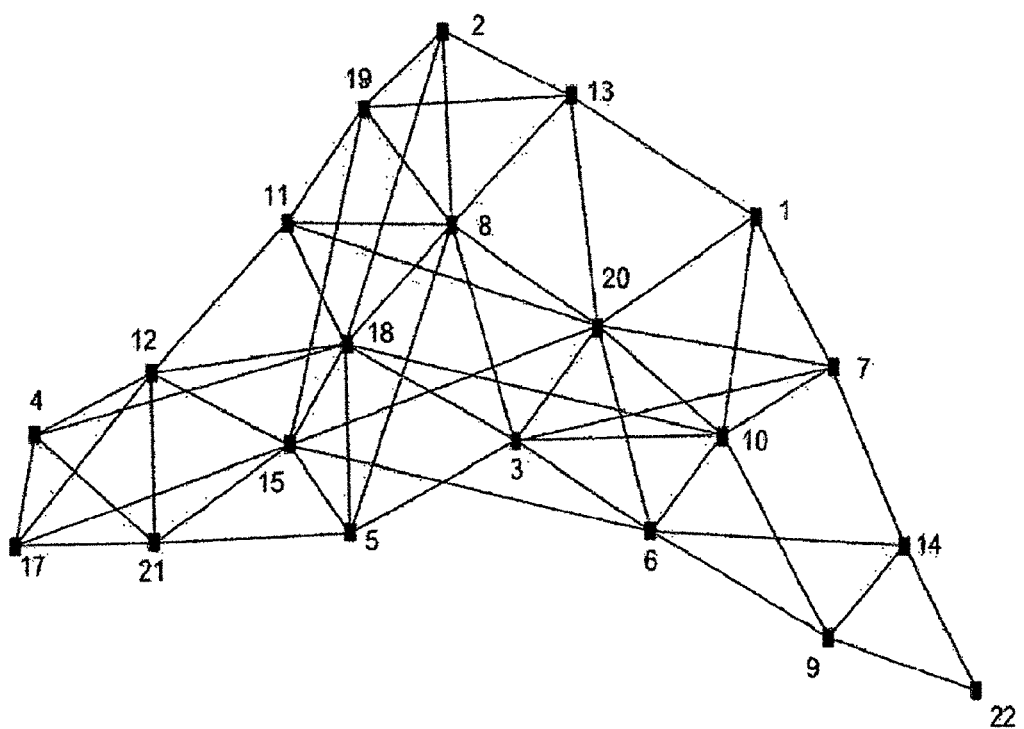
FIG. 8 illustrates an exemplary diagram for Kalman Filtered Force Directed Graph Drawing Using Force Directed Graph Drawing Library D3.js in Test 19.

FIG. 8 illustrates an exemplary diagram for Kalman Filtered Force Directed Graph Drawing Using Force Directed Graph Drawing Library D3.js in Test 19.

Table 10 lists the Kalman Filtered (X,Y) coordinate for Test 19.

TABLE 10

Kalman_Filtered_Coordinates =
[["1",458.5329141222706,94.14750059478128],["2",211.94776585069076, −63.35473535607196],["3",270.24444573641847,283.6874768374006],["4", −109.13671005209524,277.46045059780266],["5",138.33486094002419,359.4507208269634], ["6",377.3524201988945,358.95324721755572],["7",520.2057063582507,221.879107553335],["8", 219.59528966608423,102.64145373542816],["9",517.2887496584899,447.984784192003445], [10,431.30043654985474,277.7150634858197],["11",91.8583783012601,100.67873710172903], ["12",−15.534089758761343,226.06116151204526],["13",313.83175453940163, −6.821709906686433],["14",574.9981303642516,370.5214743367375],["15",90.7264058940126, 286.625914321973],["17", −124.26363823739828,371.3823588497608],["18",135.46691247472558,201.94905796310925], ["19",150.20499834986774,4.210532575829226],["20",335.87694004917006,187.2467469529189], ["21", −13.737499217366466,368.22634891341596],["22",633.9718126571761,492.7709502855854]]

Figure 9:
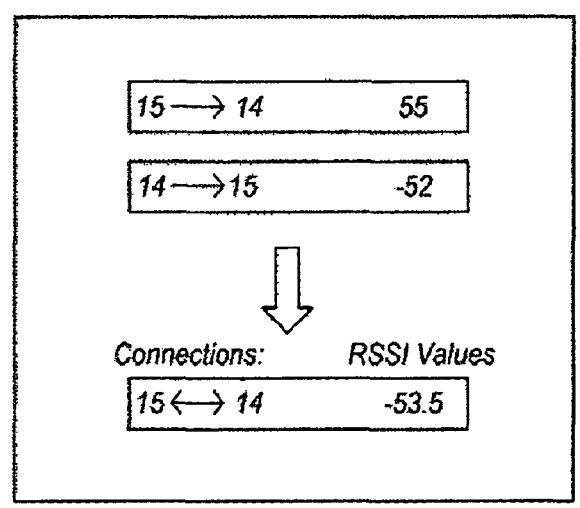
FIG. 9 illustrates an exemplary diagram for determining phone to phone connection strength with max filter in Test 19 according to an embodiment.

FIG. 9 illustrates an exemplary diagram for determining phone to phone connection strength with max filter in Test 19 according to an embodiment. It is noted that the maxes of the phone to phone connection strength is average.

Table 11 lists max values (One Direction, Other Direction, Average of Both Directions) for Test 19.

TABLE 11

Max_values = {('1', '20'): [−44, −44, −44.0], ('15', '14'): [−55, −52, −53.5], ('3', '15'): [−49, −50, −49.5], ('22', '6'): [−53, −52, −52.5], ('13', '21'): [−58, −58, −58.0], ('18', '22'): [−55, −55, −55.0], ('22', '21'): [−57, −56, −56.5], ('11', '10'): [−56, −57, −56.5], ('4', '5'): [−52, −53, −52.5], ('11', '9'): [−58, −59, −58.5], ('7', '1'): [−48, −49, −48.5], ('21', '17'): [−48, −48, −48.0], ('10', '19'): [−54, −53, −53.5], ('6', '15'): [−49, −50, −49.5], ('6', '5'): [−50, −50, −50.0], ('20', '13'): [−49, −47, −47.5], ('14', '18'): [−52, −54, −53.0], ('1', '14'): [−51, −52, −51.5], ('22', '19'): [−58, −58, −58.0], ('2', '1'): [−52, −52, −52.0], ('19', '15'): [−48, −48, −48.0], ('9', '22'): [−47, −48, −47.5], ('14', '2'): [−55, −55, −55.0], ('4', '1'): [−56, −56, −56.0], ('5', '14'): [−57, −56, −56.5], ('21', '19'): [−57, −56, −56.5], ('7', '5'): [−57, −59, −58.0], ('2', '3'): [−52, −52, −52.0], ('20', '18'): [−46, −50, −48.0], ('3', '8'): [−47, −47, −47.0], ('17', '10'): [−58, −58, −58.0], ('22', '12'): [−60, −57, −58.5], ('10', '21'): [−54, −54, −54.0], ('7', '4'): [−59, −59, −59.0], ('17', '20'): [−54, −55, −54.5], ('14', '20'): [−48, −47, −47.5], ('3', '7'): [−53, −53, −53.0], ('6', '1'): [−50, −50, −50.0], ('2', '15'): [−52, −54, −53.0], ('7', '17'): [−64, −62, −63.0], ('9', '7'): [−50, −49, −49.5], ('2', '5'): [−58, −59, −58.5], ('4', '10'): [−55, −56, −55.5], ('8', '17'): [−55, −53, −54.0], ('22', '8'): [−52, −53, −52.5], ('1', '18'): [−50, −50, −50.0], ('3', '22'): [−54, −55, −54.5], ('21', '4'): [−43, −43, −43.0], ('2', '7'): [−55, −54, −54.5], ('8', '4'): [−56, −55, −55.5], ('3', '4'): [−54, −52, −53.0], ('10', '8'): [−50, −50, −50.0], ('6', '18'): [−52, −52, −52.0], ('21', '5'): [−48, −48, −48.0], ('1', '22'): [−51, −52, −51.5], ('21', '15'): [−42, −44, −43.0], ('3', '13'): [−50, −50, −50.0], ('2', '9'): [−58, −58, −58.0], ('1', '11'): [−50, −50, −50.0], ('17', '6'): [−59, −58, −58.5], ('13', '9'): [−54, −56, −55.0], ('11', '12'): [−43, −42, −42.5], ('6', '21'): [−51, −52, −51.5], ('13', '18'): [−50, −50, −50.0], ('17', '5'): [−53, −54, −53.5], ('13', '8'): [−45, −44, −44.5], ('4', '9'): [−59, −61, −60.0], ('19', '8'): [−47, −43, −45.0], ('11', '5'): [−59, −52, −51.0], ('19', '19'): [−61, −61, −61.0], ('12', '18'): [−46, −48, −47.0], ('14', '12'): [−59, −56, −57.5], ('20', '22'): [−52, −54, −53.0], ('21', '1'): [−55, −55, −55.0], ('13', '6'): [−49, −50, −49.5], ('13', '11'): [−48, −49, −48.5], ('19', '17'): [−59, −59, −59.0], ('2', '10'): [−55, −53, −54.0], ('4', '6'): [−54, −56, −55.0], ('4', '17'): [−46, −46, −46.0], ('8', '12'): [−48, −48, −48.0], ('6', '2'): [−58, −58, −58.0], ('22', '10'): [−47, −50, −48.5], ('19', '5'): [−51, −50, −50.5], ('22', '7'): [−53, −52, −52.5], ('2', '17'): [−62, −61, −61.5], ('7', '15'): [−57, −58, −57.5], ('9', '18'):

TABLE 11-continued

[−55, −56, −55.5], ('8', '15'): [−48, −50, −49.0], ('9', '1'): [−51, −50, −50.5], ('14', '19'): [−55, −58, −56.5], ('3', '18'): [−44, −46, −45.0], ('11', '20'): [−47, −46, −46.5], ('18', '2'): [−50, −50, −50.0], ('4', '2'): [−54, −57, −55.5], ('13', '1'): [−46, −45, −45.5], ('10', '9'): [−45, −47, −46.0], ('13', '22'): [−56, −57, −56.5], ('3', '20'): [−43, −43, −43.0], ('22', '4'): [−61, −60, −60.5], ('11', '2'): [−51, −50, −50.5], ('4', '19'): [−53, −53, −53.0], ('21', '8'): [−53, −52, −52.5], ('15', '10'): [−50, −50, −50.0], ('3', '11'): [−54, −52, 53.0], ('12', '13'): [−58, −56, −57.0], ('8', '2'): [−49, −47, −48.0], ('3', '9'): [−54, −53, −53.5], ('6', '7'): [−55, −54, −54.5], ('21', '9'): [−59, −57, −58.0], ('11', '14'): [−53, −53, −53.0], ('18', '11'): [−44, −44, −44.0], ('6', '11'): [−55, −54, −54.5], ('7', '19'): [−55, −57, −56.0], ('17', '3'): [−55, −56, −56.0], ('19', '2'): [−44, −43, −43.5], ('17', '13'): [−59, −61, −60.0], ('14', '10'): [−48, −46, −47.0], ('12', '21'): [−47, −47, −47.0], ('3', '6'): [−47, −46, −46.5], ('7', '21'): [−55, −54, −54.5], ('10', '3'): [−49, −49, −49.0], ('2', '12'): [−52, −53, −52.5], ('3', '5'): [−48, −48, −48.0], ('7', '12'): [−56, −56, −56.0], ('5', '10'): [−50, −50, −50.0], ('9', '15'): [−57, −57, −57.0], ('4', '15'): [−47, −48, −47.5], ('17', '14'): [−61, −62, −61.5], ('10', '1'): [−46, −48, −47.0], ('11', '8'): [−46, −46, −46.0], ('21', '2'): [−57, −56, −56.5], ('20', '4'): [−57, −55, −56.0], ('15', '5'): [−45, −44, −44.5], ('11', '22'): [−55, −56, −55.5], ('20', '9'): [−52, −52, −52.0], ('21', '20'): [−52, −51, −51.5], ('19', '13'): [−49, −48, −48.5], ('6', '14'): [−51, −50, −50.5], ('14', '3'): [−52, −52, −52.0], ('14', '8'): [−56, −56, −56.0], ('15', '12'): [−43, −42, −42.5], ('1', '5'): [−55, −56, −55.5], ('20', '10'): [−43, −42, −42.5], ('11', '7'): [−57, −56, −56.5], ('17', '18'): [−54, −55, −54.5], ('1', '15'): [−54, −55, −54.5], ('13', '14'): [−52, −52, −52.0], ('21', '14'): [−59, −59, −59.0], ('10', '13'): [−50, −50, −50.0], ('19', '12'): [−52, −53, −52.5], ('20', '2'): [−47, −46, −46.5], ('9', '6'): [−51, −52, −51.5], ('21', '18'): [−52, −54, −53.0], ('20', '15'): [−48, −49, −48.5], ('20', '19'): [−51, −54, −52.5], ('17', '11'): [−54, −55, −54.5], ('17', '9'): [−58, −62, −60.0], ('22', '5'): [−58, −58, −58.0], ('7', '10'): [−47, −48, −47.5], ('5', '12'): [−53, −53, −53.0], ('4', '13'): [−57, −57, −57.0], ('22', '14'): [−43, −42, −42.5], ('1', '19'): [−52, −53, −52.5], ('20', '8'): [−43, −42, −42.5], ('11', '4'): [−50, −50, −50.0], ('15', '17'): [−51, −50, −50.5], ('3', '1'): [−54, −53, −53.5], ('12', '10'): [−55, −54, −54.5], ('12', '1'): [−56, −57, −56.5], ('18', '7'): [−53, −51, −52.0], ('8', '6'): [−50, −50, −50.0], ('5', '9'): [−55, −55, −55.0], ('12', '17'): [−50, −49, −49.5], ('17', '1'): [−61, −62, −61.5], ('18', '5'): [−50, −48, −49.0], ('12', '4'): [−43, −42, −42.5], ('18', '15'): [−42, −42, −42.0], ('9', '8'): [−53, −54, −53.5], ('12', '6'): [−53, −55, −54.0], ('1', '8'): [−49, −50, −49.5], ('10', '18'): [−48, −48, −48.0], ('13', '7'): [−52, −52, −52.0], ('3', '19'): [−50, −51, −50.5], ('12', '9'): [−57, −55, −56.0], ('20', '12'): [−48, −48, −48.0], ('2', '22'): [−58, −59, −58.5], ('6', '19'): [−57, −57, −57.0], ('13', '5'): [−56, −56, −56.0], ('4', '18'): [−48, −50, −49.0], ('15', '11'): [−49, −48, −48.5], ('20', '7'): [−49, −48, −48.5], ('6', '20'): [−46, −45, −45.5], ('5', '8'): [−51, −51, −51.0], ('19', '11'): [−45, −44, −44.5], ('6', '10'): [−45, −43, −44.0], ('20', '5'): [−51, −53, −52.0], ('13', '2'): [−43, −43, −43.0], ('21', '11'): [−49, −50, −49.5], ('14', '4'): [−58, −56, −57.0], ('22', '17'): [−65, −63, −64.0], ('7', '14'): [−44, −44, −44.0], ('14', '9'): [−43, −44, −43.5], ('15', '22'): [−57, −57, −57.0], ('3', '21'): [−52, −51, −51.5], ('8', '7'): [−52, −50, −51.0], ('15', '13'): [−52, −52, −52.0], ('18', '8'): [−43, −43, −43.0], ('18', '19'): [−49, −47, −48.0]}

Table 12 lists max filtered Output Edges (Connections) to be inserted into D3.js code for Test 19.

TABLE 12

Max_edges = [['1', '20'], ['1', '13'], ['1', '10'], ['1', '7'], ['2', '13'], ['2', '19'], ['2', '20'], ['2', '8'], ['3', '20'], ['3', '18'], ['3', '6'], ['3', '8'], ['3', '5'], ['4', '12'], ['4', '21'], ['4', '17'], ['4', '15'], ['5', '15'], ['5', '21'], ['5', '3'], ['5', '18'], ['5', '6'], ['6', '10'], ['6', '20'], ['6', '3'], ['6', '15'], ['7', '14'], ['7', '10'], ['7', '1'], ['7', '20'], ['8', '20'], ['8', '18'], ['8', '13'], ['8', '19'], ['8', '11'], ['9', '14'], ['9', '10'], ['9', '22'], ['9', '7'], ['10', '20'], ['10', '6'], ['10', '9'], ['10', '14'], ['10', '1'], ['11', '12'], ['11', '18'], ['11', '19'], ['11', '8'], ['11', '20'], ['12', '11'], ['12', '15'], ['12', '4'], ['12', '18'], ['13', '2'], ['13', '8'], ['13', '1'], ['13', '20'], ['14', '22'], ['14', '9'], ['14', '7'], ['14', '10'], ['15', '18'], ['15', '12'], ['15', '21'], ['15', '5'], ['17', '4'], ['17', '21'], ['17', '12'], ['17', '15'], ['18', '15'], ['18', '8'], ['18', '11'], ['18', '3'], ['19', '2'], ['19', '11'], ['19', '8'], ['19', '15'], ['19', '18'], ['20', '10'], ['20', '8'], ['20', '3'], ['20', '1'], ['20', '6'], ['21', '4'], ['21', '15'], ['21', '12'], ['21', '17'], ['22', '14'], ['22', '9']]

Figure 10:
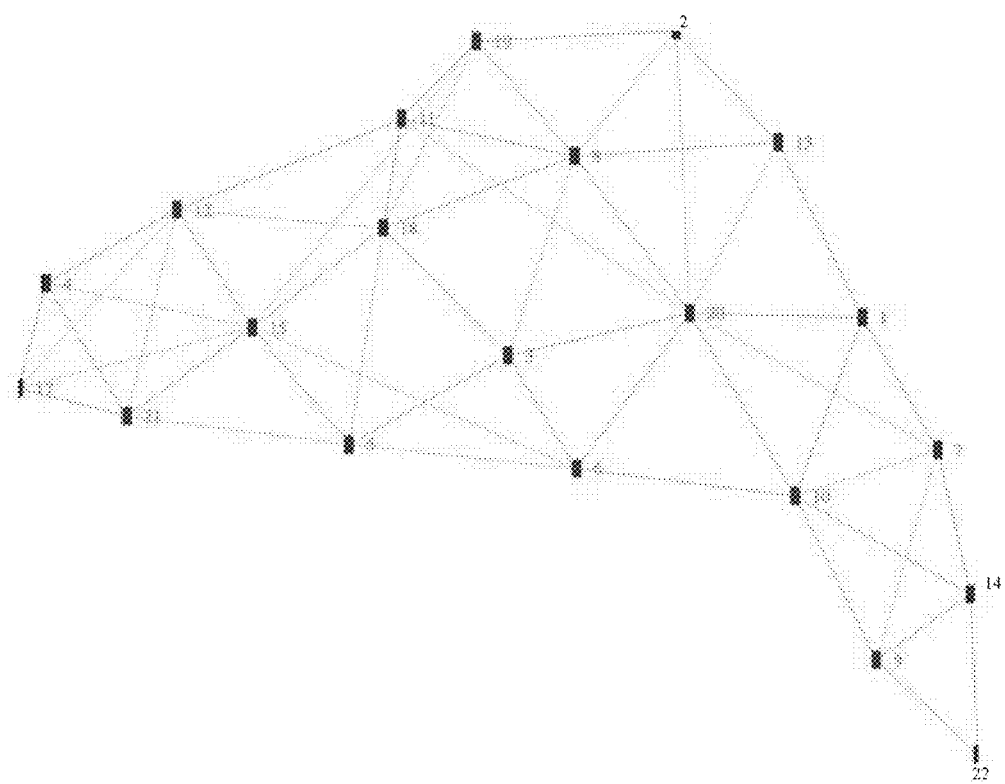
FIG. 10 illustrates an exemplary diagram of max filtered force directed graph drawing using force directed graph drawing library D3.js for Test 19 according to an embodiment.

FIG. 10 illustrates an exemplary diagram of max filtered force directed graph drawing using force directed graph drawing library D3.js for Test 19 according to an embodiment.

Table 13 lists max filtered (X,Y) coordinate output .json for Test 19.

TABLE 13

Max_Filtered_(X,Y) = [["1",25.739692374583022,110.77196657339223],["2", −5.824509706020064,400.86094598273485],["3",265.1754575498918,275.82090118723323],["4", 595.170585626277,494.300954276040951,["5",420.0596610608523,292.61772700908426],["6", 281.59031157551925,167.8606143136469],["7",68.03445255331252, −14.940592031033946],["8",124.66917364224715,374.90129830363986],["9",125.27074244409266, −136.20940086470318],["10",163.6924430565924,38.51434126129914],["11",222.54248350641112, 484.0493657980021],["12",424.14622785293017,528.778755036346457],["13", −17.51685619298813,273.82446335667703],["14",200.94074553375646, −97.3809900350623],["15",428.09897088569573,418.9177835977496],["17",558.0338430080125, 557.0531965629032],["18",289.0916898014363,418.1648199359243],["19",132.9657836857719, 498.1903546238373],["20",127.98961295505055,210.77125056388633],["21",559.2264333937758, 416.67594296094421,["22",216.65673079234878,−220.9920115926178]]

Table 14 lists max filtered RSSI (X,Y) scaled values for Test 19.

TABLE 14

| Node | X | Y |
|---|---|---|
| 1 | 0.485199837 | 3.148275572 |
| 2 | 1 | 1 |
| 3 | 2.612831137 | 2.58240768 |
| 4 | 5.522238973 | 1.866624961 |
| 5 | 3.759695045 | 2.857668212 |
| 6 | 2.454514487 | 3.393819676 |
| 7 | 0.466085118 | 4.152226939 |
| 8 | 1.863967452 | 1.517831081 |
| 9 | 0.564807502 | 5.16260715 |
| 10 | 1.284265853 | 4.015145012 |
| 11 | 2.839969278 | 0.98941317 |
| 12 | 4.391088534 | 1.184713343 |
| 13 | 0.592684139 | 1.87570907 |
| 14 | 1.203211165 | 5.078810467 |
| 15 | 4.139093686 | 1.977892381 |
| 17 | 5.417557435 | 1.324614369 |
| 18 | 3.146317356 | 1.628759538 |
| 19 | 2.23752142 | 0.660174098 |
| 20 | 1.469067059 | 2.696232341 |
| 21 | 5.068064549 | 2.328277131 |
| 22 | 1 | 6 |

Table 15 lists test layout actual location scaled for Test 19.

TABLE 15

| Node | X | Y |
|---|---|---|
| 1 | 1 | 3 |
| 2 | 1 | 1 |
| 3 | 3 | 3 |
| 4 | 5 | 1 |
| 5 | 4 | 3 |
| 6 | 3 | 4 |
| 7 | 1 | 4 |
| 8 | 2 | 2 |
| 9 | 2 | 5 |
| 10 | 2 | 4 |
| 11 | 3 | 1 |
| 12 | 4 | 1 |
| 13 | 1 | 2 |
| 14 | 1 | 5 |
| 15 | 4 | 2 |
| 17 | 6 | 1 |
| 18 | 3 | 2 |
| 19 | 2 | 1 |
| 20 | 2 | 3 |
| 21 | 5 | 2 |
| 22 | 1 | 6 |

Table 16 lists delta between RSSI D3.js output and test layout location (scaled and actual) for Test 19.

TABLE 16

| Node | Scaled Distance (1 Unit = .5 Meters) | Actual Distance (Meters) |
|---|---|---|
| 1 | 0.535728339 | 0.267864169 |
| 2 | 0 | 0 |
| 3 | 0.56945858 | 0.28472929 |
| 4 | 1.011816371 | 0.505908185 |
| 5 | 0.279293411 | 0.139646705 |
| 6 | 0.815480858 | 0.407740429 |
| 7 | 0.555191987 | 0.277595993 |
| 8 | 0.500990739 | 0.25049537 |
| 9 | 1.444374809 | 0.722187405 |
| 10 | 0.715894364 | 0.357947182 |
| 11 | 0.160380526 | 0.080190263 |
| 12 | 0.432515041 | 0.21625752 |
| 13 | 0.425857307 | 0.212928653 |
| 14 | 0.217958407 | 0.108979203 |
| 15 | 0.140839627 | 0.070419813 |
| 17 | 0.666793694 | 0.333396847 |
| 18 | 0.399034146 | 0.199517073 |
| 19 | 0.41460592 | 0.20730296 |
| 20 | 0.611689937 | 0.305844968 |
| 21 | 0.33525909 | 0.167629545 |
| 22 | 0 | 0 |

Figure 11:
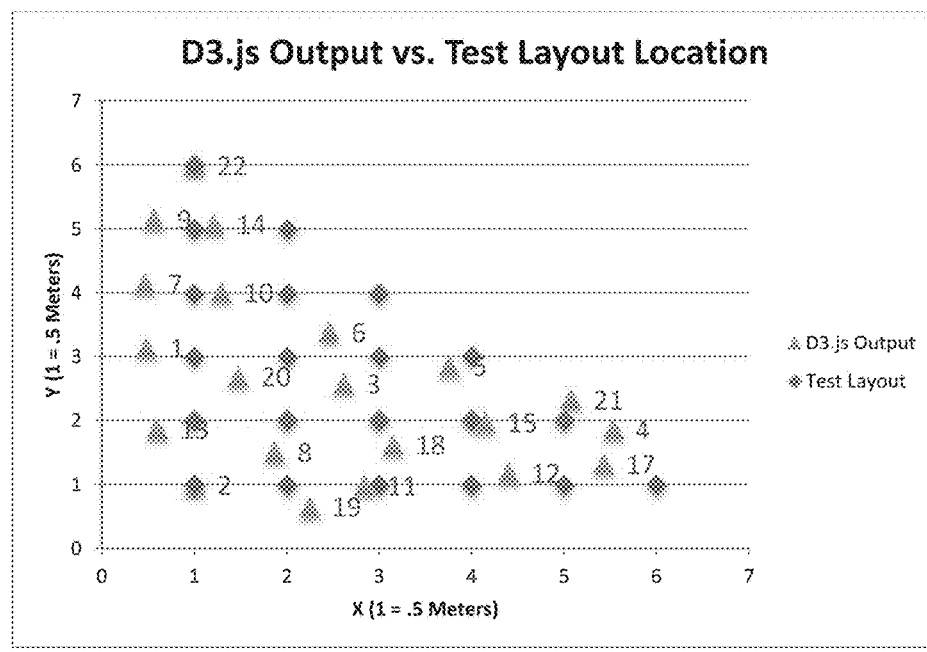
FIG. 11 illustrates a graph of max filtered RSSI scaled value accuracy for Test 19.

FIG. 11 illustrates a graph of max filtered RSSI scaled value accuracy for Test 19. FIG. 6 is referenced for test layout nodes.

EXAMPLE 20

TEST 20: Hanging Outside with Beacon in NE Corner

Overview:

Test 11 except measuring initial GPS, average GPS and test completed outside with WI-FI and BLUETOOTH devices running at large distance from test (20 yards).

Figure 12:
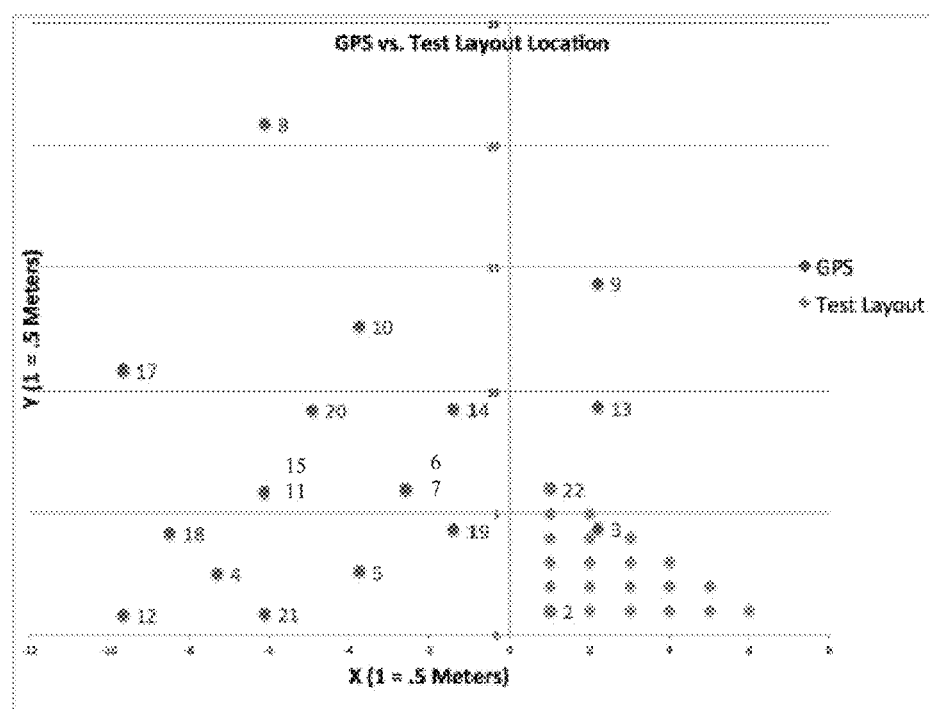
FIG. 12 illustrates a graph for comparison with GPS accuracy for Test 20.

Procedure:

1: Elevate phones 5.5 feet off the ground using the hanging structure described in Precursor to Experiment Procedure step 2 in the pattern demonstrated in FIG. 6. Place the hanging apparatus outside. Additionally, note that in FIG. 6, the lighter grid lines indicate 0.25 meter intervals while the thicker grid lines are 0.5 meters. Orient the grid so the beacon is in the North-East most corner of it.
2: Turn the phones and wait until phone pickup signal.
3: Measure average GPS over 5 minutes with GPS tracking android app with no devices or people within 20 yards of the beacons and receivers.
4: Log Data as shown in FIG. 12.
5: Convert GPS Angular decimal form data into an (x,y) scatter plot using an equirectangular projection as shown below:
$x = r\lambda \cos(\varphi_0)$
$y = r\varphi$
$\varphi_0$ denotes a latitude close to the center of your map
r is the radius of the earth
$\lambda$ is decimal form latitude
$\varphi$ is decimal form longitude
6: Scale the GPS (X,Y) scatterplot as shown in max filtered pseudocode part IV to create a comparative location graph as shown in Table 18 and FIG. 12.

Conclusion:

Based upon the way we completed our testing, GPS has a 15% sub-meter accuracy compared to our method of location and no sequencing accuracy. Also nodes 15 and 11 as well as nodes 6 and 7 had identical locations, which is incorrect. Finally phones 1 and 16 in the test were unable to receive GPS signal in our location.

Table 17 lists the GPS 5 minute average predicted location for Test 20.

TABLE 17

| Node | X | Y |
|---|---|---|
| 11 | 43.18116 | −111.02999 |
| 10 | 43.18118 | −111.02997 |
| 13 | 43.18115 | −111.02996 |
| 12 | 43.18115 | −111.03001 |
| 15 | 43.18116 | −111.02999 |
| 21 | 43.18114 | −111.03 |

TABLE 17-continued

| Node | X | Y |
|---|---|---|
| 17 | 43.18119 | -111.02999 |
| 19 | 43.18114 | -111.02998 |
| 18 | 43.18116 | -111.03 |
| 22 | 43.18114 | -111.02997 |
| 20 | 43.18117 | -111.02998 |
| 3 | 43.18113 | -111.02997 |
| 2 | 43.18112 | -111.02998 |
| 5 | 43.18114 | -111.02999 |
| 4 | 43.18115 | -111.03 |
| 7 | 43.18115 | -111.02998 |
| 6 | 43.18115 | -111.02998 |
| 9 | 43.18117 | -111.02995 |
| 8 | 43.18122 | -111.02996 |
| 14 | 43.18116 | -111.02997 |

Table 18 lists the GPS (X,Y) scaled predicted location values for Test 20.

TABLE 18

| Node | X | Y |
|---|---|---|
| 11 | 43.18116 | -111.02999 |
| 10 | 43.18118 | -111.02997 |
| 13 | 43.18115 | -111.02996 |
| 12 | 43.18115 | -111.03001 |
| 15 | 43.18116 | -111.02999 |
| 21 | 43.18114 | -111.03 |
| 17 | 43.18119 | -111.02999 |
| 19 | 43.18114 | -111.02998 |
| 18 | 43.18116 | -111.03 |
| 22 | 43.18114 | -111.02997 |
| 20 | 43.18117 | -111.02998 |
| 3 | 43.18113 | -111.02997 |
| 2 | 43.18112 | -111.02998 |
| 5 | 43.18114 | -111.02999 |
| 4 | 43.18115 | -111.03 |
| 7 | 43.18115 | -111.02998 |
| 6 | 43.18115 | -111.02998 |
| 9 | 43.18117 | -111.02995 |
| 8 | 43.18122 | -111.02996 |
| 14 | 43.18116 | -111.02997 |

Table 19 lists the GPS node test layout actual location for Test 20.

TABLE 19

| Node | X | Y |
|---|---|---|
| 1 | 1 | 3 |
| 2 | 1 | 1 |
| 3 | 3 | 3 |
| 4 | 5 | 1 |
| 5 | 4 | 3 |
| 6 | 3 | 4 |
| 7 | 1 | 4 |
| 8 | 2 | 2 |
| 9 | 2 | 5 |
| 10 | 2 | 4 |
| 11 | 3 | 1 |
| 12 | 4 | 1 |
| 13 | 1 | 2 |
| 14 | 1 | 5 |
| 15 | 4 | 2 |
| 17 | 6 | 1 |
| 18 | 3 | 2 |
| 19 | 2 | 1 |
| 20 | 2 | 3 |
| 21 | 5 | 2 |
| 22 | 1 | 6 |

Table 20 lists the GPS delta between recorded and actual location (scaled and actual) for Test 20.

TABLE 20

| Node | Scaled Distance (1 Unit = .5 Meters) | Actual Distance (Meters) |
|---|---|---|
| 2 | 0 | 0 |
| 3 | 1.578117079 | 0.789058539 |
| 4 | 12.38899562 | 6.194497808 |
| 5 | 7.749257355 | 3.874628678 |
| 6 | 5.885212601 | 2.9426063 |
| 7 | 4.052120934 | 2.026060467 |
| 8 | 20.55923491 | 10.27961746 |
| 9 | 9.35300469 | 4.676502345 |
| 10 | 10.33495082 | 5.167475409 |
| 11 | 10.33908354 | 5.169541768 |
| 12 | 13.66297699 | 6.831488495 |
| 13 | 7.446026537 | 3.723013268 |
| 14 | 4.907490352 | 2.453745176 |
| 15 | 10.83175276 | 5.415876381 |
| 17 | 18.49628141 | 9.248140705 |
| 18 | 11.68453479 | 5.842267397 |
| 19 | 4.714537933 | 2.357268966 |
| 20 | 9.323169888 | 4.661584944 |
| 21 | 11.16305481 | 5.581527405 |
| 22 | 0 | 0 |

FIG. 12 illustrates a graph for comparison with GPS accuracy for Test 20.

Based on Examples 1-20, it was found that utilizing the system described herein increased in accuracy, and consistency, as the actual distance between devices decreased. Therefore, given the crowd-like plurality of devices in most desirable applications of localization, including festivals, households, malls, offices, etc, we can organize the devices according to the strongest RSSI connections, or the devices that are most likely to be adjacent to each other. If a data set of mobile devices with their strongest RSSI connections are used forces can be attached to those connections, limit the number we employ, and render a grid using graph theory. This allows us to take the knowledge of which devices are nearest to each other and stitch the order of the devices together in a cohesive grid. Using this method, described at a high level here and in greater detail later, we were able to achieve the creation of a grid comprising of relative device-to-device position to within sub-meter accuracy.

In one embodiment, the system is configured to localize each node of a system relative to every other node in the system. A node may include a mobile device with sensor, e.g., BLUETOOTH Low Energy (BLE) sensor. The sensor can act both as BLE beacon and receiver as shown FIG. 1. BLE RSSI values between nodes are used to find proximities between nodes. Proximities between nodes data is run through a Force Directed Graph Drawing algorithm. In one embodiment, the system uses mobile stations, e.g., Android moto E 2nd gen, as BLE capable nodes. One or more of these devices were used as nodes, in a preferred embodiment, 10 or more mobile devices are used as nodes, in a more preferred embodiment, twenty or more these mobile stations can be used, with BLE capabilities to record BLE RSSI data in a half meter grid (a right triangle with two equal sides of 6 mobile devices).

In one embodiment, raw BLUETOOTH low energy Received Signal Strength Indication data from phones was measured and/or recorded. A hash table that accumulates and records the connection, direction and RSSI value of each beacon phone to receiver phone connection, is shown in Table 7. Every connection has multiple RSSI vales; therefore, we filter all RSSI values through Kalman filter and take the average of those filtered values in both directions to determine a RSSI value that will be used in our system as shown in FIG. 7 and Table 8.

We then sort the RSSI value of each phone's connection from greatest to least. We then iterate over every phone (for example: Phone 1) and chooses the highest 6 connections where that phone was a receiver beacon (for example: [Phone 20, Phone 13, Phone 10, Phone 7, Phone 14, Phone 11]→Phone 1).

We then find the standard deviation of those 6 connections' values. If standard deviation value is higher than 3, we pass the two highest values to the next phase of the system; if standard deviation value is higher than 2 but less than or equal to 3, we pass the three highest values to the next phase of the system; if standard deviation value is lower than or equal to 2, we pass the four highest values to the next phase of the system.

We then collect all the values (highest connections) passed by the previous stage of the program. This collected data (Table 9) is connecting/edges data that will be passed into part III of the psuedocode included below. Extract points/nodes data that will be passed into part III by getting all the unique points of the connection/edge data.

Pass data from part II into Force Directed Graph Layout in part III.

Create a two dimensional coordinate plane where our graph will be simulated.

A simulation runs in 2D plane and reaches equilibrium, a state where nodes stop moving.

Record (X,Y) data of every point on the 2D plane.

Scale the 2D Plane based upon 2 known mobile station locations.

In one embodiment, raw BLUETOOTH low energy Received Signal Strength Indication data from phones was measured and/or recorded. A python creates a hash table that accumulates and records the connection, direction and RSSI of each beacon phone to receiver phone connection as shown in Table 7. Every connection has multiple RSSI values; therefore, we filter all RSSI values to find the maximum RSSI value and take average of those max values to determine a RSSI value that will be used in our system as shown in FIG. 9 and Table 11.

Sort the RSSI value of each beacon phone connections from greatest to least, iterate over every phone (for example: Phone 1) and choose the highest 6 connections where that phone was a receiver beacon (for example: [Phone 20, Phone 13, Phone 10, Phone 7, Phone 8, Phone 6]→Phone 1).

Find standard deviation of those 6 connections' values. If standard deviation value is higher than 3, we pass the two highest values to the next phase of the system; if standard deviation value is higher than 2 but less than or equal to 3, we pass the three highest values to the next phase of the system; it standard deviation value is lower than or equal to 2, we pass the four highest values to the next phase of the system.

Collect all the values (highest connections) passed by the previous stage of the program. The collected data is connections/edges data (FIG. 21) that will be passed into part III. Extract points/nodes data that will be passed into part III by getting all the unique points of the connection/edge data.

Pass data from part II into D3.js Force Directed Graph Layout (http://d3js.org/) in part III.

```
Averaged Kalman Filter Pseudocode:
//Part II pseudocode
A = createTable( )
for every phone in phones:
   B = createTable( )
   for every connection in phone:
      if connection does not exists:
         create a new key and add RSSI value as the next element of key
      else:
         add RSSI value to previous created key
   for every b in B:
      kalmanFilter(b)
      average(b)
   A.add(B)
C = getUniqueReceivers(A)
D = createTable( )
E = createTable( )
for every c in C:
   D.add(c)
   D.sort( )
   D = D[0:6]
   sd = standardDeviation(D)
   if sd > 3:
      D = D[0:2]
   else if sd > 2:
      D = D]0:4]
   else if sd <= 2:
      D = D[0:5]
   E.add(D)
   D.makeEmpty( )
// E is connections/edges data
F = uniquePoints(E)
// F is points/nodes data
//Part III pseudocode
G = created2DPlane( )
G.simulateForceDirected(nodes = F, edges = E)
   .linkDistance(30)
   .charge(−10000)
   .gravity(0.45)
if G.simulationEnded:
   for f in F:
      f.log(x,y)
```

Create a two dimensional coordinate plane where our graph will be simulated.

A simulation runs in 2D plane and reaches equilibrium, a state where nodes stop moving.

Record (X,Y) data of every point on the 2D plane.

Scale the 2D Plane based upon 2 known mobile station locations.

stations to scale the force directed drawing mesh which allows for submeter phone location accuracy. We are not required to survey areas to learn their RFID characteristics (as opposed to the methods (e.g., trilateration and other methods) in the related art).

Unlike other techniques that usually use trilateration and/or triangulation in the related art, embodiments of the

```
Max Filtered Pseudocode:
//Part II pseudocode
A = createTable( )
for every phone in phones:
    B = createTable( )
    for every connection in phone:
        if connection does not exists:
            create a new key and add RSSI value as the next element of key
        else:
            add RSSI value to previous created key
    for every b in B:
        Max(b)
        average(b)
    A.add(B)
C = getUniqueReceivers(A)
D = createTable( )
E = createTable( )
for every c in C:
    D.add(c)
    D.sort( )
    D = D[0:6]
    sd = standardDeviation(D)
    if sd > 3:
        D = D[0:2]
    else if sd > 2:
        D = D[0:4]
    else if sd <= 2:
        D = D[0:5]
    E.add(D)
    D.makeEmpty( )
// E is connections/edges data
F = uniquePoints(E)
// F is points/nodes data
//Part III pseudocode (This is a preferred embodiment)(output shown Table 13)
G = created2DPlane( )
G.simulateForceDirected(nodes = F, edges = E)
    .linkDistance(30)
    .charge(-10000)
    .gravity(0.45)
if G.simulationEnded:
    for f in F:
        f.log(x,y)
//Part IV
f = D3.js (x,y) values
B = Subtract Node 2 X values from all other Nodes X values and subtract Node 2 Y value
from all other Nodes Y values. Set Node 2 equal to (0,0)
C = Graph B rotated so that Node 22 lies on Y axis and X value of Node 22 is equal to 0
D = C with graph translated so that Node 2 is positioned at (1,1)
E = D scaled so distance between Node 2 and Node 22 is equal to 5
```

Embodiments of the invention allow BLE capable nodes (mobile devices, beacons, etc) to know their relative position to other BLE capable nodes (mobile devices, beacons, etc). This relative positioning can be employed with other resources to achieve absolute position, which may comprise:
a. Access points where a BLE node is hardcoded with absolute locations;
b. GPS positioning to create an access point or awareness of surrounding environment;
c. Adaptive recognition of environments using an awareness of the change in relative positions, anomalies, and over-time logging of presumed constraints (walls, thresholds, tables, etc.); and/or
d. Relative position localization without use of any external hardware (beacons).

In an embodiment, we are employing APs, or access points in order to set a known distance between two mobile invention may use Force Directed Graph Drawing, which is generally used for visualization purposes.

Figure 13:
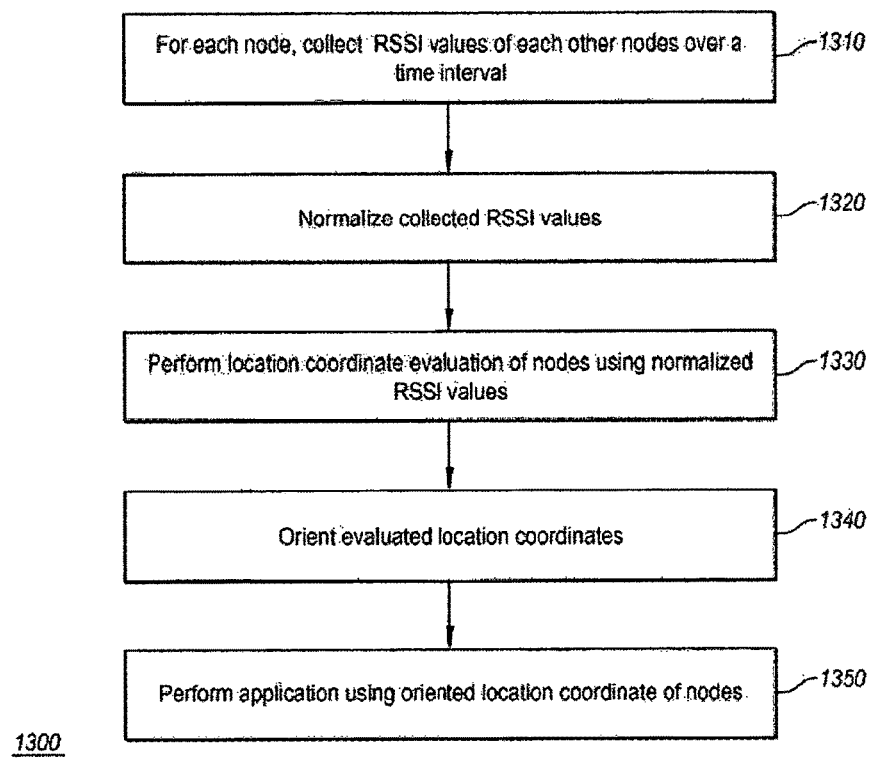
FIG. 13 illustrates an exemplary flow diagram of a wireless location method according to an embodiment.

FIG. 13 illustrates an exemplary flow diagram of a wireless location method according to an embodiment.

In an embodiment, wireless location method 1300 may be performed by a system of one or more nodes (e.g., mobile devices). The nodes of the system may be pre-arranged or ad-hoc (e.g., nodes may join or leave the system at times), and the processing of system may occur at the nodes or a server (centralized or distributed) or shared between some combinations of the nodes and server. In an embodiment, the nodes may be confined to a relatively small geographic location (e.g., a room where the nodes are generally sub-meters apart).

The wireless location method 1300 starts by collecting, for each node, a RSSI value (or a value indicative of signal strength) of each of the other nodes over a time interval 1310. In an embodiment, each node may be pre-configured receive wireless signals from other nodes (e.g., passively or actively receiving signal strengths of the other nodes in a wireless channel (e.g., WI-FI, BLUETOOTH, etc.)) or may be configured to receive such wireless signals. The RSSI values are collected over a time interval (e.g., 5 seconds, 30 seconds, 1 minutes, 2 minutes, etc.). In an embodiment, at least some of the nodes may be part of a mesh (e.g., a BLUETOOTH mesh or an ad-hoc WI-FI mesh) and the RSSI values may be collected from signals of other nodes of the mesh.

It is noted the node may receive one or more RSSI values at different times within the time interval (e.g., one of the other nodes may transmit a wireless signal to the receiving node at every second of a five second interval). In an embodiment, the RSSI values of wireless signals from a particular node may be aggregated to one RSSI value representative of the particular node over the time interval. For example, the maximum RSSI value from the particular node for the time interval may be used as the RSSI value for the particular node. In another example, the average or some weighted aggregation the of the one or more RSSI values may be used as the RSSI value for the particular node.

In an embodiment, all of collected RSSI values from each node to at least some of the other nodes may be entered as a matrix or some other data representation for processing at a server and/or one or more of the nodes.

In an embodiment, a node may only receive RSSI values from a subset of the nodes (e.g., when a node is not in wireless communication range of another node, e.g., when the room or geographic location may much larger in size than the wireless communication range).

The wireless location method 1300 processes a normalization of the collected RSSI value 1320.

For a mobile device, it is noted that the RSSI values may generally be measured as a power ratio (in decibels) of the measured power with reference to one milliwatt (dBm). Typical RSSI values for mobile devices depend on the wireless signal type, wireless conditions, and the power output of the mobile devices. For example, a typical signal for nearby devices may range >−40 dBm to −80 dBm, and relatively poor signals may be <−100 dBm to <−120 dBm.

It is noted, at least same or similar types of equipments (e.g., mobile device make and model, radio chipset, antenna, etc.), that the RSSI values received by a receiving node from a transmitting would be higher when the two nodes are closer to one another. However, when the equipments differ, the mixture of RSSI values may represent or hint at comparable physical distances. For example, a RSSI value for a wireless signal transmitted by a node of one type equipment may differ from a wireless signal transmitted by another node from a same physical distance (or even the same position) due to the different equipment (e.g., affecting the power level output of the wireless signal).

In an embodiment, goal of normalization is to normalize a correspondence of the received RSSI value to a physical distance (which can be relative distances among a number of nodes or the absolute physical distances between the nodes) between the receiving node and the transmitting node (e.g., removing or minimizing the equipment and/or other factors). In an embodiment, the range of RSSI values may be normalized to a standard relative range (e.g., relative distances or normalization values between zero and one).

In an embodiment, the normalization may set an upper bound and a lower bound for the RSSI values to be normalized to range between zero and one. In one example (which will be further discussed in the example below), upper bound may be set to an RSSI value of −40 dBm and a lower bound set to an RSSI value of −72 dBm. Therefore, RSSI values that are above −40 dBm may be normalized to 1, RSSI values that are below −72 dBm may be normalized to 0. In an embodiment, the upper bound and the lower bound may correspond to physical distance extremes between the receiving node and the transmitting node where it may be less likely that a change in the RSSI value represents a meaningful change in the physical distances. With the previous example, an RSSI value that is near −40 dBm may correspond to a high likelihood that the receiving node and the transmitting node are very close to one another, and an RSSI value that is below −72 dBm may correspond to a high likelihood that the receiving node and the transmitting node are already at a fringe distance of communication and/or detectability.

In an embodiment, the normalization may be performed according to a function, which may be linear, exponential, or other types functions. For example, normalization using a linear function may map the bounded domain of RSSI values to a range of between zero and one in a proportional relationship. In another example, normalization using an exponential function may map the RSSI values to between zero and one in a same direction but non-proportional relationship. In an embodiment, the normalization function may correspond to a fit (e.g., regression fit) of the RSSI values (e.g., a fit of a scatter plot of the RSSI values). The fit may be performed automatically, manually, or by a combination of automatic and manual fit.

In an embodiment, a group of RSSI values from the same and/or related equipments (e.g., mobile devices by the same manufacturer, mobiles devices using the same or related types of radio chipset, mobile devices using the same and related operating systems, mobile device antenna, etc.) may be normalized using the same normalization function, while a different group of RSSI values from the same and/or related equipments may be normalized using a different one normalization function. For example, it may be identified, detected, and/or discovered that certain RSSI values were transmitted from a same type of equipment (e.g., Apple iPhones with the same model number, radio chipset, and antenna). Such RSSI values may be normalized by the same normalization function while other devices may be normalized using a different normalization function (e.g., based on the other devices' equipment types). In an embodiment, devices with unknown identifications may be grouped and normalized using a generic normalization function.

In an embodiment, all devices (regardless of equipment type) may be normalized using the same generic normalization function. For example, it may be anticipated (or generally statistically likely) that the crowd of mobile devices used in some application may contain a mixture of various equipment types. A generic normalization function that works with different various equipment types may at least decrease general RSSI value differences that may be attributed to different equipment types (e.g., normalize RSSI values towards an average equipment type). This may be advantageous to decrease the number of equipment type analysis, normalization processing, and/or other processing. Further, using one normalization function may help improve the consistency of the normalized RSSI values (e.g., there may not be enough equipment of one type to fit a normalization function for that specific type). In an embodiment, the generic normalization function may be pre-determined or fitted as needed during the performance of an application.

In an embodiment, one or more normalization functions may be pre-determined from tests prior to a performance of an application. For example, tests may be performed to determine for a room with one or a combination of various equipment types typical for the application (or the actual room for the application). In an embodiment, tests may be performed in a generic room for various applications (or to be used generically when the mom for the application is unknown. In an embodiment, the tests may be performed with various time intervals (of 1310) to obtain the normalization functions.

In an embodiment, the RSSI values may be analyzed and/or sorted to remove certain outliers prior to normalization, which may provide more precise and consistent dataset of RSSI values or for other purposes.

In another embodiment, the RSSI values may not need to be normalized, and the raw RSSI value may be used as inputs for the location coordinate evaluations in the wireless location method 1300.

The wireless location method 1300 performs location coordinate evaluation of nodes using the normalized RSSI values 1330.

In an embodiment, the location coordinate evaluation may be performed by various machine learning techniques as known now or may be later derived on the normalized RSSI values. For example, the location coordinate evaluation may be performed by a self-organizing map (SOM) on the normalized RSSI values (e.g., in a matrix form). The SOM takes in parameters of the normalized RSSI values, learning rate, and sigma. Other techniques such as manifold learning (e.g., MDS) and artificial neural networks (e.g., neural gas) may be used.

In an embodiment, the SOM may use pre-determined parameters (e.g., learning rate and/or sigma) as inputs that were pre-determined to have low error rates. For example, tests may be performed in a room with a number of nodes (e.g., mobile devices) in known positions. Various ranges of parameter (e.g., learning rate and/or sigma) may be used as input to the SOM with the normalized RSSI values. The output of the SOM may then be compared with the known positions of the nodes to determine the parameters that would yield the lowest error rate. The pre-determined parameters may be used as inputs for other location coordinate evaluations (e.g., with other nodes) at unknown positions.

In an embodiment, the SOM may be a residual sum of squares measurement as the error (e.g., based on the coordinates of the nodes at their actual coordinates). It is noted that an error measurement based on the actual coordinates may include a weight towards errors of nodes that are further apart (e.g., when the greater error of nodes further apart are amplified compared with nodes closer apart). In an embodiment, a sequence error may be used (e.g., one that considers error in the orientation (e.g., relative position) but less on the spacing (e.g., actual coordinates)), which may be preferable for applications that considers the orientation or relative positions of the nodes more important.

In another embodiment, a variable error may be used (e.g., one that considers a clustering of the evaluated nodes and may pull nodes further apart if clustering is large). For example, the space of the evaluated coordinates may be separated into individual boxes covering a certain area of the space. If the evaluated node cluster (e.g., having more than one node in a space), the error may increase depending on the degree of clustering (e.g., number of nodes in an area). This error evaluation may be helpful for testing or other applications where the nodes have a known or expected degree of clustering or non-clustering.

In an embodiment, tests may be performed in a generic room for various applications (or to be used generically when the room for the application is unknown).

In other embodiments, the location coordinate evaluation may use other machine learning techniques or may use non-machine learning techniques (e.g., regression analysis, force directed graph drawings as discussed above, or other techniques).

The wireless location method 1300 orients the evaluated location coordinates 1340. It is noted that in some location coordinate evaluation (e.g., SOM), the correct orientation of the crowd of nodes is not evaluated. In an embodiment, the location coordinates may be oriented using singular value decomposition or other techniques as known now or may be later derived. In an embodiment, the correct orientation of the location coordinate may not be needed (e.g., in an application where only the relative positions among the nodes would want to be ascertained).

In an embodiment, the orientation may be performed and/or assisted by GPS and/or other wireless location techniques. For example, GPS may be used to estimate a less precise (but with absolute coordinates) position of one or more nodes (including nodes that are farther apart). Therefore, the orientation between some of the nodes may be estimates (e.g., using the absolute coordinates) using the GPS (or other wireless location techniques) and a more precise orientation (using evaluated location coordinates) may be based on the estimated orientation.

In an embodiment, the orientation may be performed with respect to one of the nodes (e.g., a lead node).

The wireless location method 1300 performs the application using the oriented location coordinates of the nodes 1350.

In an embodiment, the oriented location coordinates of the nodes (e.g., of mobile devices) may be used to arrange a coordinated display (e.g., arranging a lightshow using the mobile devices at their location). For example, each mobile device contains software (e.g., an app) which can control the display of the mobile device. The software may be in communication with a server that has access to the oriented location coordinates of the mobile devices. The server may use the oriented location coordinates to have the relevant mobile device at a location to change to a certain display, such that the individual displays of the mobile devices may make up a larger display over the area (e.g., the room or the crowd). For example, the displays in conjunction may be controlled to display certain patterns of color, as pixels of large images, or other displays. In an embodiment, the displays may change over time to portray changing images, changing colors, animation, or other motions in the display. In an embodiment, a sync time (e.g., communication time between the mobile devices and the server or other communication lag events) may need to be accounted for (e.g., when the display is fast-changing and would need to be synced with lower tolerance to prevent perceptible lags). For example, a uniform lag time (or buffer) may be used to allow for the communication lag so that all of the displays sync to the common lag time. In an embodiment, the server may be in communication with a controller (e.g., a DJ station) which may automatically or manually issue control to the individual mobile devices (e.g., having the lightshow sync to a song that is being played or will be played). In an embodiment, the data transfer and computation (e.g., at least a portion performed by the serve) may be performed by and/or within a mesh of at least some of the nodes (e.g., a BLUETOOTH mesh).

In an embodiment, locations from GPS or other wireless location system may assist and/or supplement with the wireless location method. For example, when a node is out of wireless communication range (for obtaining the RSSI values) with a subset of nodes, GPS (having an accuracy of 5 m) or other location wireless system may be used in conjunction with RSSI values data for all of the nodes (e.g., another node that is its range with both the node and at least a subset of the subset of nodes) to position the node. In an embodiment, the wireless location method may work with sub-meter range nodes (e.g., 0.2 m ranges for a room packed with human operators carring nodes) and also nodes in larger rooms through the combination of the wireless location method, and/or other location system (e.g., 100 m (range of BLUETOOTH) or larger).

It is noted that certain "location" problems may be solved by video, e.g., things like a robot reconnecting server chords, a surgical bot trying sutures, or a tractor trailer harvesting wheat. Embodiments may be complementary to these locations, in organizing identities (e.g., who is who where?).

In other embodiments, the wireless location method as disclosed herein may be applicable to other applications, including:

Tracking Agricultural Machine Movements (e.g., Tracking Positions All Your Tractors):

In one embodiment, tractors, semi-trailers, drones, small task bots, or other modernized farm equipment may be coordinated to farm with greater autonomy. An advantage is the accurate positioning of farm devices even to very small granularity, e.g. knowing semi-trailer and tractor pairs in the field, accountability of farmhand to his/her equipment, etc. It is noted that such resolution of position is beyond capabilities of GPS in a case where several devices are near each other, e.g. in a barn, equipment staging for the day, in a warehouse, or some cases of closely coordinated field work. In an embodiment, machines movement may be directed in agricultural environments where GPS is inaccessible and/or inadequate, e.g., wine cellars, warehouses, underground storage, urban farms, etc.

Tracking Underground Machine Movements (e.g., Mining Machines, Tracking Positions of Drills that are Moving Underground, etc.):

An embodiment may apply to autonomous, underground machine movements. GPS cannot penetrate the earth and therefore underground environments such as mines, quarries, storage facilities, and others require some system for coordination and localization. In an embodiment, location services can be provided without the need for a reference frame as the devices themselves are the reference points.

Tracking Industrial Vehicle Movements:

In one embodiment, machines and devices on a worksite can be organized by location without input from workers. An advantage is the granularity of accuracy allowing for accurate knowledge of accountability, culpability, and movement of devices and their relation to humans. For example, if a worker improperly attaches a trailer to his/her truck, such data may be immediately detected and be available to management. In another use case, if specific equipment is required to move from one side of the worksite to the other without human input, the equipment can be called upon and make delivery of itself in any environment including underground, warehouses, hulls of ships, docks, storage facilities, quarries, mines, underwater, etc. Industrial vehicles include drones, submarines, tractors, trucks, robots, semi-trailers, trailers, forklifts, diggers, dredgers, tug boats, winches, cranes, crane cabs, sky lifts, drones, backhoes excavators, and any other machine or device that may be found on a worksite of any scale.

Tracking Locations of Animals and Fishes (e.g., Attach a Module to the Animals and Research their Movements, their Communication with One Another):

An embodiment can be used to count, localize, signal, and direct herd animals or fish. For example, it could be used to herd sheep or cattle when attached to a vibrating/shock collar.

Tracking and Finding Items (e.g., Pixie (http://getpixie.com/))

In one embodiment, a plurality of devices can be used to locate a specific device within the crowd.

Tracking Planes at Airports:

An embodiment can be used to organize airplanes by identifier on airport ramps for the purpose of alerting ATC and Ground Control to the identity and location of each plane passively and without visual recognition, which may be particularly useful in congested airports and/or low visibility operations.

Tracking Shoppers Location in a Store:

An embodiment can be used to database the location of persons in any store including their identity.

Tracking Movement of Current in River Via Multiple Sensors Movement:

In an embodiment, the location of the sensors may be organized.

Self Organized and Location Based Reporting of Agricultural Field Sensors:

In one embodiment, any sensor network could self-organize, which may negate the need for an IT professional to specifically coordinate sensors or establish specific connections between sensors. For example, a lighting team could simply install at random enabled lights in a room and the disclosed art would record the position of all sensors providing location based functionality and control. Agriculture is increasingly deploying field sensors to monitor the specific needs of crops to increasingly small resolutions, deploying these sensors enabled with the embodiment would be extremely simple compared with the detailed location setup required today. Self-organizing sensors as made possible by the present disclosure also apply to car parking lots, warehouse storage systems, freight cargo box organization/coordination, managing access points in buildings of any size, etc.

Self-Driving Car Identity Based Communications (Letting One Car Communicate with the Car Adjacent, or in Front and Adjacent without Relying on Visuals):

In an embodiment, self-driving cars may be made aware of the identification of surrounding self-driving cars. An exemplary application is the settlement of insurance claims, e.g. should two cars damage each other but continue driving, both cars are immediately made aware of the other car's information. It may also be used to establish a network for the purpose of casual chat, information transfer, and other identity and location based network services.

Crowd Control at Events:

An embodiment may be used at events for crowd control, interaction, and monitoring purposes. For example, treating smart phones as nodes the phones can be networked to direct individuals toward their interest with the traffic interest of the crowd at large in consideration. Inefficiencies in crowd movement can be spotted and mitigated. Furthermore, ticketed events could be managed without walls or fences by way of identity based policing. If a person is not recognizable to the system or not appearing by way of location where they ought to be appearing, than managers can remove the person or deny services.

Interacting with Virtual Reality Based on Where You Are and Who You are with:

In an embodiment, UI components or digital assets can be presented to a user in response to their surrounding environment, e.g., an adjacent user may have an avatar, a specific venue may have a food and drink ordering system that changes with location.

In Venue or Event Food, Merchandise, and/or Drink Delivery:

In one embodiment, any good or service requiring delivery at an outdoors or indoors event or venue or locale can be accurately routed using the art.

Store Inventory Protection:

In one embodiment, the disclosed art can be used to alert store owners to the unwanted disappearance of an item.

In embodiments, the wireless location method as disclosed herein may be applicable to other applications, including:

Self-driving car identity based communications (letting one car communicate with the car adjacent, or in front and adjacent without relying on visuals)

Self organized sensors for IT professionals managing access points in large buildings Self organizing storage warehouse Car lot map creation Crowd movement data Allow for fenceless venues or events (but still controlled attendance)

Replace ID cards for location entry, emergency services, and data collection

ATC location organization without radar (flights over the ocean, planes already equipped with their own radar— only valuable to close flying planes or if satellites are not an option (uncharacteristically dense and high clouds)

Underwater fleet management

Line weighting applications (if a line forms at a place, alert authority to resolve bottleneck)

Self driving car traffic, concessions or rides, venue bathrooms, etc.

Emergency routing for victims and action personnel

Automatically establishing a line for bot systems based on identity

Calculate an efficient traffic movements (e.g., based on "Bernoulli's principle")

Book organization and finding system (e.g., at a library)

Presenting UI based on where you are and what is around you

Satellite orientation and organization

Tracking people traveling, e.g., remote places with or without cellular connections (like mountain hiking, extremely remote locations such as deserts, rainforests, North or South poles), where the travelers can keep track of one another Tracking self-driving vehicles on the road (e.g., solving an identity problem whereas video alone may solve the driving problem)

In another embodiment, the wireless location methods as disclosed herein may be used for other applications that may be handled by GPS or other wireless locations methods. It is noted that GPS hardware and chips are usually much more costly than most other radio modules (e.g., that has measurable RSSI) like BLE hardware and chips.

EXAMPLES

Without intending to limit the scope of the invention, the following examples illustrate how various embodiments of the invention may be made and/or used.

Various tests were performed using various mobile phones arranged in known positions within a space. The mobile phones were configured to transmit wireless signals, and other mobile phones within space were configured to receive the wireless signals and determine the corresponding RSSI values within a time interval. The collected RSSI values were aggregated and normalized according to an exponential fit of the RSSI value data, after outliers were removed. The normalized RSSI values were passed to a SOM for unsupervised machine learning using various parameters for the learning rate and sigma value, resulting in evaluated location coordinates based on the normalized RSSI values. The evaluated location coordinates were oriented to an orientation comparable with the original known positions using singular value decomposition. The oriented location coordinates (for each of the test configurations and SOM parameters) were compared with the original known positions to determine an error to the original known positions for the given test configurations and SOM parameters.

Table 21 lists the mobile devices use in the tests.

TABLE 21

| Phone # | SOFTWARE | HARDWARE | RADIO (WI-FI or 4G LTE) |
| --- | --- | --- | --- |
| 1 | Andriod | Sprint Moto E (2nd Gen) with 4G LTE XT1526 | WI-FI |
| 2 | Andriod | Sprint Moto E (2nd Gen) with 4G LTE XT1527 | WI-FI |
| 4 | Andriod | Sprint Moto E (2nd Gen) with 4G LTE XT1528 | WI-FI |
| 5 | Andriod | Sprint Moto E (2nd Gen) with 4G LTE XT1529 | WI-FI |
| 6 | Andriod | Sprint Moto E (2nd Gen) with 4G LTE XT1530 | WI-FI |
| 7 | Andriod | Sprint Moto E (2nd Gen) with 4G LTE XT1531 | WI-FI |
| 8 | Andriod | Sprint Moto E (2nd Gen) with 4G LTE XT1532 | WI-FI |
| 9 | Andriod | Sprint Moto E (2nd Gen) with 4G LTE XT1533 | WI-FI |
| 10 | Andriod | Sprint Moto E (2nd Gen) with 4G LTE XT1534 | WI-FI |
| 11 | Andriod | Sprint Moto E (2nd Gen) with 4G LTE XT1535 | WI-FI |
| 12 | Andriod | Sprint Moto E (2nd Gen) with 4G LTE XT1536 | WI-FI |
| 13 | Andriod | Sprint Moto E (2nd Gen) with 4G LTE XT1537 | WI-FI |
| 14 | Andriod | Sprint Moto E (2nd Gen) with 4G LTE XT1538 | WI-FI |
| 15 | Andriod | Sprint Moto E (2nd Gen) with 4G LTE XT1539 | WI-FI |
| 17 | Andriod | Sprint Moto E (2nd Gen) with 4G LTE XT1540 | WI-FI |
| 18 | Andriod | Sprint Moto E (2nd Gen) with 4G LTE XT1541 | WI-FI |
| 20 | Andriod | Sprint Moto E (2nd Gen) with 4G LTE XT1542 | WI-FI |
| 21 | Andriod | Sprint Moto E (2nd Gen) with 4G LTE XT1543 | WI-FI |
| 22 | Andriod | Sprint Moto E (2nd Gen) with 4G LTE XT1544 | WI-FI |
| 23 | IOS | Iphone 7 With Defender Otter Box (MNAU2LL/A) | 4G LTE |
| 24 | Andriod | Galaxy S6 (SAMSUNG-SM-G920A) | WI-FI |
| 25 | IOS | Iphone 6s With Thin Plastic Case (MKQA2LL/A) | 4G LTE |

TABLE 21-continued

| Phone # | SOFTWARE | HARDWARE | RADIO (WI-FI or 4G LTE) |
|---|---|---|---|
| 26 | Andriod | Galaxy S7 (SAMSUNG-SM-G930A) | WI-FI |
| 27 | IOS | Iphone 5 With Defender Otter Box (MD654LL/A) | WI-FI |
| 28 | Andriod | Galaxy S5 (SAMSUNG-SM-G900A) | WI-FI |
| 29 | IOS | Iphone 6 (MG5W2LL/A) | WI-FI |
| 30 | Andriod | Galaxy S5 (SAMSUNG-SM-G900A) | WI-FI |
| 31 | IOS | Iphone 5S (ME307LL/A) | WI-FI |
| 32 | Andriod | Galaxy S6 (SAMSUNG-SM-G920A) | WI-FI |
| 33 | IOS | Iphone 5 (MD638LL/A) | WI-FI |

FIG. 14A illustrates an arrangement of nodes for Test A according to an embodiment.

For Test A, the mobile devices (as listed in Table 21) are arranged 0.5 m (~19.685 inch) by 12 inch apart (e.g., close cluster), at a uniform height, with similar devices close to each other. It is noted that mobile device 30 only received RSSI values (and did not transmit), and mobile device 5 was malfaunctioning and gave false readings.

Figure 14B:
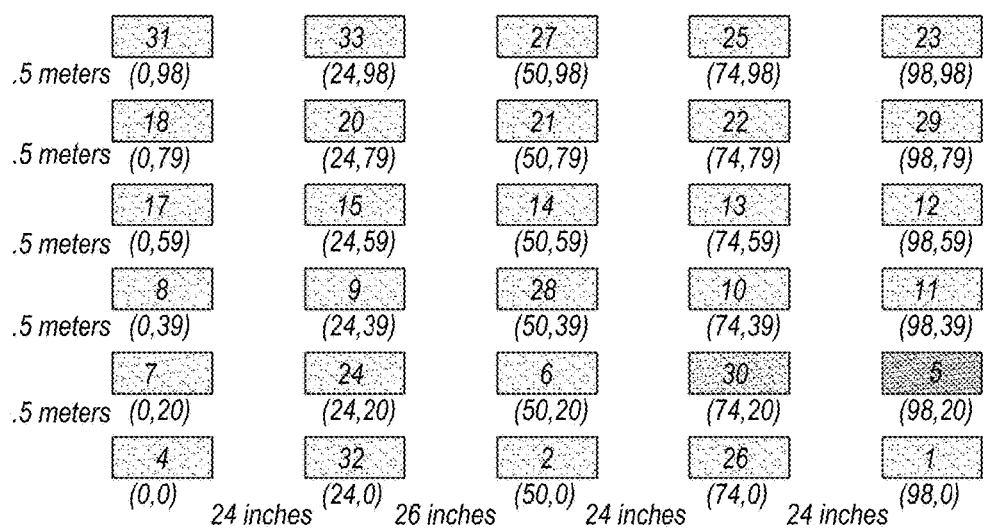
FIG. 14B illustrates an arrangement of nodes for Test B according to an embodiment.

FIG. 14B illustrates an arrangement of nodes for Test B according to an embodiment.

For Test B, the mobile devices (as listed in Table 21) are arranged 0.5 m (~19.685 inch) by 24 to 25.5 inch apart (e.g., far cluster), at a uniform height, with similar devices close to each other. It is noted that mobile device 30 only received RSSI values (and did not transmit), and mobile device 5 was malfunctioning and gave false readings.

Figure 14C:
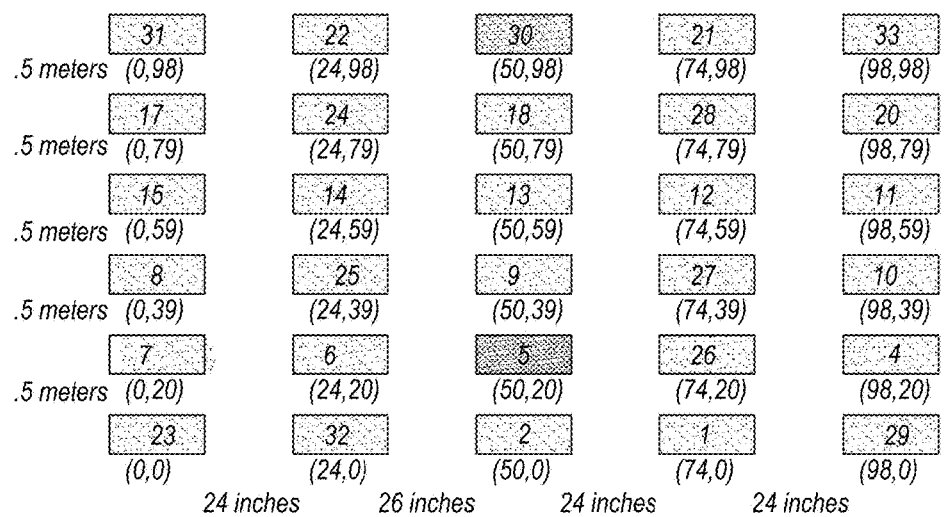
FIG. 14C illustrates an arrangement of nodes for Test C according to an embodiment.

FIG. 14C illustrates an arrangement of nodes for Test C according to an embodiment.

For Test C, the mobile devices (as listed in Table 21) are arranged 0.5 m (~19.685 inch) by 24 to 25.5 inch apart (e.g., far cluster), at a uniform height, with devices of different equipments intermixed in their arrangement. It is noted that mobile device 30 only received RSSI values (and did not transmit), and mobile device 5 was malfunctioning and gave false readings.

Figure 14D:
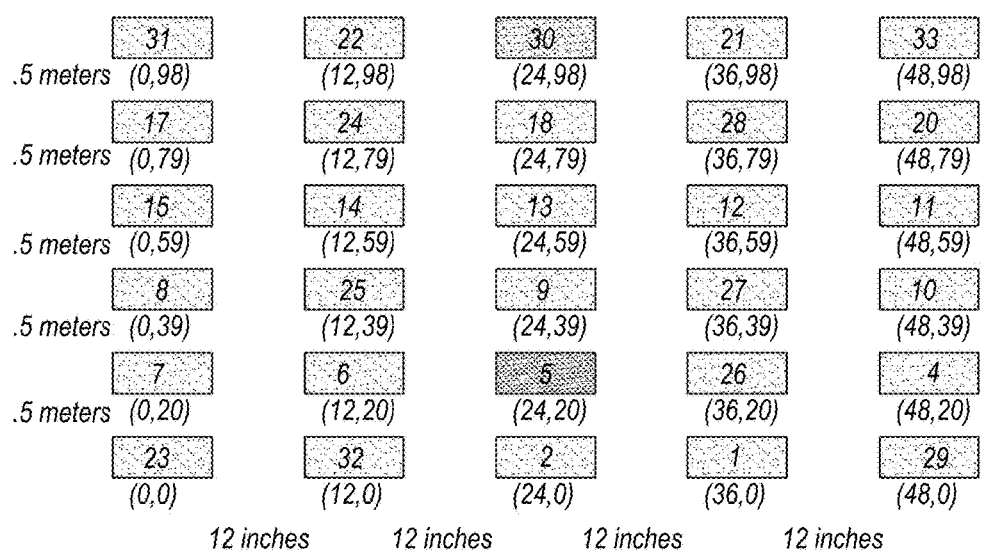
FIG. 14D illustrates an arrangement of nodes for Test D according to an embodiment.

FIG. 14D illustrates an arrangement of nodes for Test D according to an embodiment.

For Test D, the mobile devices (as listed in Table 21) are arranged 0.5 m (~19.685 inch) by 12 inch apart (e.g., close cluster), at a uniform height with devices of different equipments intermixed in their arrangement. It is noted that mobile device 30 only received RSSI values (and did not transmit), and mobile device 5 was malfunctioning and gave false readings.

Figure 15A:
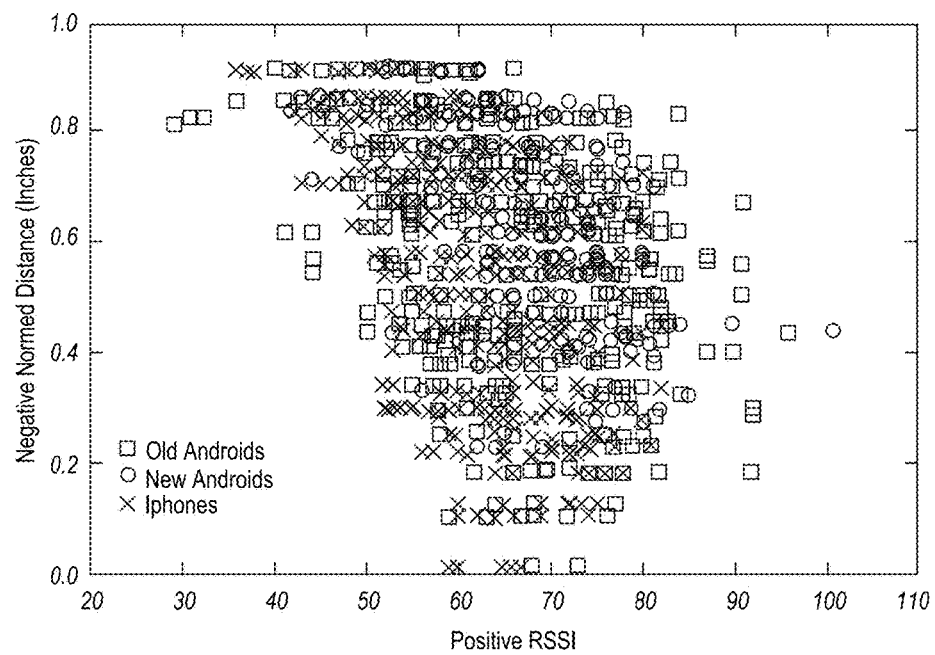
FIG. 15A illustrates a graph showing measured relationship between RSSI value and distance for Tests A-D with 5 sec RSSI reading interval.

FIG. 15A illustrates a graph showing measured relationship between RSSI value and distance for Tests A-D with 5 sec RSSI reading interval.

With the equipments listed in Table 21 under Tests A, the received RSSI value (at each equipment) from the transmitting equipments are measured and plotted in FIG. 15A with respect to their known distances to the transmitting equipment. The distances were normalized to be between zero and one.

It is noted that the equipments (in Table 21) can grouped by the equipment type (old Android devices, new Android devices, and Iphones), as shown in FIG. 15A.

Figure 15B:
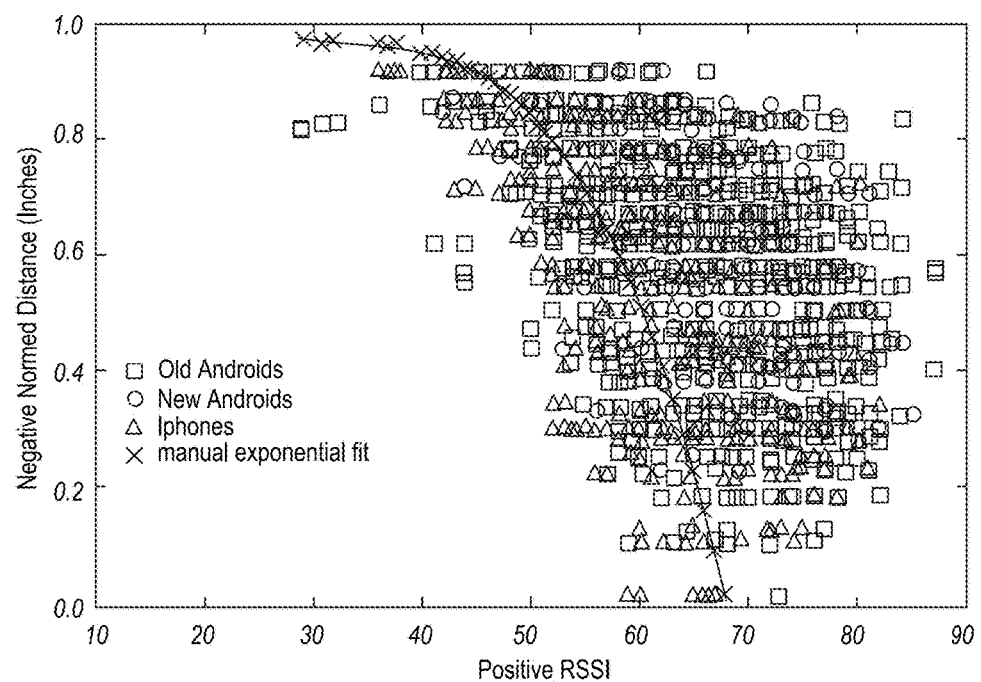
FIG. 15B illustrates a graph showing measured relationships between RSSI value and distance with an exponential fit of the graph for tests A-D with 5 sec RSSI reading interval.

FIG. 15B illustrates a graph showing measured relationship between RSSI value and distance with an exponential fit of the graph for Tests A-D with 5 sec RSSI reading interval.

An exponential fit may be used for the measured relationship between RSSI value and distance for Tests A-D. As discussed with respect to wireless location method 1300, the fit may be used to normalize other RSSI value measurements in future instances (e.g., when distance is unknown and wants to be determined).

Figure 15C:
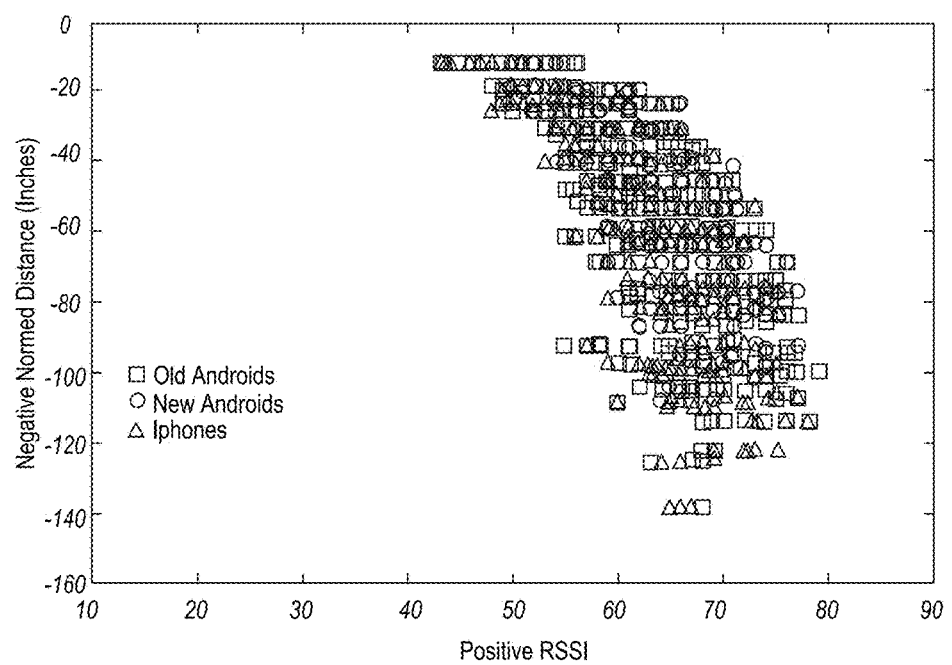
FIG. 15C illustrates a graph showing measured relationship between RSSI value and distance with outliers removed for Tests A-D with 5 sec RSSI reading interval.

FIG. 15C illustrates a graph showing measured relationship between RSSI value and distance with outliers removed for Tests A-D with 5 sec reading interval.

It is noted that with outliers removed, a fit may be closer to the plot (e.g., has less error).

Figure 15D:
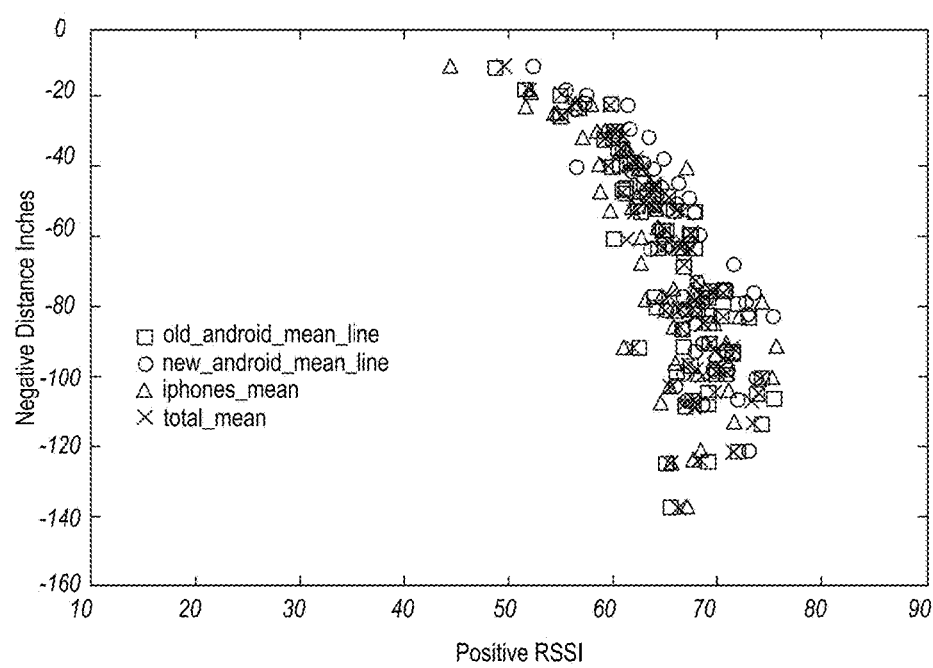
FIG. 15D illustrates a graph showing measured relationship between RSSI value and mean distances with outliers removed for Tests A-D with 5 sec RSSI reading interval.

FIG. 15D illustrates a graph showing measured relationship between RSSI value and mean distances with outliers removed for Tests A-D with 5 sec RSSI reading interval.

The plot of the measured relationship between RSSI value and distances may be further refined with mean distances. Here, RSSI values from transmitting equipments of the same type and with the same (or similarly close) distances to the receiving equipment were combined (averaged). Further, RSSI values from all transmitting equipments with the same (or similarly close) distances to the receiving equipment were separately combined (averaged). It is noted that a fit to this plot would have less error than the previous plots (because of less data points across similar distances).

Figure 15E:
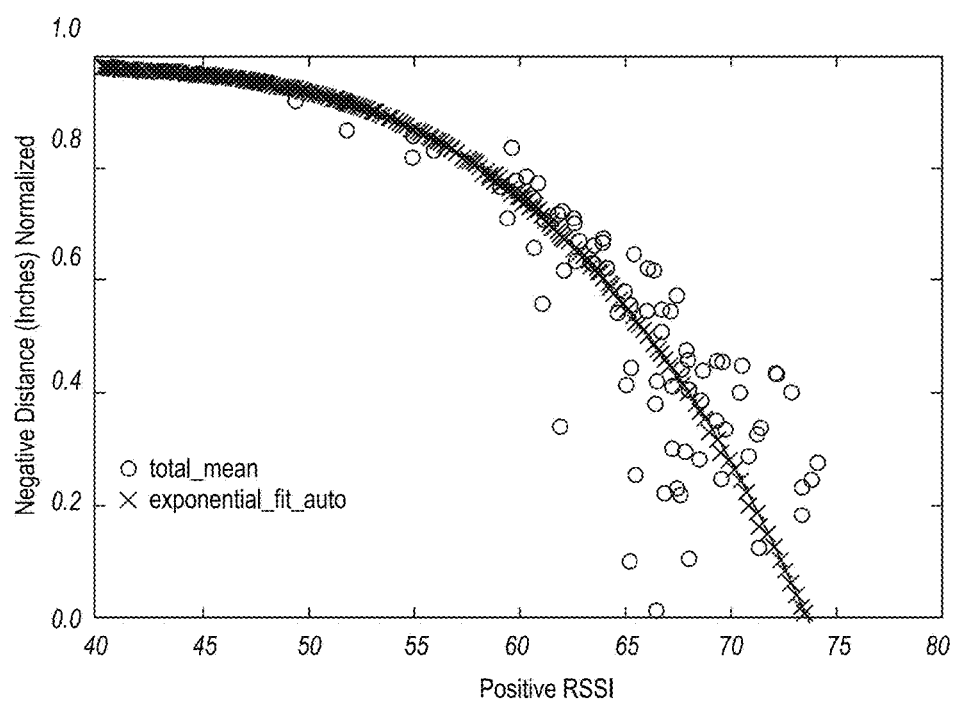
FIG. 15E illustrates a graph showing measured relationship between RSSI value and total mean distances with outliers removed and an exponential fit of the graph for Tests A-D with 5 sec RSSI reading interval.

FIG. 15E illustrates a graph showing measured relationship between RSSI value and total mean distances with outliers removed and an exponential fit of the graph for Tests A-D with 5 sec RSSI reading interval.

Here, the plot shows the average RSSI values from all transmitting equipments with the same (or similarly close) distances to the receiving equipment. An exponential fit was made to the plot.

Figure 16:
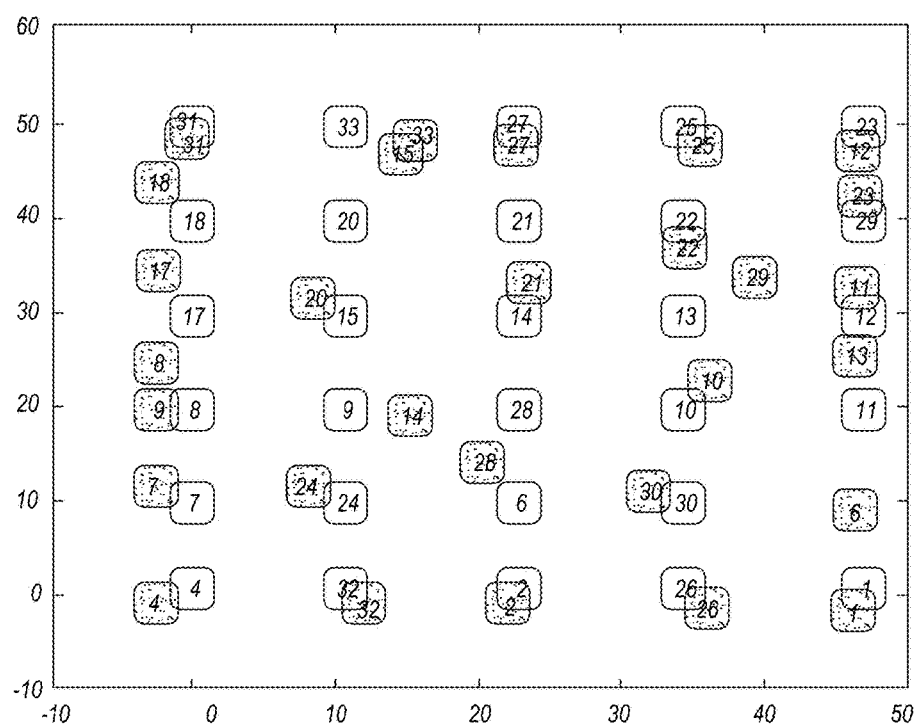
FIG. 16 illustrates exemplary comparison between positions of nodes to SOM evaluated positions (without orientation) for Test B with 5 sec RSSI reading interval.

FIG. 16 illustrates an exemplary comparison between positions of nodes to SOM evaluated positions (without orientation) for Test B with 5 sec RSSI reading interval.

SOM evaluations were performed for the mobile phone arrangements of Test B (using the normalized measured distances as discussed with respect to FIGS. 15A-15E). The resulting SOM evaluations results were compared with the known positions of the mobile devices arrangement of Test A.

Figure 17A:
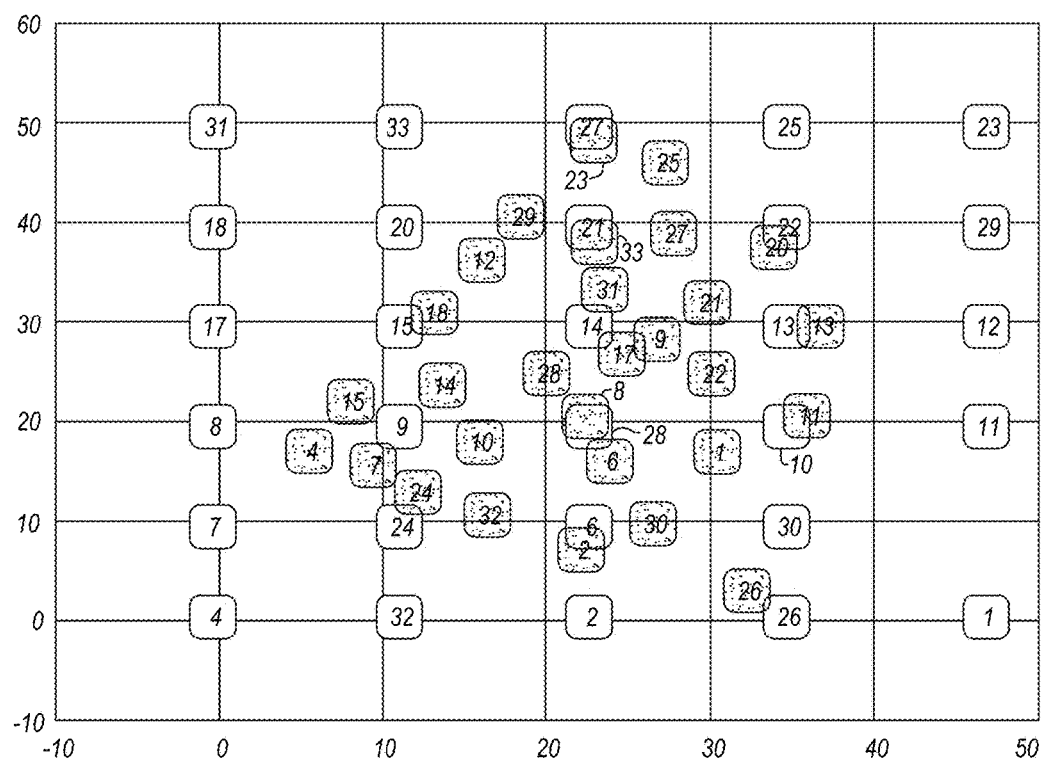
FIG. 17A illustrates a comparison between positions of nodes to SOM evaluated positions after orientation for Test A with 5 sec RSSI reading interval.

FIG. 17A illustrates a comparison between positions of nodes to SOM evaluated positions after orientation for Test A with 5 sec RSSI reading interval.

SOM evaluations were performed for the mobile phone arrangements of Test A (using the normalized measured distances as discussed with respect to FIGS. 15A-15E). The SOM evaluations were then oriented using singular value decomposition. The resulting oriented SOM evaluations results were compared with the known positions of the mobile devices arrangement of Test A.

Referring to FIG. 17A, the SOM evaluation illustrated in FIG. 17A was performed with the following parameters: learning rate—0.16 and sigma—3.0 for 300 iterations. The SOM error was 8235.

Figure 17B:
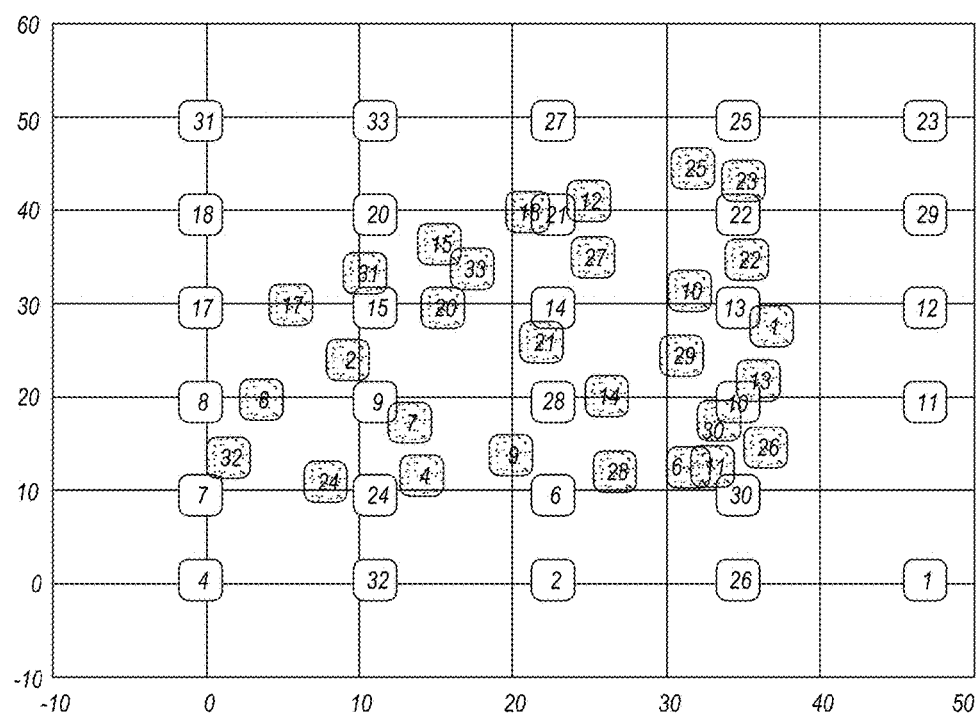
FIG. 17B illustrates a comparison between positions of nodes to SOM evaluated positions after orientation for Test B with 5 sec RSSI reading interval.

FIG. 17B illustrates a comparison between positions of nodes to SOM evaluated positions after orientation for Test B with 5 sec RSSI reading interval.

SOM evaluations were performed for the mobile phone arrangements of Test B (using the normalized measured distances as discussed with respect to FIGS. 15A-15E). The SOM evaluations were then oriented using singular value decomposition. The resulting oriented SOM evaluations results were compared with the known positions of the mobile devices arrangement of Test B.

Referring to FIG. 17B, the SOM evaluation illustrated in FIG. 17B was performed with the following parameters: learning rate—0.16 and sigma—3.0 for 300 iterations. The SOM error was 6622.

Figure 17C:
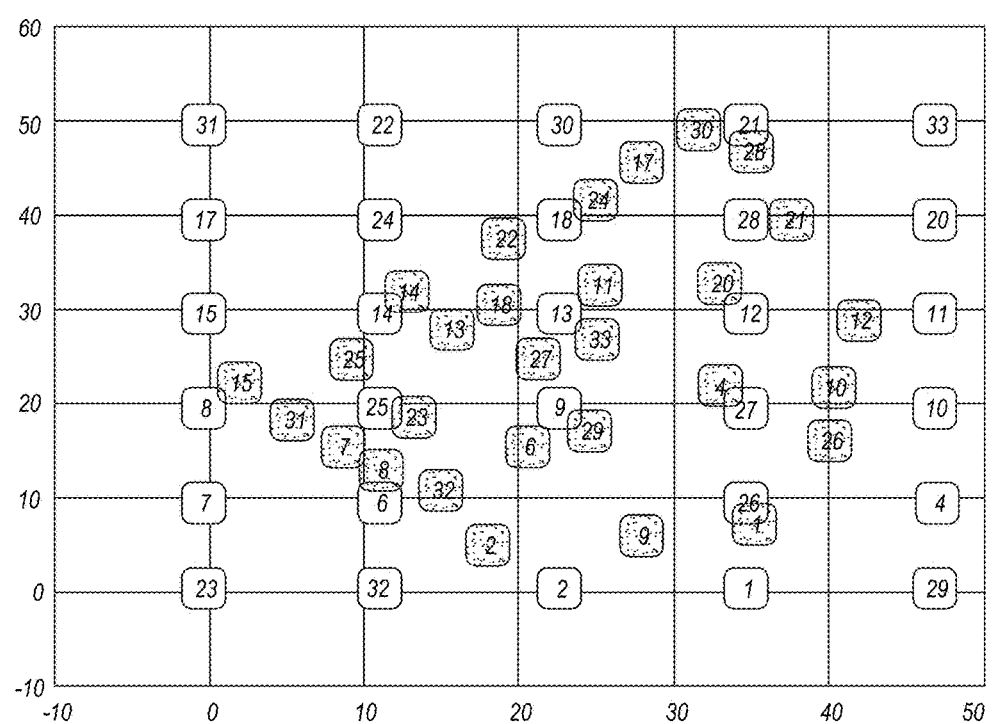
FIG. 17C illustrates a comparison between positions of nodes to SOM evaluated positions after orientation for Test C with 5 sec RSSI reading interval.

FIG. 17C illustrates a comparison between positions of nodes to SOM evaluated positions after orientation for Test C with 5 sec RSSI reading interval.

SOM evaluations were performed for the mobile phone arrangements of Test C (using the normalized measured distances as discussed with respect to FIGS. 15A-15E). The SOM evaluations were then oriented using singular value decomposition. The resulting oriented SOM evaluations results were compared with the known positions of the mobile devices arrangement of Test C.

Referring to FIG. 17C, the SOM evaluation illustrated in FIG. 17C was performed with the following parameters: learning rate—0.16 and sigma—3.0 for 300 iterations. The SOM error was 7347.

Figure 17D:
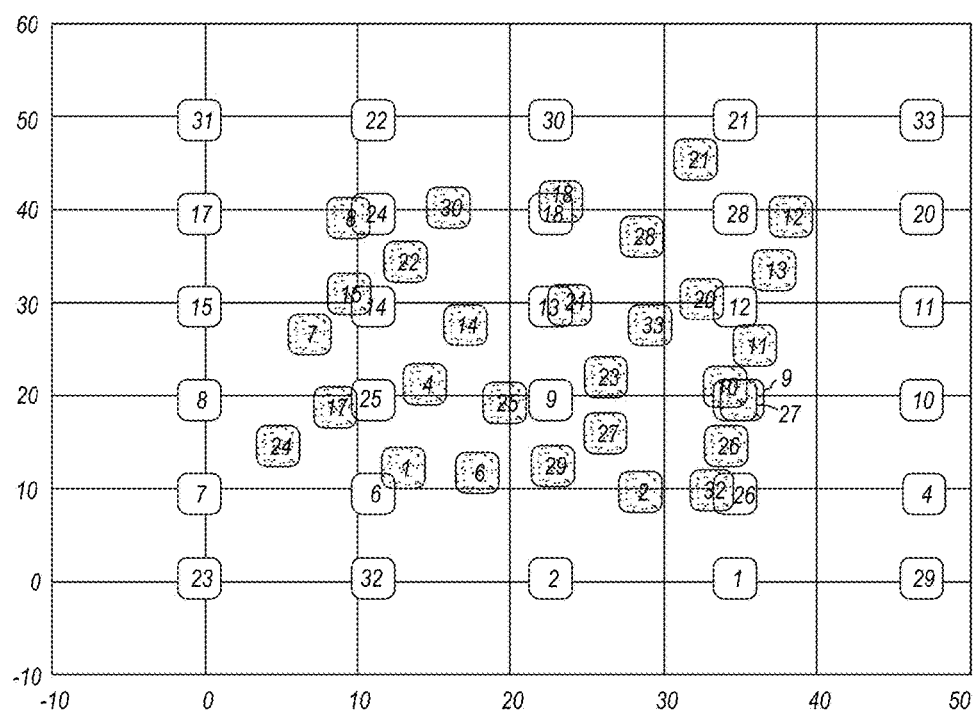
FIG. 17D illustrates a comparison between positions of nodes to SOM evaluated positions after orientation of Test D with 5 sec RSSI reading interval.

FIG. 17D illustrates a comparison between positions of nodes to SOM evaluated positions after orientation for Test D with 5 sec RSSI reading interval.

SOM evaluations were performed for the mobile phone arrangements of Test D (using the normalized measured distances as discussed with respect to FIGS. 15A-15E). The SOM evaluations were then oriented using singular value decomposition. The resulting oriented SOM evaluations results were compared with the known positions of the mobile devices arrangement of Test D.

Referring to FIG. 17D, the SOM evaluation illustrated in FIG. 17D was performed with the following parameters: learning rate—0.16 and sigma—3.0 for 300 iterations. The SOM error was 10042.

Figure 18A:
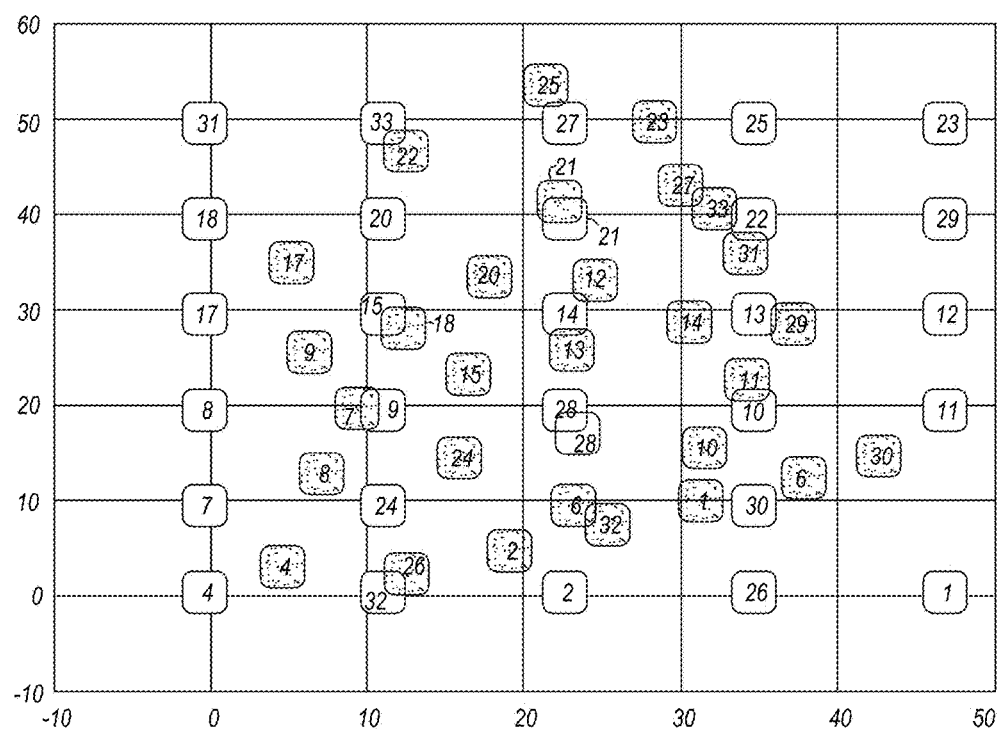
FIG. 18A illustrates a comparison between positions of nodes to SOM evaluated positions after orientation for Test A with 30 sec RSSI reading interval.

FIG. 18A illustrates a comparison between positions of nodes to SOM evaluated positions after orientation for Test A with 30 sec RSSI reading interval.

SOM evaluations were performed for the mobile phone arrangements of Test A (using the normalized measured distances as discussed with respect to FIGS. 15A-15E). The SOM evaluations were then oriented using singular value decomposition. The resulting oriented SOM evaluating results were compared with the known positions of the mobile devices arrangement of Test A.

Referring to FIG. 18A, the SOM evaluation illustrated in FIG. 18A was performed with the following parameters: learning rate—0.16 and sigma—3.0 for 600 iterations. The SOM error was 6548.

Figure 18B:
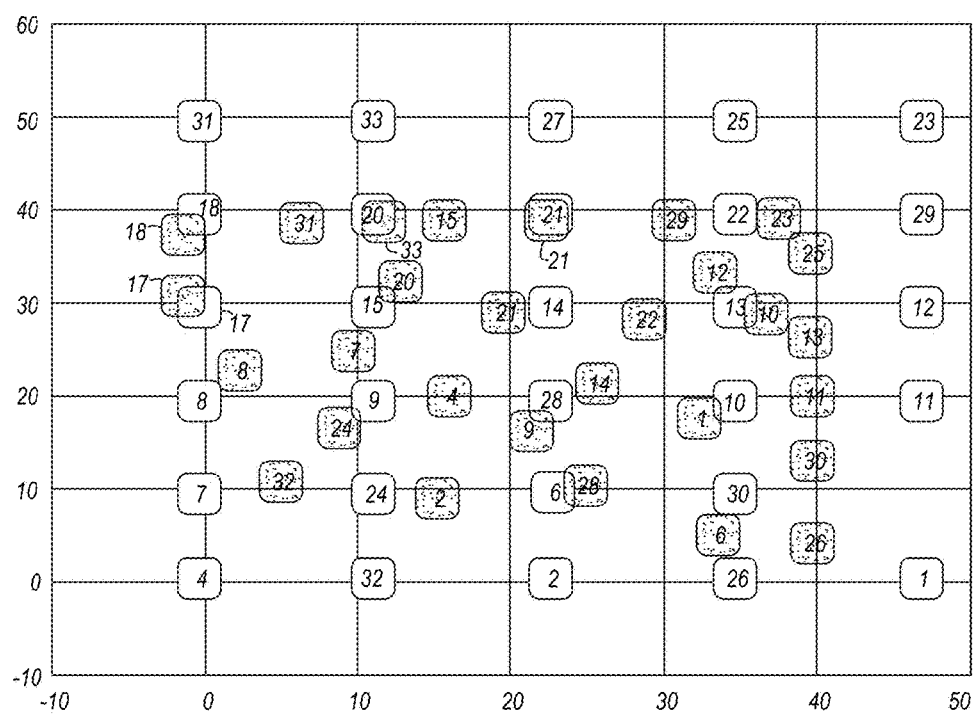
FIG. 18B illustrates a comparison between positions of nodes to SOM evaluated positions after orientation for Test B with 30 sec RSSI reading interval.

FIG. 18B illustrates a comparison between positions of nodes to SOM evaluated positions after orientation for Test B with 30 sec RSSI reading interval.

SOM evaluations were performed for the mobile phone arrangements of Test B (using the normalized measured distances as discussed with respect to FIGS. 15A-15E). Tb SOM evaluations were then oriented using singular value decomposition. The resulting oriented SOM evaluations results were compared with the known positions of the mobile devices arrangement Test B.

Referring to FIG. 18B, the SOM evaluation illustrated in FIG. 18B was performed with the following parameters: learning rate—0.16 and sigma—3.0 for 600 iterations. The SOM error was 4206.

Figure 18C:
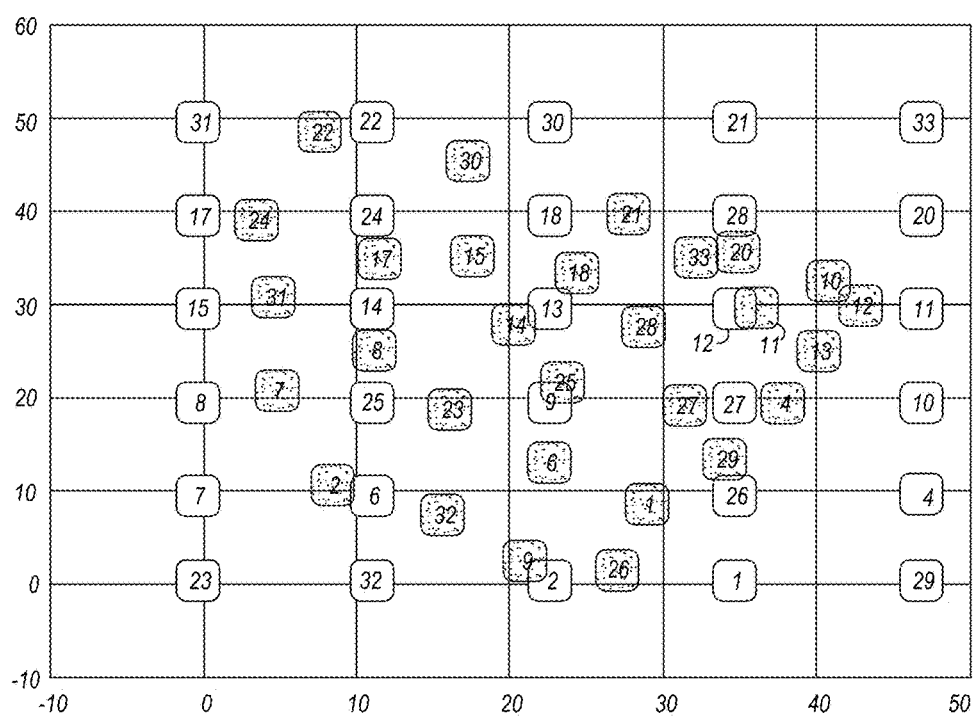
FIG. 18C illustrates a comparison between positions of nodes to SOM evaluated positions after orientation for Test C with 30 sec RSSI reading interval.

FIG. 18C illustrates a comparison between positions of nodes to SOM evaluated positions after orientation for Test C with 30 sec RSSI reading interval.

SOM evaluations were performed for the mobile phone arrangements of Test C (using the normalized measured distances as discussed with respect to FIGS. 15A-15E). The SOM evaluations were then oriented using singular value decomposition. The resulting oriented SOM evaluations results were compared with the known positions of the mobile devices arrangement of Test C.

Referring to FIG. 18C, the SOM evaluation illustrated in FIG. 18C was performed with the following parameters: learning rate—0.16 and sigma—3.0 for 600 iterations. The SOM error was 5418.

Figure 18D:
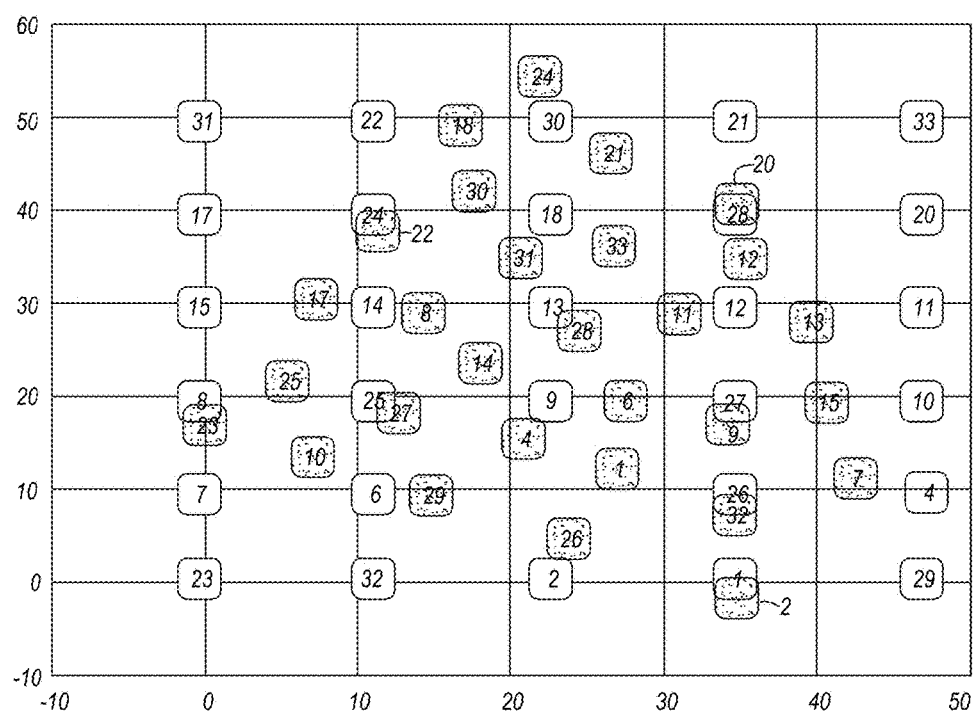
FIG. 18D illustrates a comparison between positions of nodes to SOM evaluated positions after orientations for Test D with 30 sec RSSI reading interval.

FIG. 18D illustrates a comparison between positions of nodes to SOM evaluated positions after orientation for Test D with 30 sec RSSI reading interval.

SOM evaluations were performed for the mobile phone arrangements of Test D (using the normalized measured distances as discussed with respect to FIGS. 15A-15E). The SOM evaluations results were compared with the known positions of the mobile devices arrangement of Test D.

Referring to FIG. 18D, the SOM evaluation illustrated in FIG. 18D was performed with the following parameters: learning rate—0.16 and sigma—for 600 iterations. The SOM error was 12895.

Figure 19A:
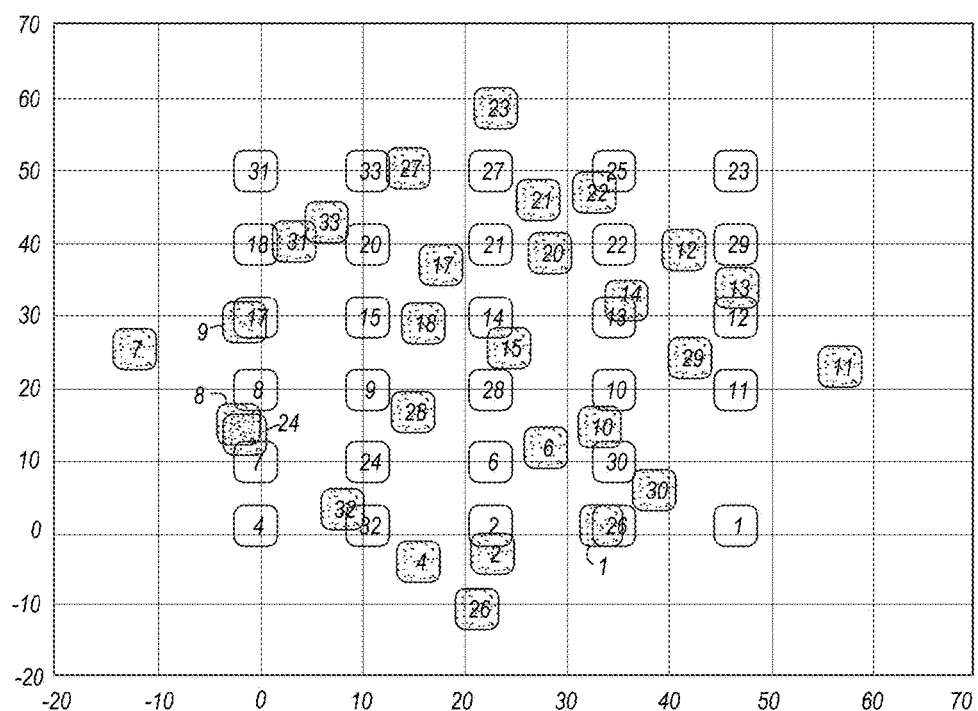
FIG. 19A illustrates a comparison between positions of nodes to SOM evaluated positions after orientation for Test A with 1 min RSSI reading interval.

FIG. 19A illustrates a comparison between positions of nodes to SOM evaluated positions after orientation for Test A with 1 min RSSI reading interval.

SOM evaluations were performed for the mobile phone arrangements of Test A (using the normalized measured distances as discussed with respect to FIGS. 15A-15E). The SOM evaluations were then oriented using singular value decomposition. The resulting oriented SOM evaluations results were compared to the known positions of the mobile devices arrangement of Test A.

Referring to FIG. 19A, the SOM evaluation illustrated in FIG. 19A was performed with the following parameters: learning rate—0.11 and sigma—9.0 for 800 iterations. The SOM error was 5063.

Figure 19B:
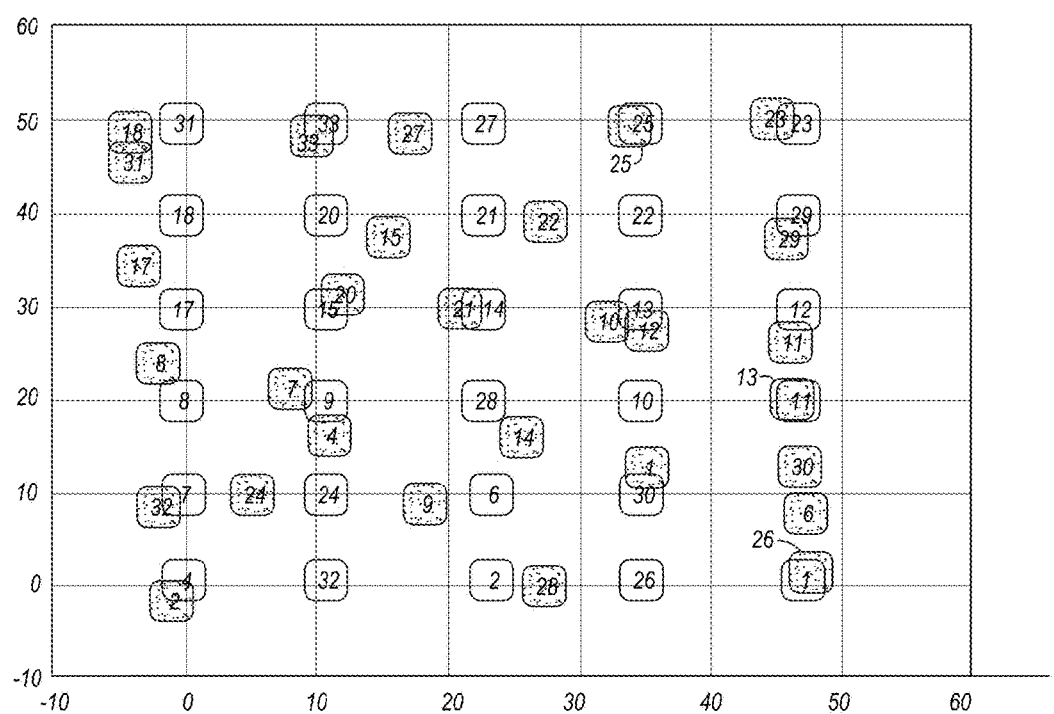
FIG. 19B illustrates a comparison between positions of nodes to SOM evaluated positions after orientation for Test B with 1 min RSSI reading interval.

FIG. 19B illustrates a comparison between positions of nodes to SOM evaluated positions after orientation for Test B with 1 min RSSI reading interval.

SOM evaluations were performed for the mobile phone arrangements of Test B (using the normalized measured distances as discussed with respect to FIGS. 15A-15E). The SOM evaluations were then oriented using singular value decomposition. The resulting oriented SOM evaluations results were compared with the known positions of the mobile devices arrangement of Test B.

Referring to FIG. 19B, the SOM evaluation illustrated in FIG. 19B was performed with the following parameters: learning rate—0.11 and sigma—9.0 for 800 iterations.

The SOM error was 4385.

Figure 19C:
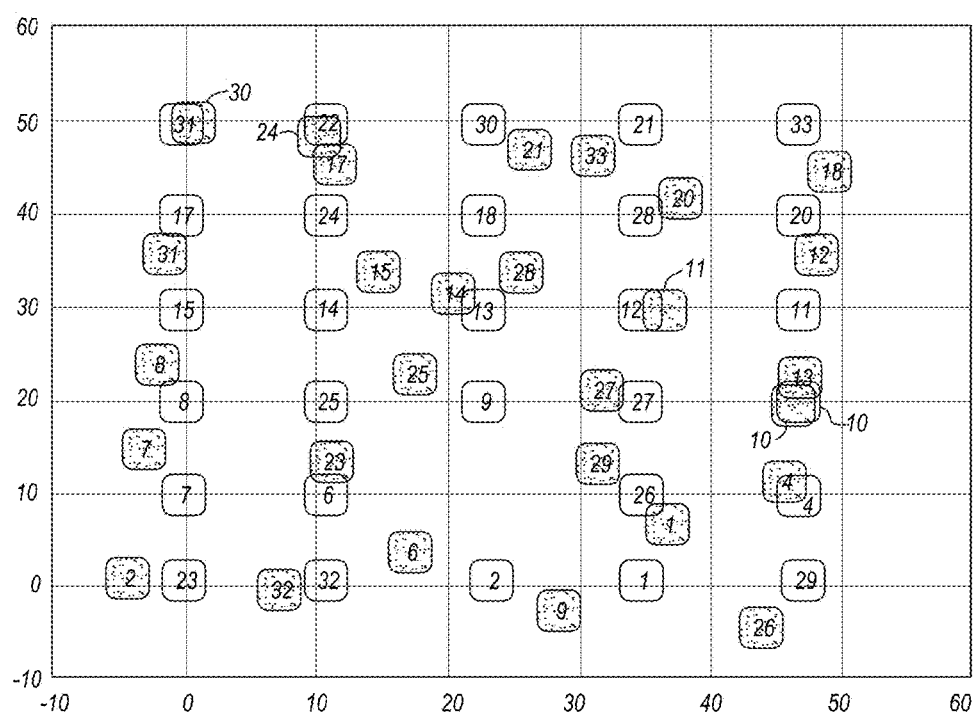
FIG. 19C illustrates a comparison between positions of nodes to SOM evaluated positions after orientation for Test C with 1 min RSSI reading interval.

FIG. 19C illustrates a comparison between positions of nodes to SOM evaluated positions after orientation for Test C with 1 min RSSI reading interval.

SOM evaluations were performed for the mobile phone arrangements of Test C (using the normalized measured distances as discussed with respect to FIGS. 15A-15E). The SOM evaluations were then oriented using singular value decomposition. The resulting oriented SOM evaluations results were compared with the known positions of the mobile devices arrangement of Test C.

Referring to FIG. 19C, the SOM evaluation illustrated in FIG. 19C was performed with the following parameters: learning rate—0.11 and sigma—9.0 for 800 iterations. The SOM error was 6095.

Figure 19D:
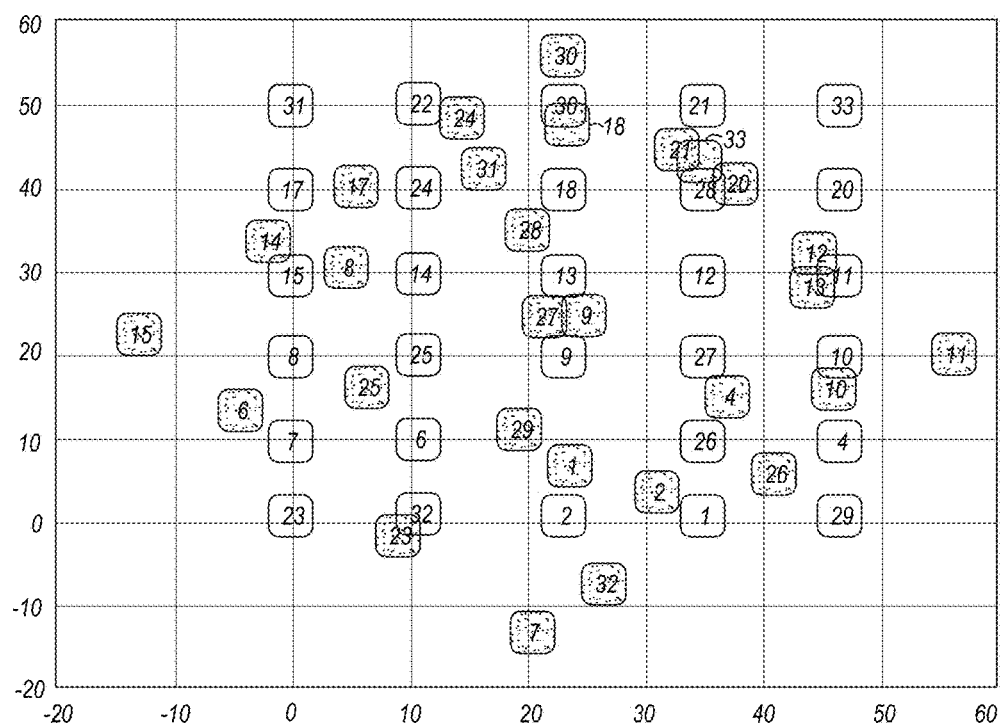
FIG. 19D illustrates a comparison between positions of nodes to SOM evaluated positions after orientation for Test D with 1 min RSSI reading interval.

FIG. 19D illustrates a comparison between positions of nodes to SOM evaluated positions after orientation for Test D with 1 min RSSI reading interval.

SOM evaluations were performed for the mobile phone arrangements of Test D (using the normalized measured distances as discussed with respect to FIG. 15A-15E). The SOM evaluations were then oriented using singular value decomposition. The resulting oriented SOM evaluation results were compared with the known positions of the mobile devices arrangement of Test D.

Referring to FIG. 19D, the SOM evaluation illustrated in FIG. 19D was performed with the following parameters: learning rate—0.11 and sigma—9.0 for 800 iterations. The SOM error was 5807.

Figure 20A:
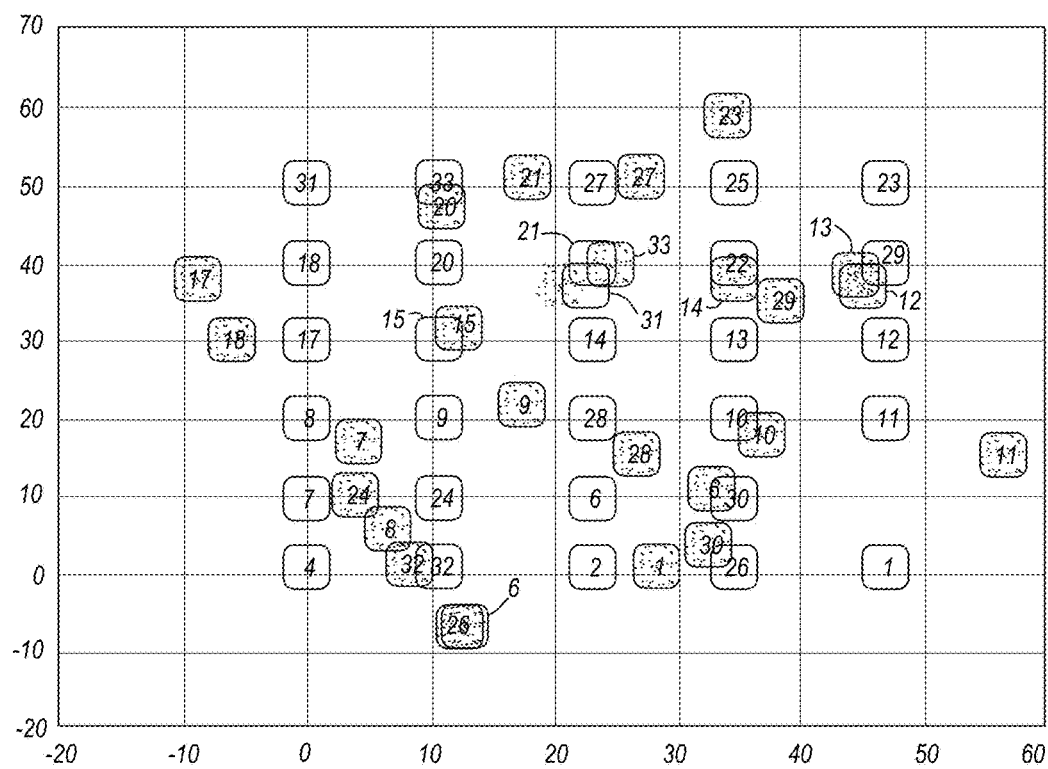
FIG. 20A illustrates a comparison between positions of nodes to SOM evaluated positions after orientation for Test A with 2 min RSSI reading interval.

FIG. 20A illustrates a comparison between positions of nodes to SOM evaluated positions after orientation for Test A with 2 min RSSI reading interval.

SOM evaluations were performed for the mobile phone arrangements of Test A (using the normalized measured distances as discussed with respect to FIGS. 15A-15E). The SOM evaluations were then oriented using singular value decomposition. The resulting oriented SOM evaluation results were compared with the known positions of the mobile devices arrangement of Test A.

Referring to FIG. 20A, the SOM evaluation illustrated in FIG. 20A was performed with the following parameters: learning rate—0.31 and sigma—13.0 for 800 iterations. The SOM error was 4706.

Figure 20B:
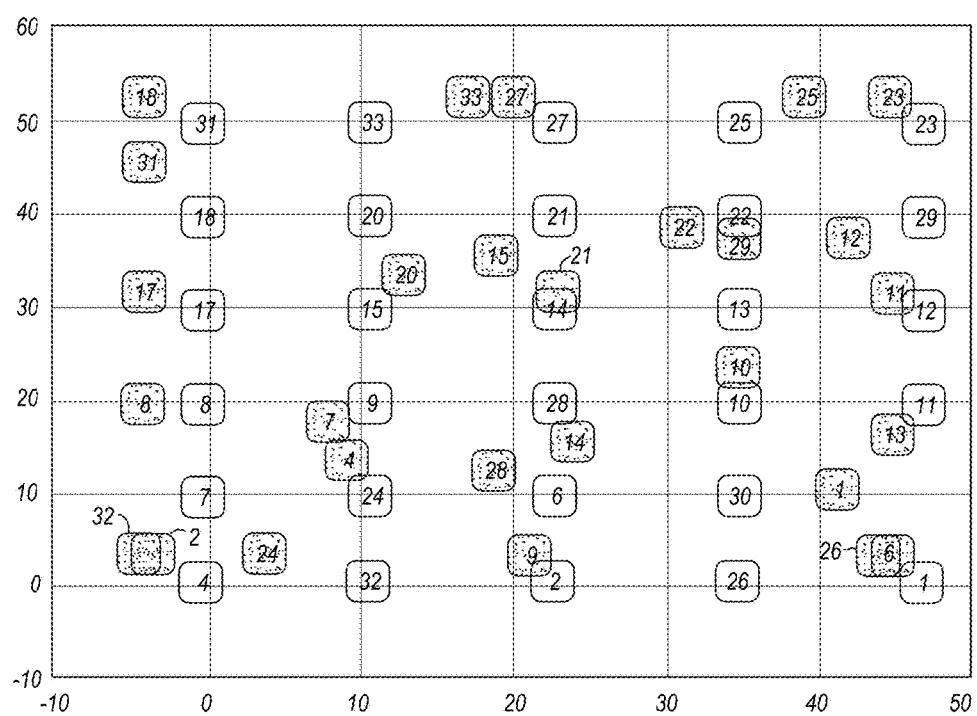
FIG. 20B illustrates a comparison between positions of nodes to SOM evaluated positions after orientation for Test B with 2 min RSSI reading interval.

FIG. 20B illustrates a comparison between positions of nodes to SOM evaluated positions after orientation for Test B with 2 min RSSI reading interval.

SOM evaluations were performed for the mobile phone arrangements of Test B (using the normalized measured distances as discussed with respect to FIGS. 15A-15E). The SOM evaluations were then oriented using singular value decomposition. The resulting oriented SOM evaluations results were compared with the known positions to mobile devices arrangement of Test B.

Referring to FIG. 20B, the SOM evaluation illustrated in FIG. 20B was performed with the following parameters: learning rate—0.31 and sigma—13.0 for 800 iterations. The SOM error was 4196.

Figure 20C:
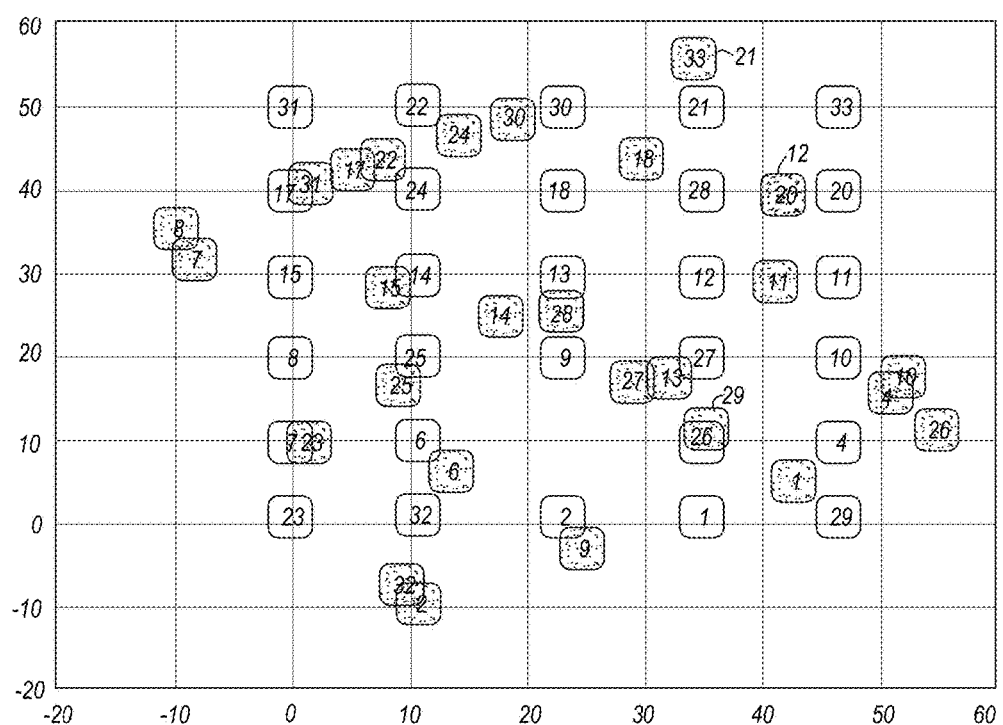
FIG. 20C illustrates a comparison between positions of nodes to SOM evaluated positions after orientation for Test C with 2 min RSSI reading interval.

FIG. 20C illustrates a comparison between positions of nodes to SOM evaluated positions after orientation for Test C with 2 min RSSI reading interval.

SOM evaluations were performed for the mobile phone arrangements of Test C (using the normalized measured distances as discussed with respect to FIGS. 15A-15E). The SOM evaluations were then oriented using singular value decomposition. The resulting oriented SOM evaluation results were compared with the known positions of the mobile devices arrangement of Test C.

Referring to FIG. 20C, the SOM evaluation illustrated in FIG. 18C was performed with the following parameters: learning rate—0.31 the sigma—13.0 for 800 iterations. The SOM error was 4159.

Figure 20D:
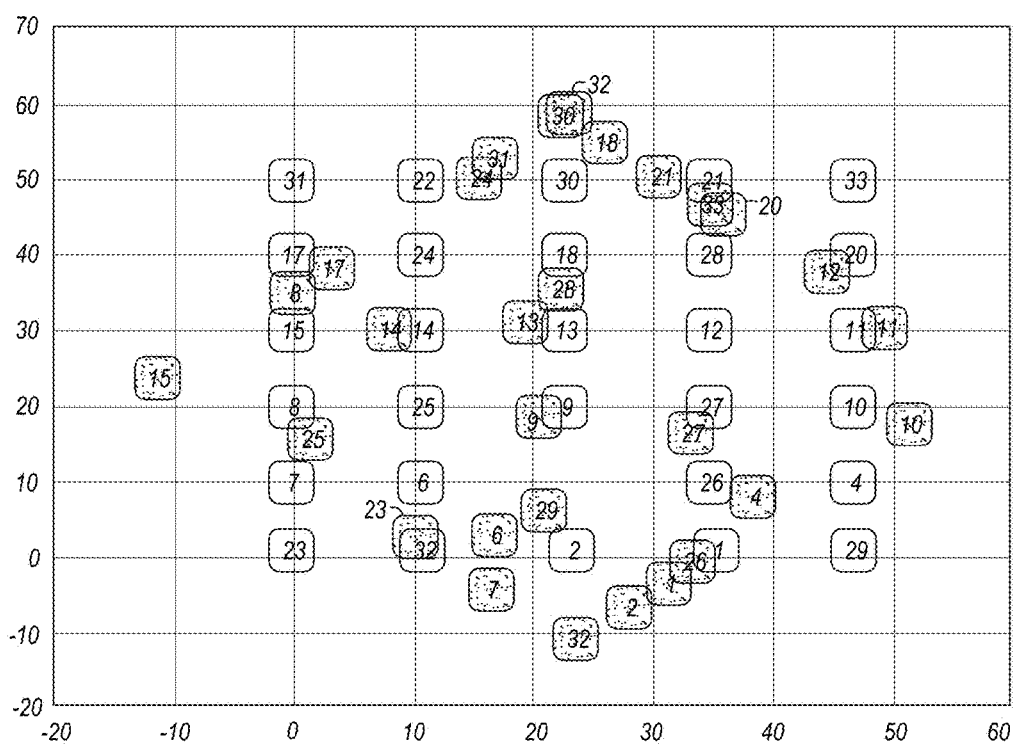
FIG. 20D illustrates a comparison between positions of nodes to SOM evaluated positions after orientation for Test D with 2 min RSSI reading interval.

FIG. 20D illustrates a comparison between positions of nodes to SOM evaluated positions after orientation for Test D with 2 min RSSI reading interval.

SOM evaluations were performed for the mobile phone arrangements of Test D (using the normalized measured distances as discussed with respect to FIGS. 15A-15E). The SOM evaluations were then oriented using singular value decomposition. The resulting oriented SOM evaluations results were compared with the known positions of the mobile devices arrangement of Test D.

Referring to FIG. 20D, the SOM evaluation illustrated in FIG. 20D was performed with the following parameters: learning rate—0.31 and sigma—13.0 for 800 iterations. The SOM error was 4171.

Figure 21A:
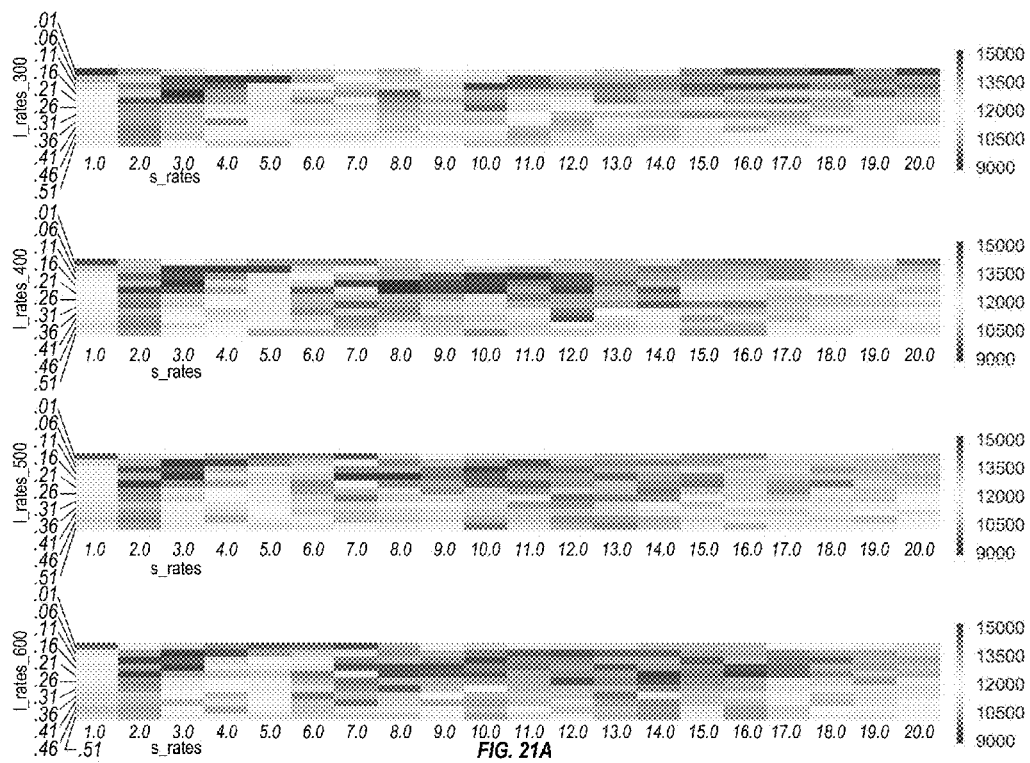
FIG. 21A illustrates a comparison among the average error rates of SOM evaluated positions with different SOM parameters for 5 sec RSSI reading interval.
Figure 21A:
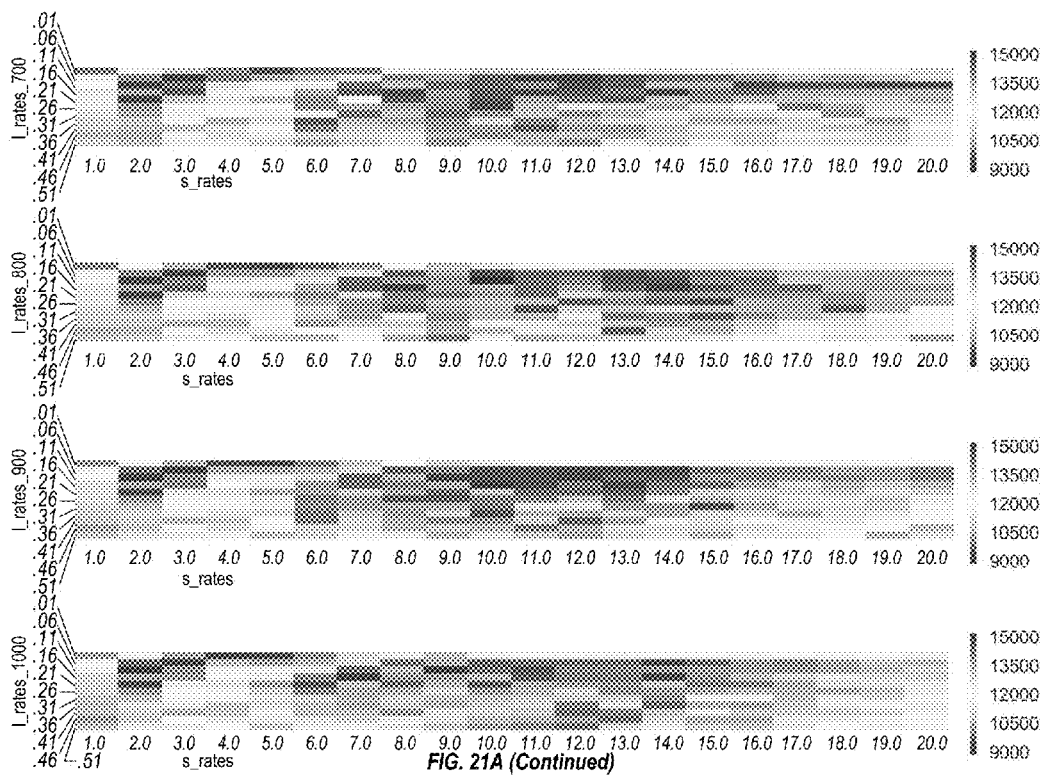

FIG. 21A illustrates a comparison among the average error rates of SOM evaluated positions with different SOM parameters for 5 sec RSSI reading interval.

The SOM evaluations for Test A, B, C, and D (some samples of the SOM evaluations were discussed with respect to FIGS. 17A-D, 18A-D, 19A-D, and 20A-D) were performed using a range of parameters. The learning rates used were 0.01, 0.06, 0.11, 0.16, 0.21, 0.26, 0.31, 0.36, 0.41, 0.46, and 0.51. The sigma used were from 1.0 to 20.0.

Referring to FIG. 21A, the average SOM error ranged from 8965 to 15286. The SOM parameters leading to the minimum SOM error were 0.16 for the learning rate and 3.0 for sigma, for 300 iterations of the SOM.

Figure 21B:
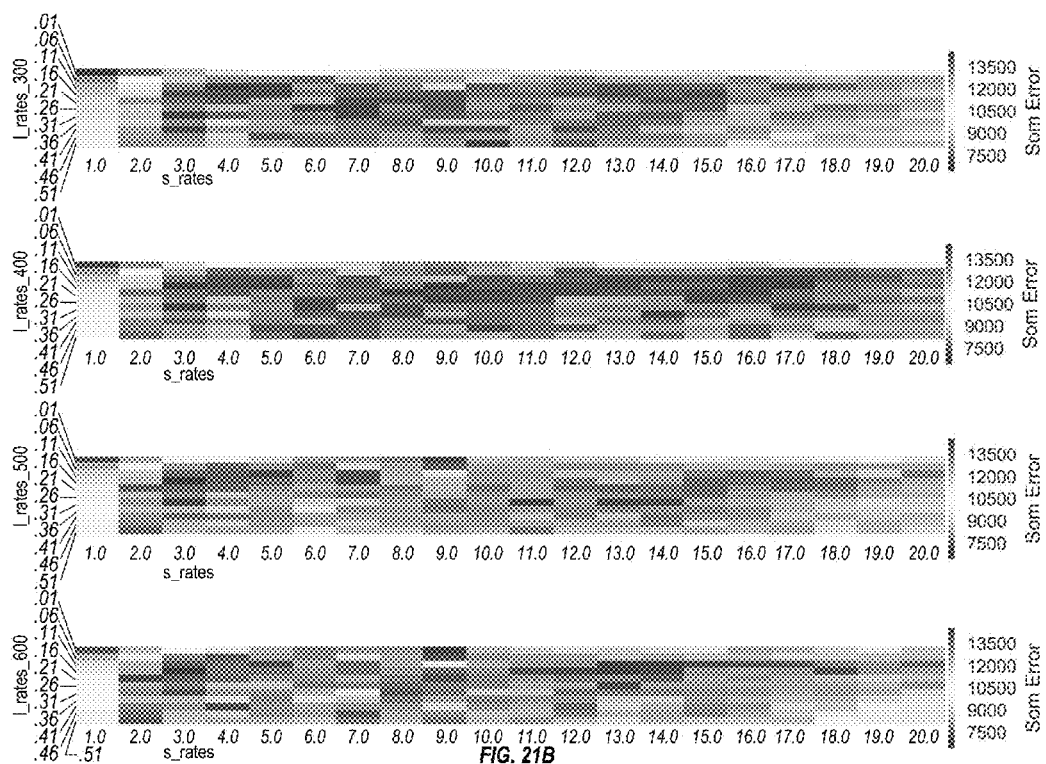
FIG. 21B illustrates a comparison among the average error rates of SOM evaluated positions with different SOM parameters for 30 sec RSSI reading interval.
Figure 21B:
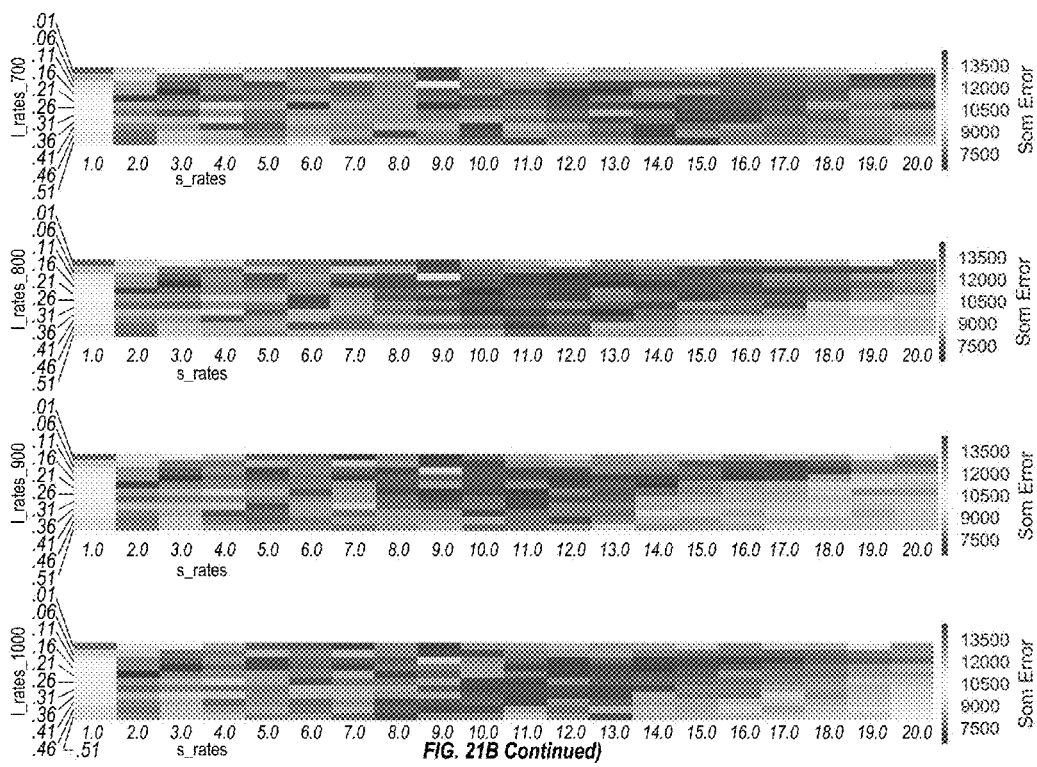

FIG. 21B illustrates a comparison among the average error rates of SOM evaluated positions with SOM parameters for 30 sec RSSI reading interval.

The SOM evaluations for Test A, B, C, and D (some examples of the SOM evaluations were discussed with respect to FIGS. 17A-D, 18A-D, 19A-D, and 20A-D) were performed using a range of parameters. The learning rates used were 0.01, 0.06, 0.11, 0.16, 0.21, 0.26, 0.31, 0.36, 0.41, 0.46, and 0.51. The sigma used from 1.0 to 20.0.

Referring to FIG. 21B, the average SOM error ranged from 6555 to 14687. The SOM parameters leading to the minimum SOM error were 0.16 for the learning rate and 3.0 for sigma, for 600 iterations of the SOM.

Figure 21C:
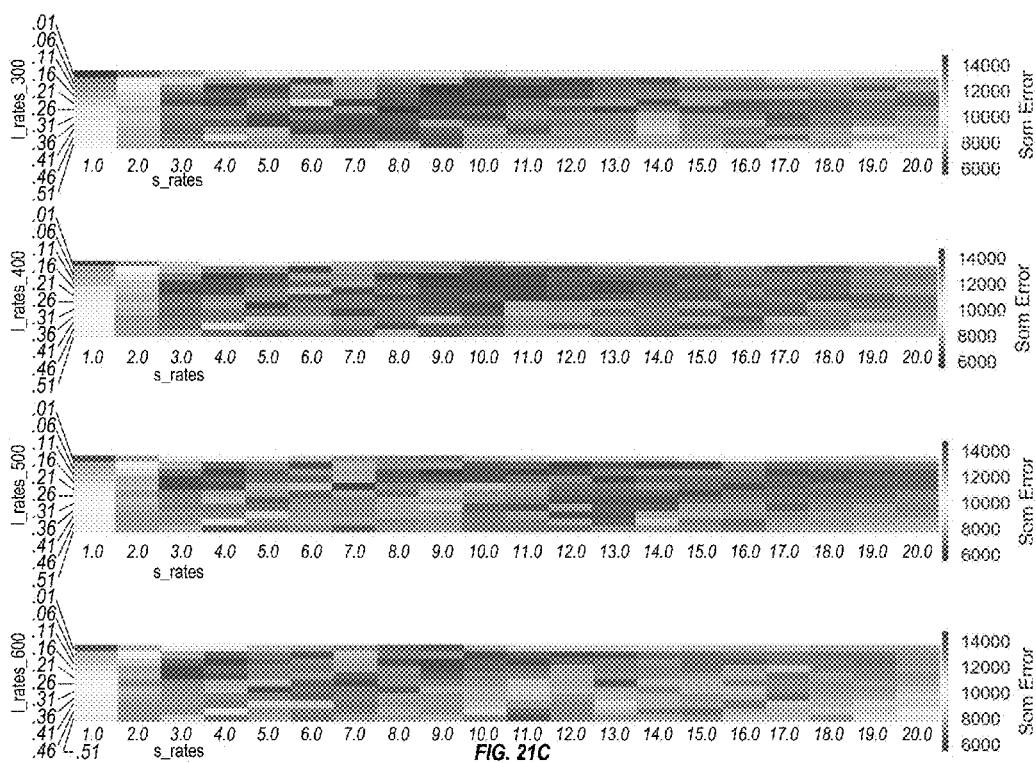
FIG. 21C illustrates a comparison among the average error rates of SOM evaluated positions with different SOM parameters for 1 min RSSI reading interval.
Figure 21C:
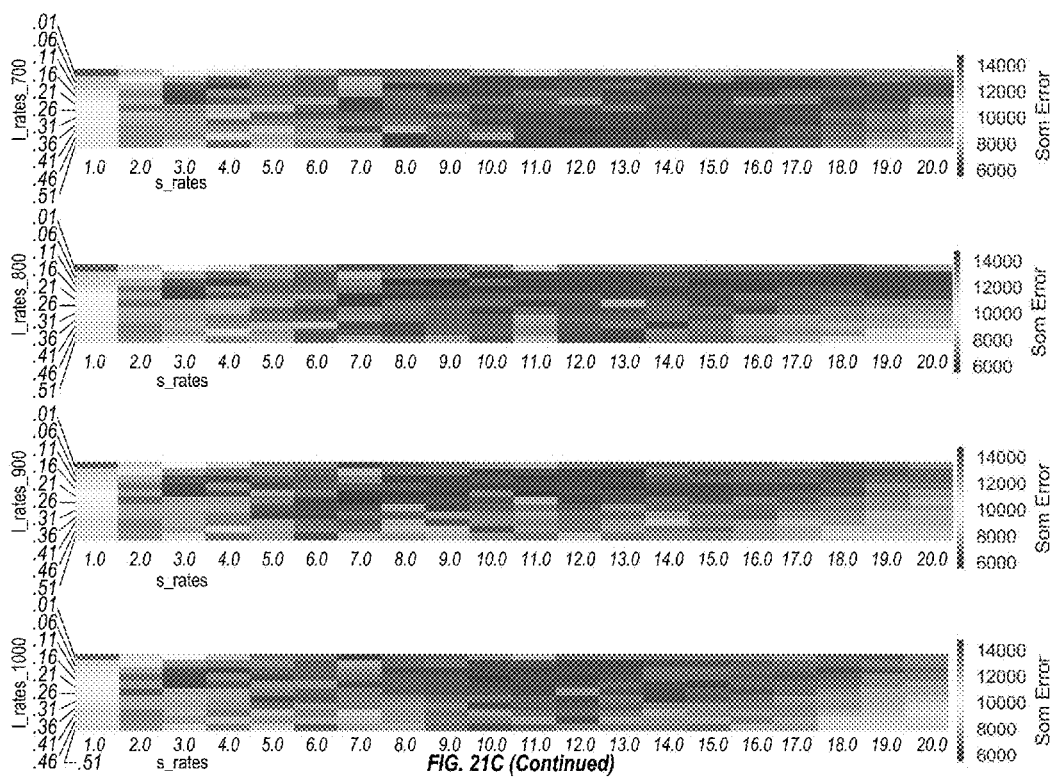

FIG. 21C illustrates a comparison among the average error rates of SOM evaluated positions with different SOM parameters for 1 min RSSI reading interval.

The SOM evaluations for Test A, B, C, and D (some samples of the SOM evaluations were discussed with respect to FIGS. 17A-D, 18A-D, 19A-D, and 20A-D) were performed using a range of parameters. The learning rates used were 0.01., 0.06, 0.11, 0.16, 0.21, 0.26, 0.31, 0.36, 0.41, 0.46, and 0.51. The sigma used were from 1.0 to 20.0.

Referring to FIG. 21C, the average SOM error ranged from 5662 to 14907. The SOM parameters leading to the minimum SOM error were 0.11 for the learning rate and 9.0 for sigma, for 800 iterations of the SOM.

Figure 21D:
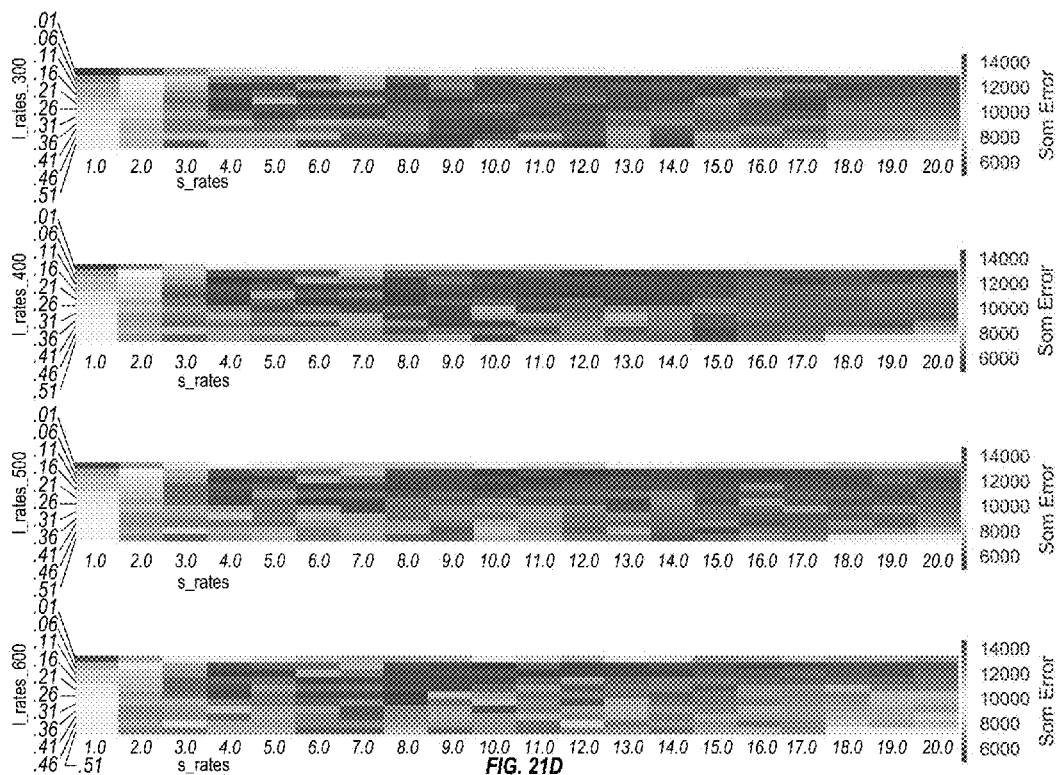
FIG. 21D illustrates a comparison among the average error rates of SOM evaluated positions with different SOM parameters for 2 min RSSI reading interval.
Figure 21D:
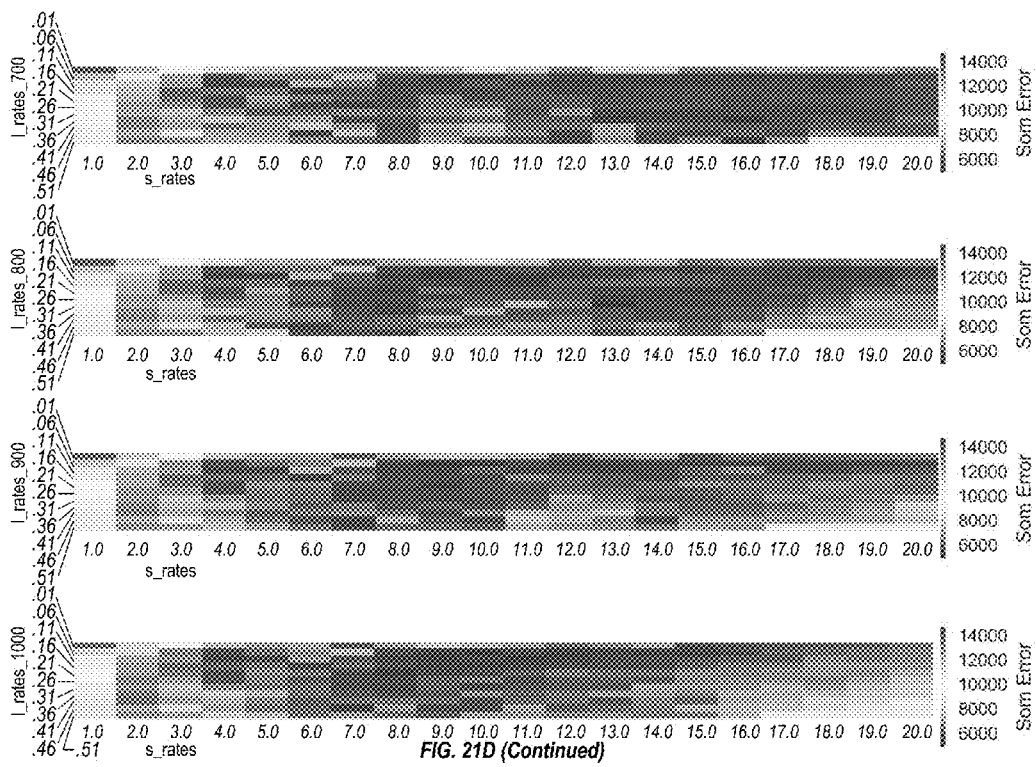

FIG. 21D illustrates a comparison among the average error rates of SOM evaluated positions with different SOM parameters for 2 min RSSI reading interval.

The SOM evaluations for Test A, B, C, and D (some samples of the SOM evaluations were discussed with respect to FIGS. FIGS. 17A-D, 18A-D, 19A-D, and 20A-D) were performed using a range of parameters. The learning rates used were 0.01, 0.06, 0.11, 0.16 0.21, 0.26, 0.31, 0.36, 0.41, 0.46, and 0.51. The sigma used were from 1.0 to 20.0.

Referring to FIG. 21D, the average SOM error ranged from 5061 to 14827. The SOM parameters leading to the minimum SOM error were 0.31 for the learning rate and 13.0 for sigma, for 800 iterations of the SOM.

To avoid unnecessarily obscuring the present disclosure, the preceding description may omit a number of known structures and devices. The omission is not to be construed as a limitation of the scopes of the claims. Specific details are set forth to provide an understanding of the present disclosure. It should however be appreciated that the present disclosure may be practiced in a variety of ways beyond specific detail set forth herein.

Furthermore, while the exemplary aspects, embodiments, and/or configurations illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, or collocated on a particular node of a distributed network, such as an analog and/or digital telecommunications network, packet-switch network, or a circuit-switched network. It will be appreciated from the preceding description, and for reasons of computational efficiency, that the components of the system can be arranged at any location within a distributed network of components without affecting the operation of the system. For example, the various components can be located in a switch such as a PBX and media server, gateway, in one or communications devices, at one or more users' premises, or some combination thereof. Similarly, one or more functional portions of the system could be distributed between a telecommunication device(s) and an associated computing device.

Furthermore, it should be appreciated that the various links connection the elements can be wired or wireless links, or any combination thereof, or any other known or later developed element(s) that is capable of supplying and/or communicating data to and from the connected elements. These wired or wireless links can be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Also, while the flowcharts have been discussed and illustrated in relation to a particular sequence of events, it should be appreciated that changes, addition and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as a discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source-code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, , a special purpose computer, a processor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although, the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein and other similar standards and protocols not mentioned herein are periodically suspended by faster or more effective equivalents having essentially the same functions. Such replacement standards and protocols having the same functions are considered equivalents included in the present disclosure.

The present disclosure, in various aspects, embodiments, and/or configurations, includes components, methods, processes, systems and/or apparatus substantially as depicted and described herein, including various aspects, embodiments, configurations embodiments, sub combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configuration hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. The method of disclosure is not to be interpreted as reflecting an intention that the claims require more features than are expressly recited in each claim. Rather, as the following claims reflect, inventive aspects lie in less than all features of a single to foregoing disclosed aspect, embodiment, and/or configuration. Thus, the following claims are hereby incorporated to this description, with each claim standing on its own as a separate preferred embodiment of the disclosure.

Moreover, though the description has included a description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for wireless location, comprising:
receiving measurements of a plurality of signal strength values from a plurality of nodes over a time interval, wherein the signal strength values are representative of signal strengths of respective plurality of wireless signals transmitted by at least one of the nodes to at least one other of the nodes, wherein each of the nodes comprises a different mobile device, and wherein the nodes are located in an area;
normalizing the signal strength values, wherein the normalizing comprises normalizing the signal strength values with a normalization function, wherein the normalization function is based on a fit of previously collected signal strength values to a pre-determined normalization range within the area;
evaluating respective locations within the area of the nodes based on the normalized signal strength values, wherein the evaluating comprises evaluating using machine learning technique on the normalized signal strength values, wherein the machine learning technique is trained to minimize an error to the locations, and wherein the machine learning technique comprises a self-organizing map (SOM);
orienting the locations to an orientation representative of an orientation of the nodes using one or more of a singular value decomposition and a wireless location technique; and
transmitting respective data to at least one of the nodes for autonomously controlling respective a display of the at least one node based on the data and a location of the at least one node, and wherein the autonomously controlling is not responsive to user input,
wherein the area includes an indoor facility less than 40 m by 40 m, and
wherein a distance between at least two of the nodes is less than 5 m.

2. The method of claim 1, wherein at least one of the nodes include a different type of equipment for transmitting or receiving the wireless signal than at least one other of the nodes.

3. The method of claim 1, wherein the wireless signals comprise BLUETOOTH signals.

4. The method of claim 1, wherein the wireless signals comprise wireless signals of communication in a mesh network, and wherein at least two of the nodes are part of the mesh network.

5. The method of claim 4, wherein the evaluating is performed by the mesh network.

6. The method of claim 1, wherein the previously collected signal strength values are collected from nodes with similar types of wireless equipment as the nodes for transmitting or receiving the wireless signals.

7. The method of claim 1, wherein the fit comprises an exponential fit.

8. The method of claim 1, wherein the normalization function is based on a fit of averages of the previously collected signal strength values of nodes at a substantially same distance.

9. The method of claim 1, wherein the transmitting is synchronized with music playing in the area in substantially real-time.

10. A method for wireless location, comprising:
receiving measurements of a plurality of signal strength values from a plurality of nodes over a time interval, wherein the signal strength values are representative of signal strengths of respective plurality of wireless signals transmitted by at least one of the nodes to at least one other of the nodes, wherein each of the nodes comprises a different mobile device, and wherein the nodes are located in an area;
normalizing the signal strength values, wherein the normalizing comprises normalizing the signal strength values with a normalization function, wherein the normalization function is based on a fit of previously collected signal strength values to a pre-determined normalization range within the area;
evaluating respective locations within the area of the nodes based on the normalized signal strength values, wherein the evaluating comprises evaluating using machine learning technique on the normalized signal strength values, wherein the machine learning technique is trained to minimize an error to the locations, and wherein the machine learning technique comprises a self-organizing map (SOM);
orienting the locations to an orientation representative of an orientation of the nodes using one or more of a singular value decomposition and a wireless location technique;
transmitting respective data to at least one of the nodes for autonomously controlling respective a display of the at least one node based on the data and a location of the at least one node, and wherein the autonomously controlling is not responsive to user input; and
transmitting respective data to another at least one of the nodes for autonomously controlling a display of the another at least one node based on the data and a location of the another at least one node,
wherein the autonomously controlling of the display of the another at least one node is not responsive to user input,
wherein the display of the at least one node and the display of the another at least one node is different based on different locations of the at least one node and the another at least one node,
wherein the area includes an indoor facility less than 40 m by 40 m, and
wherein a distance between at least two of the nodes is less than 5 m.

11. The method of claim 10, wherein at least one of the nodes include a different type of equipment for transmitting or receiving the wireless signal than at least one other of the nodes.

12. The method of claim 11, wherein the wireless signals comprise BLUETOOTH signals.

13. The method of claim 10, wherein the wireless signals comprise wireless signals of communication in a mesh network, and wherein at least two of the nodes are part of the mesh network.

14. The method of claim 13, wherein the evaluating is performed by the mesh network.

15. The method of claim 10, wherein the previously collected signal strength values are collected from nodes with similar types of wireless equipment as the nodes for transmitting or receiving the wireless signals.

16. The method of claim 10, wherein the fit comprises an exponential fit.

17. The method of claim 10, wherein the normalization function is based on a fit of averages of the previously collected signal strength values of nodes at a substantially same distance.

18. The method of claim 10, wherein the transmitting is synchronized with music playing in the area in substantially real-time.

19. The method of claim 18, wherein the controlling is based on a rhythm of the music.

20. A method for wireless location, comprising:
   receiving measurements of a plurality of signal strength values from a plurality of nodes over a time interval, wherein the signal strength values are representative of signal strengths of respective plurality of wireless signals transmitted by at least one of the nodes to at least one other of the nodes, wherein each of the nodes comprises a different mobile device, and wherein the nodes are located in an area;
   normalizing the signal strength values, wherein the normalizing comprises normalizing the signal strength values with a normalization function, wherein the normalization function is based on a fit of previously collected signal strength values to a pre-determined normalization range within the area;
   evaluating respective locations within the area of the nodes based on the normalized signal strength values, wherein the evaluating comprises evaluating using machine learning technique on the normalized signal strength values, wherein the machine learning technique is trained to minimize an error to the locations, and wherein the machine learning technique comprises a self-organizing map (SOM);
   orienting the locations to an orientation representative of an orientation of the nodes using one or more of a singular value decomposition and a wireless location technique; and
   transmitting respective data to at least one of the nodes for autonomously controlling respective a display of the at least one node based on the data and a location of the at least one node, and wherein the autonomously controlling is not responsive to user input,
   wherein the transmitting is synchronized with music playing in the area in substantially real-time,
   wherein the controlling is based on a rhythm of the music,
   wherein the area includes an indoor facility less than 40 m by 40 m, and
   wherein a distance between at least two of the nodes is less than 5 m.

\* \* \* \* \*